United States Patent
Irwin et al.

(10) Patent No.: US 11,685,666 B2
(45) Date of Patent: Jun. 27, 2023

(54) METAL OXIDE NANOPARTICLES WITH ALKYLSILOXANE LIGANDS BONDED THERETO

(71) Applicant: CubicPV Inc., Dallas, TX (US)

(72) Inventors: Michael David Irwin, Heath, TX (US); Marissa Lynn Higgins, Forney, TX (US); Nicholas Charles Anderson, Dallas, TX (US)

(73) Assignee: CubicPV Inc., Dallas, TX (US)

( * ) Notice: Subject to any disclaimer, the term of this patent is extended or adjusted under 35 U.S.C. 154(b) by 0 days.

(21) Appl. No.: 17/509,271

(22) Filed: Oct. 25, 2021

(65) Prior Publication Data

US 2022/0041462 A1 Feb. 10, 2022

Related U.S. Application Data

(62) Division of application No. 17/106,002, filed on Nov. 27, 2020, now Pat. No. 11,186,495.

(60) Provisional application No. 62/941,066, filed on Nov. 27, 2019.

(51) Int. Cl.
| | |
|---|---|
| *C01G 33/00* | (2006.01) |
| *H01L 51/44* | (2006.01) |
| *C01G 35/00* | (2006.01) |
| *C07D 221/18* | (2006.01) |
| *H01L 51/42* | (2006.01) |
| *C07F 7/08* | (2006.01) |
| *B82Y 30/00* | (2011.01) |
| *B82Y 40/00* | (2011.01) |

(52) U.S. Cl.
CPC ............ *C01G 33/00* (2013.01); *C01G 35/00* (2013.01); *C07D 221/18* (2013.01); *C07F 7/0834* (2013.01); *H01L 51/426* (2013.01); *H01L 51/441* (2013.01); *B82Y 30/00* (2013.01); *B82Y 40/00* (2013.01); *H01L 2251/303* (2013.01)

(58) Field of Classification Search
CPC .... C07F 7/0834; C01G 33/006; C01G 35/006
See application file for complete search history.

(56) References Cited

U.S. PATENT DOCUMENTS

| | | |
|---|---|---|
| 8,871,310 B2 | 10/2014 | Hyeon et al. |
| 2006/0019098 A1 | 1/2006 | Chan |
| 2008/0145633 A1 | 6/2008 | Kodas |
| 2009/0312457 A1 | 12/2009 | Tokumitsu |
| 2015/0056514 A1 | 2/2015 | Dai |

FOREIGN PATENT DOCUMENTS

| | | |
|---|---|---|
| WO | 2014/161100 | 10/2014 |
| WO | 2016/128133 | 8/2016 |

OTHER PUBLICATIONS

Notification concerning transmittal of international preliminary report on patentability and written opinion of the international searching authority in PCT/US2020/062483, dated Jun. 9, 2022, 7 pages.
Transmittal and PCT International Search Report with Written Opinion for International Application No. PCT/US2020/062483, dated Mar. 26, 2021, 11 pages.
Freedman, J. D. et al., "Tantalum oxide nanoparticles for the imaging of articular cartilage using X-ray computed tomography: visualization of ex vivo/in vivo murine tibia and ex vivo human index finger cartilage", Angewandte Chemie International Edition, 2014, vol. 53, No. 32, pp. 8406-8410, Published Jun. 20, 2014.
Narangari, P. R. et al., "Ultrathin Ta2O5 electron-selective contacts for high efficiency InP solar cells", Nanoscale, Mar. 28, 2019, vol. 11, No. 15, pp. 7497-7505.

*Primary Examiner* — Steven J Bos
(74) *Attorney, Agent, or Firm* — Baker Botts L.L.P.

(57) ABSTRACT

A metal oxide nanoparticle comprises a metal oxide core of formula $M_2O_5$, wherein M is tantalum (V) or niobium (V) and alkylsiloxane ligands bonded to the metal oxide core. The alkylsiloxane ligands are selected from the group consisting of isobutylsiloxane, allylsiloxane, vinylsiloxane, n-propyl siloxane, n-butylsiloxane, sec-butyl siloxane, tert-butyl siloxane, phenylsiloxane, n-octylsiloxane, isooctylsiloxane n-dodecyl siloxane, 4-(trimethyl silyl)phenylsiloxane, para-tolylsiloxane, 4-fluorophenyl siloxane, 4-chlorophenyl siloxane, 4-bromophenyl siloxane, 4-iodophenylsiloxane, 4-cyanophenyl siloxane, benzylsiloxane, methylsiloxane, ethylsiloxane, 4-(trifluoromethyl)phenylsiloxane, 4-ammoniumbutylsiloxane, and any combination thereof.

5 Claims, 55 Drawing Sheets

1,8-Diammonium Octane

Bis(4-aminobutyl)-ammonium

Tris(4-aminobutyl)-ammonium 1-(4-alkylphenyl)methanamine 1-(4-alkyl-2-phenyl)ethanamine 1-(4-alkylphenyl)methanamine 1-(4-alkyl-2-phenyl)ethanamine 1-(3-alkyl-5-alkylphenyl)methanamine 1-(3-alkyl-5-alkyl-2-phenyl)ethanamine 2-Ethylamine-7-alkyl-Naphthalene 2-Ethylamine-6-alkyl-Naphthalene 1-Ethylamine-6-alkyl-Naphthalene 1-Ethylamine-7-alkyl-Naphthalene 2-Methylamine-7-alkyl-Naphthalene 2-Methylamine-6-alkyl-Naphthalene 1-Methylamine-6-alkyl-Naphthalene 1-Methylamine-7-alkyl-Naphthalene N-*n*-aminoalkyl-N'-4-aminobutylperylene-3,4,9,10-bis(dicarboximide)

1-(4-Pentylphenyl)methanamine 1-(3-Butyl-5-methoxybutylphenyl)methanamine

1-[4-(2-Methylpentyl)-2-phenyl]ethanamine 1-(3-Butyl-5-pentyl-2-phenyl)ethanamine 2-(5-[4-Methylpentyl]-2-naphthyl)ethanamine N-*n*-heptyl-N'-4-aminobutylperylene-3,4,9,10-bis(dicarboximide)

N-7-tridecyl-N'-4-aminobutylperylene-3,4,9,10-bis(dicarboximide)

2-(6-[3-Methoxylpropyl]-2-naphthyl)ethanamine

METAL OXIDE NANOPARTICLES WITH ALKYLSILOXANE LIGANDS BONDED THERETO

CROSS-REFERENCE TO RELATED APPLICATIONS

This application is a divisional application of U.S. patent application Ser. No. 17/106,002 filed Nov. 27, 2020, which claims priority to U.S. Provisional Patent Application No. 62/941,066 filed Nov. 27, 2019, the contents of which are incorporated by reference herein in their entirety.

BACKGROUND

Use of photovoltaics (PVs) to generate electrical power from solar energy or radiation may provide many benefits, including, for example, a power source, low or zero emissions, power production independent of the power grid, durable physical structures (no moving parts), stable and reliable systems, modular construction, relatively quick installation, safe manufacture and use, and good public opinion and acceptance of use.

PVs may incorporate layers of perovskite materials as photoactive layers that generate electric power when exposed to light. Additional layers in PV devices may assist transport of charge from the photoactive layer. Selection of charge transporting layers may affect PV device performance and durability.

The features and advantages of the present disclosure will be readily apparent to those skilled in the art. While numerous changes may be made by those skilled in the art, such changes are within the spirit of the invention.

SUMMARY

According to some embodiments, a nanoparticle includes a metal oxide core having the formula $M_2O_5$ wherein M is either tantalum (V) or niobium (V) and alkylsiloxane ligands surrounding the metal oxide core.

According to some embodiments, a method for producing a metal (V) oxide nanoparticles includes reacting a metal (V) alkoxide and an alkylcarboxylic acid in a solution comprising water and an alcohol to form metal (V) oxide nanoparticle cores. The metal (V) oxide nanoparticle cores are introduced and an alkoxyalkylsilane into a solvent comprising an alcohol. Ammonium hydroxide is introduced into the solvent comprising an alcohol that contains the metal (V) oxide nanoparticle cores and alkoxyalkylsilane. Hydrogen chloride is introduced into the solvent comprising an alcohol that contains the metal (V) oxide nanoparticle cores and alkoxyalkylsilane after introduction of the ammonium hydroxide to form metal (V) oxide nanoparticles.

According to some embodiments, a semiconducting device includes a layer of perovskite material and a layer of metal (V) oxide nanoparticles. The metal (V) oxide nanoparticles include metal (V) oxide cores having the formula $M_2O_5$ surrounded by alkylsiloxane ligands.

DETAILED DESCRIPTION OF PREFERRED EMBODIMENTS

Improvements in various aspects of PV technologies compatible with organic, non-organic, and/or hybrid PVs promise to further lower the cost of both organic PVs and other PVs. For example, some solar cells, such as perovskite PV solar cells, may take advantage of novel cost-effective and high-stability alternative components, such as nickel oxide interfacial layers. In addition, various kinds of solar cells may advantageously include chemical additives and other materials that may, among other advantages, be more cost-effective and durable than conventional options currently in existence.

The present disclosure relates generally to compositions of matter, apparatus and methods of use of materials in photovoltaic cells in creating electrical energy from solar radiation. More specifically, this disclosure relates to photoactive and other compositions of matter, as well as apparatus, methods of use, and formation of such compositions of matter.

Some or all of materials in accordance with some embodiments of the present disclosure may also advantageously be used in any organic or other electronic device, with some examples including, but not limited to: batteries, field-effect transistors (FETs), light-emitting diodes (LEDs), non-linear optical devices, memristors, capacitors, rectifiers, and/or rectifying antennas.

In some embodiments, the present disclosure may provide PV and other similar devices (e.g., batteries, hybrid PV batteries, multi junction PVs, FETs, LEDs, x-ray detectors, gamma ray detectors, photodiodes, CCDs, etc.). Such devices may in some embodiments include improved active material, interfacial layers (IFLs), and/or one or more perovskite materials. A perovskite material may be incorporated into various of one or more aspects of a PV or other device. A perovskite material according to some embodiments may be of the general formula $CMX_3$, where: C comprises one or more cations (e.g., an amine, ammonium, phosphonium, a Group 1 metal, a Group 2 metal, and/or other cations or cation-like compounds); M comprises one or more metals (examples including Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr); and X comprises one or more anions. Perovskite materials according to various embodiments are discussed in greater detail below.

Photovoltaic Cells and Other Electronic Devices

Figure 1:
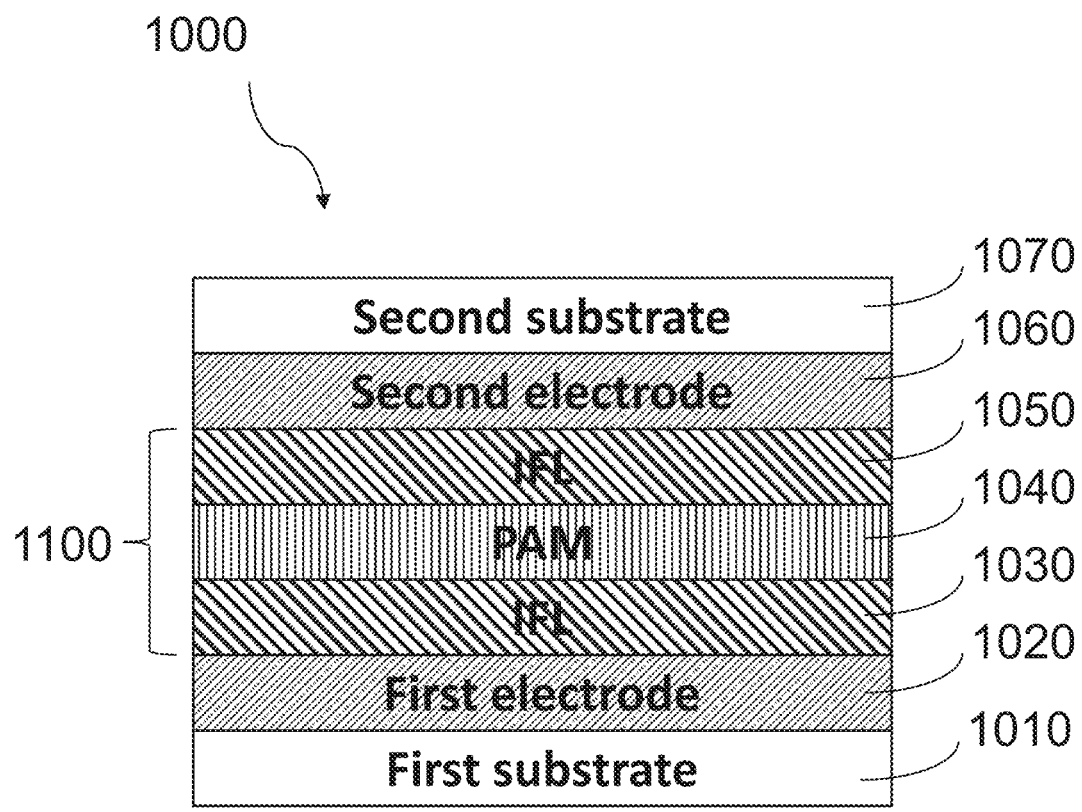
FIG. 1 is a schematic view of a typical photovoltaic (PV) cell including an active layer, according to some embodiments of the present disclosure.

Some PV embodiments may be described by reference to the illustrative depictions of solar cells as shown in FIG. 1. An example PV architecture according to some embodiments may be substantially of the form substrate-anode-IFL-active layer-IFL-cathode. The active layer of some embodiments may be photoactive, and/or it may include photoactive material. Other layers and materials may be utilized in the cell as is known in the art. Furthermore, it should be noted that the use of the term "active layer" is in no way meant to restrict or otherwise define, explicitly or implicitly, the properties of any other layer—for instance, in some embodiments, either or both IFLs may also be active insofar as they may be semiconducting. In particular, referring to FIG. 1, a stylized generic PV cell 1000 is depicted, illustrating the highly interfacial nature of some layers within the PV. The PV 1000 represents a generic architecture applicable to several PV devices, such as perovskite material PV embodiments. The PV cell 1000 includes a transparent substrate layer 1010, which may be glass (or a material similarly transparent to solar radiation) which allows solar radiation to transmit through the layer. The transparent layer of some embodiments may also be referred to as a superstrate or substrate (e.g., as with substrate layer 3901 of FIG. 2), and it may comprise any one or more of a variety of rigid or flexible materials such as: glass, polyethylene, polypropylene, polycarbonate, polyimide, PMMA, PET, PEN, Kapton, or quartz. In general, the term substrate is used to refer to material upon which the device is deposited during manufacturing. The photoactive layer 1040 may be composed of electron donor or p-type material, and/or an electron acceptor or n-type material, and/or an ambipolar semiconductor, which exhibits both p- and n-type material characteristics, and/or an intrinsic semiconductor which exhibits neither n-type or p-type characteristics. Photoactive layer 1040 may be a perovskite material as described herein, in some embodiments. The active layer or, as depicted in FIG. 1, the photo-active layer 1040, is sandwiched between two electrically conductive electrode layers 1020 and 1060. In FIG. 1, the electrode layer 1020 may be a transparent conductor such as a tin-doped indium oxide (ITO material) or other material as described herein. In other embodiments second substrate 1070 and second electrode 1060 may be transparent. As previously noted, an active layer of some embodiments need not necessarily be photoactive, although in the device shown in FIG. 1, it is. The electrode layer 1060 may be an aluminum material or other metal, or other conductive materials such as carbon. Other materials may be used as is known in the art. The cell 1010 also includes an interfacial layer (IFL) 1030, shown in the example of FIG. 1. The IFL may assist in charge separation. In other embodiments, the IFL 1030 may comprise a multi-layer IFL, which is discussed in greater detail below. There also may be an IFL 1050 adjacent to electrode 1060. In some embodiments, the IFL 1050 adjacent to electrode 1060 may also or instead comprise a multi-layer IFL (again, discussed in greater detail below). An IFL according to some embodiments may be semiconducting in character and may be either intrinsic, ambipolar, p-type, or n-type, or it may be dielectric in character. In some embodiments, the IFL on the cathode side of the device (e.g., IFL 1050 as shown in FIG. 1) may be p-type, and the IFL on the anode side of the device (e.g., IFL 1030 as shown in FIG. 1) may be n-type. In other embodiments, however, the cathode-side IFL may be n-type and the anode-side IFL may be p-type. The cell 1010 may be attached to electrical leads by electrodes 1060 and 1020 and a discharge unit, such as a battery, motor, capacitor, electric grid, or any other electrical load.

Various embodiments of the present disclosure provide improved materials and/or designs in various aspects of solar cell and other devices, including among other things, active materials (including hole-transport and/or electron-transport layers), interfacial layers, and overall device design.

Interfacial Layers

The present disclosure, in some embodiments, provides advantageous materials and designs of one or more interfacial layers within a PV, including thin-coat IFLs. Thin-coat IFLs may be employed in one or more IFLs of a PV according to various embodiments discussed herein.

According to various embodiments, devices may optionally include an interfacial layer between any two other layers and/or materials, although devices need not contain any interfacial layers. For example, a perovskite material device may contain zero, one, two, three, four, five, or more interfacial layers (such as the example device of FIG. 2, which contains five interfacial layers 3903, 3905, 3907, 3909, and 3911). An interfacial layer may include any suitable material for enhancing charge transport and/or collection between two layers or materials; it may also help prevent or reduce the likelihood of charge recombination once a charge has been transported away from one of the materials adjacent to the interfacial layer. An interfacial layer may additionally physically and electrically homogenize its substrates to create variations in substrate roughness, dielectric constant, adhesion, creation or quenching of defects (e.g., charge traps, surface states). Suitable interfacial materials may include any one or more of: Ag; Al; Au; B; Bi; Ca; Cd; Ce; Co; Cu; Fe; Ga; Ge; H; In; Mg; Mn; Mo; Nb; Ni; Pt; Sb; Sc; Si; Sn; Ta; Ti; V; W; Y; Zn; Zr; carbides of any of the foregoing metals (e.g., SiC, $Fe_3C$, WC, VC, MoC, NbC); silicides of any of the foregoing metals (e.g., $Mg_2Si$, $SrSi_2$, $Sn_2Si$); oxides of any of the foregoing metals (e.g., alumina, silica, titania, $SnO_2$, ZnO, NiO, $ZrO_2$, $HfO_2$), include transparent conducting oxides ("TCOs") such as indium tin oxide, aluminum doped zinc oxide (AZO), cadmium oxide (CdO), and fluorine doped tin oxide (FTO); sulfides of any of the foregoing metals (e.g., CdS, $MoS_2$, $SnS_2$); nitrides of any of the foregoing metals (e.g., GaN, $Mg_3N_2$, TiN, BN, $Si_3N_4$); selenides of any of the foregoing metals (e.g., CdSe, $FeSe_2$, ZnSe); tellurides of any of the foregoing metals (e.g., CdTe, $TiTe_2$, ZnTe); phosphides of any of the foregoing metals (e.g., InP, GaP, GaInP); arsenides of any of the foregoing metals (e.g., $CoAs_3$, GaAs, InGaAs, NiAs); antimonides of any of the foregoing metals (e.g., AlSb, GaSb, InSb); halides of any of the foregoing metals (e.g., CuCl, CuI, $BiI_3$); pseudohalides of any of the foregoing metals (e.g., CuSCN, AuCN, $Fe(SCN)_2$); carbonates of any of the foregoing metals (e.g., $CaCO_3$, $Ce_2(CO_3)_3$); functionalized or non-functionalized alkyl silyl groups; graphite; graphene; fullerenes; carbon nanotubes; any mesoporous material and/or interfacial material discussed elsewhere herein; and combinations thereof (including, in some embodiments, bilayers, trilayers, or multilayers of combined materials). In some embodiments, an interfacial layer may include perovskite material. Further, interfacial layers may comprise doped embodiments of any interfacial material mentioned herein (e.g., Y-doped ZnO, N-doped single-wall carbon nanotubes). Interfacial layers may also comprise a compound having three of the above materials (e.g., $CuTiO_3$, $Zn_2SnO_4$) or a compound having four of the above materials (e.g., CoNiZnO). The materials listed above may be present in a planar, mesoporous or otherwise nano-structured form (e.g. rods, spheres, flowers, pyramids), or aerogel structure.

First, as previously noted, one or more IFLs (e.g., either or both IFLs 2626 and 2627 as shown in FIG. 1) may comprise a photoactive organic compound of the present disclosure as a self-assembled monolayer (SAM) or as a thin film. When a photoactive organic compound of the present disclosure is applied as a SAM, it may comprise a binding group through which it may be covalently or otherwise bound to the surface of either or both of the anode and cathode. The binding group of some embodiments may comprise any one or more of COOH, $SiX_3$ (where X may be any moiety suitable for forming a ternary silicon compound, such as $Si(OR)_3$ and $SiCl_3$), $SO_3$, $PO_4H$, OH, $CH_2X$ (where X may comprise a Group 17 halide), and O. The binding group may be covalently or otherwise bound to an electron-withdrawing moiety, an electron donor moiety, and/or a core moiety. The binding group may attach to the electrode surface in a manner so as to form a directional, organized layer of a single molecule (or, in some embodiments, multiple molecules) in thickness (i.e., where multiple photoactive organic compounds are bound to the anode and/or cathode). As noted, the SAM may attach via covalent interactions, but in some embodiments, it may attach via ionic, hydrogen-bonding, and/or dispersion force (i.e., Van Der Waals) interactions. Furthermore, in certain embodiments, upon light exposure, the SAM may enter into a zwitterionic excited state, thereby creating a highly-polarized IFL, which may direct charge carriers from an active layer into an electrode (e.g., either the anode or cathode). This enhanced charge-carrier injection may, in some embodiments, be accomplished by electronically poling the cross-section of the active layer and therefore increasing charge-carrier drift velocities towards their respective electrode (e.g., hole to anode; electrons to cathode). Molecules for anode applications of some embodiments may comprise tunable compounds that include a primary electron donor moiety bound to a core moiety, which in turn is bound to an electron-withdrawing moiety, which in turn is bound to a binding group. In cathode applications according to some embodiments, IFL molecules may comprise a tunable compound comprising an electron poor moiety bound to a core moiety, which in turn is bound to an electron donor moiety, which in turn is bound to a binding group. When a photoactive organic compound is employed as an IFL according to such embodiments, it may retain photoactive character, although in some embodiments it need not be photoactive.

Metal oxides may be used in thin film IFLs of some embodiments and may include semiconducting metal oxides, such as NiO, $SnO_2$, $WO_3$, $V_2O_5$, or $MoO_3$. The embodiment wherein the second (e.g., n-type) active material comprises $TiO_2$ coated with a thin-coat IFL comprising $Al_2O_3$ could be formed, for example, with a precursor material such as $Al(NO_3)_3 \cdot xH_2O$, or any other material suitable for depositing $Al_2O_3$ onto the $TiO_2$, followed by thermal annealing and dye coating. In example embodiments wherein a $MoO_3$ coating is instead used, the coating may be formed with a precursor material such as $Na_2MoO_4 \cdot 2H_2O$; whereas a $V_2O_5$ coating according to some embodiments may be formed with a precursor material such as $NaVO_3$; and a $WO_3$ coating according to some embodiments may be formed with a precursor material such as $NaWO_4 \cdot H_2O$. The concentration of precursor material (e.g., $Al(NO_3)_3 \cdot xH_2O$) may affect the final film thickness (here, of $Al_2O_3$) deposited on the $TiO_2$ or other active material. Thus, modifying the concentration of precursor material may be a method by which the final film thickness may be controlled. For example, greater film thickness may result from greater precursor material concentration. Greater film thickness may not necessarily result in greater PCE in a PV device comprising a metal oxide coating. Thus, a method of some embodiments may include coating a $TiO_2$ (or other mesoporous) layer using a precursor material having a concentration in the range of approximately 0.5 to 10.0 mM; other embodiments may include coating the layer with a precursor material having a concentration in the range of approximately 2.0 to 6.0 mM; or, in other embodiments, approximately 2.5 to 5.5 mM.

Furthermore, although referred to herein as $Al_2O_3$ and/or alumina, it should be noted that various ratios of aluminum and oxygen may be used in forming alumina. Thus, although some embodiments discussed herein are described with reference to $Al_2O_3$, such description is not intended to define a required ratio of aluminum in oxygen. Rather, embodiments may include any one or more aluminum-oxide compounds, each having an aluminum oxide ratio according to $Al_xO_y$, where x may be any value, integer or non-integer, between approximately 1 and 100. In some embodiments, x may be between approximately 1 and 3 (and, again, need not be an integer). Likewise, y may be any value, integer or non-integer, between 0.1 and 100. In some embodiments, y may be between 2 and 4 (and, again, need not be an integer). In addition, various crystalline forms of $Al_xO_y$ may be present in various embodiments, such as alpha, gamma, and/or amorphous forms of alumina.

Likewise, although referred to herein as NiO, $MoO_3$, $WO_3$, and $V_2O_5$, such compounds may instead or in addition be represented as $Ni_xO_y$, $Mo_xO_y$, $W_xO_y$, and $V_xO_y$, respectively. Regarding each of $Mo_xO_y$ and $W_xO_y$, x may be any value, integer or non-integer, between approximately 0.5 and 100; in some embodiments, it may be between approximately 0.5 and 1.5. Likewise, y may be any value, integer or non-integer, between 1 and 100. In some embodiments, y may be any value between approximately 1 and 4. Regarding $V_xO_y$, x may be any value, integer or non-integer, between approximately 0.5 and 100; in some embodiments, it may be between approximately 0.5 and 1.5. Likewise, y may be any value, integer or non-integer, between approximately 1 and 100; in certain embodiments, it may be an integer or non-integer value between approximately 1 and 10. In some embodiments, x and y may have values so as to be in a non-stoichiometric ratio. It is noted that any IFL materials written as stoichiometric formulations in the present disclosure may also exist in non-stoichiometric formulations such as examples described above.

In some embodiments, the IFL may comprise a titanate. A titanate according to some embodiments may be of the general formula $M'TiO_3$, where M' comprises any 2+ cation. In some embodiments, M' may comprise a cationic form of Be, Mg, Ca, Sr, Ba, Ni, Zn, Cd, Hg, Cu, Pd, Pt, Sn, or Pb. In some embodiments, the IFL may comprise a single species of titanate, which in other embodiments, the IFL may comprise two or more different species of titanates. In one embodiment, the titanate has the formula $SrTiO_3$. In another embodiment, the titanate may have the formula $BaTiO_3$. In yet another embodiment, the titanate may have the formula $CaTiO_3$.

By way of explanation, and without implying any limitation, titanates have a perovskite crystalline structure and strongly seed the perovskite material (e.g., methylammonium lead iodide ($MAPbI_3$), and formamidinium lead iodide ($FAPbI_3$)) growth conversion process. Titanates generally also meet other IFL requirements, such as ferroelectric behavior, sufficient charge carrier mobility, optical transparency, matched energy levels, and high dielectric constant.

In other embodiments, the IFL may comprise a zirconate. A zirconate according to some embodiments may be of the general formula $M'ZrO_3$, where M' comprises any 2+ cation. In some embodiments, M' may comprise a cationic form of Be, Mg, Ca, Sr, Ba, Ni, Zn, Cd, Hg, Cu, Pd, Pt, Sn, or Pb. In some embodiments, the IFL may comprise a single species of zirconate, which in other embodiments, the IFL may comprise two or more different species of zirconate. In one embodiment, the zirconate has the formula $SrZrO_3$. In another embodiment, the zirconate may have the formula $BaZrO_3$. In yet another embodiment, the zirconate may have the formula $CaZrO_3$.

By way of explanation, and without implying any limitation, zirconates have a perovskite crystalline structure and strongly seed the perovskite material (e.g., $MAPbI_3$, $FAPbI_3$) growth conversion process. Zirconates generally also meet other IFL requirements, such as ferroelectric behavior, sufficient charge carrier mobility, optical transparency, matched energy levels, and high dielectric constant.

In other embodiments, the IFL may comprise a stannate. A stannate according to some embodiments may be of the general formula $M'SnO_3$, or $M'_2SnO_4$ where M' comprises any 2+ cation. In some embodiments, M' may comprise a cationic form of Be, Mg, Ca, Sr, Ba, Ni, Zn, Cd, Hg, Cu, Pd, Pt, Sn, or Pb. In some embodiments, the IFL may comprise a single species of stannate, which in other embodiments, the IFL may comprise two or more different species of stannate. In one embodiment, the stannate has the formula $SrSnO_3$. In another embodiment, the stannate may have the formula $BaSnO_3$. In yet another embodiment, the stannate may have the formula $CaSnO_3$.

By way of explanation, and without implying any limitation, stannates have a perovskite crystalline structure and strongly seed the perovskite material (e.g., $MAPbI_3$, $FAPbI_3$) growth conversion process. Stannates generally also meet other IFL requirements, such as ferroelectric behavior, sufficient charge carrier mobility, optical transparency, matched energy levels, and high dielectric constant.

In other embodiments, the IFL may comprise a plumbate. A plumbate according to some embodiments may be of the general formula $M'PbO_3$, where M' comprises any 2+ cation. In some embodiments, M' may comprise a cationic form of Be, Mg, Ca, Sr, Ba, Ni, Zn, Cd, Hg, Cu, Pd, Pt, Sn, or Pb. In some embodiments, the IFL may comprise a single species of plumbate, which in other embodiments, the IFL may comprise two or more different species of plumbate. In one embodiment, the plumbate has the formula $SrPbO_3$. In another embodiment, the plumbate may have the formula $BaPbO_3$. In yet another embodiment, the plumbate may have the formula $CaPbO_3$. In yet another embodiment, the plumbate may have the formula $Pb^{II}Pb^{IV}O_3$.

By way of explanation, and without implying any limitation, plumbates have a perovskite crystalline structure and strongly seed the perovskite material (e.g., $MAPbI_3$, $FAPbI_3$) growth conversion process. Plumbates generally also meet other IFL requirements, such as ferroelectric behavior, sufficient charge carrier mobility, optical transparency, matched energy levels, and high dielectric constant.

Further, in other embodiments, an IFL may comprise a combination of a zirconate and a titanate in the general formula $M'[Zr_xTi_{1-x}]O_3$, where X is greater than 0 but less than one 1, and M' comprises any 2+ cation. In some embodiments, M' may comprise a cationic form of Be, Mg, Ca, Sr, Ba, Ni, Zn, Cd, Hg, Cu, Pd, Pt, Sn, or Pb. In some embodiments, the IFL may comprise a single species of zirconate, which in other embodiments, the IFL may comprise two or more different species of zirconate. In one embodiment, the zirconate/titanate combination has the formula $Pb[Zr_xTi_{1-x}]O_3$. In another embodiment, the zirconate/titanate combination has the formula $Pb[Zr_{0.52}Ti_{0.48}]O_3$.

By way of explanation, and without implying any limitation, a zirconate/titanate combination have a perovskite crystalline structure and strongly seed the perovskite material (e.g., $MAPbI_3$, FAPbI3) growth conversion process. Zirconate/titanate combinations generally also meet other IFL requirements, such as ferroelectric behavior, sufficient charge carrier mobility, optical transparency, matched energy levels, and high dielectric constant.

In other embodiments, the IFL may comprise a niobate. A niobate according to some embodiments may be of the general formula $M'NbO_3$, where: M' comprises any 1+ cation. In some embodiments, M' may comprise a cationic form of Li, Na, K, Rb, Cs, Cu, Ag, Au, Tl, ammonium, or H. In some embodiments, the IFL may comprise a single species of niobate, which in other embodiments, the IFL may comprise two or more different species of niobate. In one embodiment, the niobate has the formula $LiNbO_3$. In another embodiment, the niobate may have the formula $NaNbO_3$. In yet another embodiment, the niobate may have the formula $AgNbO_3$.

By way of explanation, and without implying any limitation, niobates generally meet IFL requirements, such as piezoelectric behavior, non-linear optical polarizability, photoelasticity, ferroelectric behavior, Pockels effect, sufficient charge carrier mobility, optical transparency, matched energy levels, and high dielectric constant.

In one embodiment, a perovskite material device may be formulated by casting $PbI_2$ onto a $SrTiO_3$-coated ITO substrate. The $PbI_2$ may be converted to $MAPbI_3$ by a dipping process. This process is described in greater detail below. This resulting conversion of $PbI_2$ to $MAPbI_3$ is more complete (as observed by optical spectroscopy) as compared to the preparation of the substrate without $SrTiO_3$.

Any interfacial material discussed herein may further comprise doped compositions. To modify the characteristics (e.g., electrical, optical, mechanical) of an interfacial material, a stoichiometric or non-stoichiometric material may be doped with one or more elements (e.g., Na, Y, Mg, N, P) in amounts ranging from as little as 1 ppb to 50 mol %. Some examples of interfacial materials include: NiO, $TiO_2$, $SrTiO_3$, $Al_2O_3$, $ZrO_2$, $WO_3$, $V_2O_5$, $MO_3$, ZnO, graphene, and carbon black. Examples of possible dopants for these interfacial materials include: Li, Na, Be, Mg, Ca, Sr, Ba, Sc, Y, Nb, Ti, Fe, Co, Ni, Cu, Ga, Sn, In, B, N, P, C, S, As, a halide, a pseudohalide (e.g., cyanide, cyanate, isocyanate, fulminate, thiocyanate, isothiocyanate, azide, tetracarbonylcobaltate, carbamoyldicyanomethanide, dicyanonitrosomethanide, dicyanamide, and tricyanomethanide), and Al in any of its oxidation states. References herein to doped interfacial materials are not intended to limit the ratios of component elements in interfacial material compounds.

In some embodiments, multiple IFLs made from different materials may be arranged adjacent to each other to form a composite IFL. This configuration may involve two different IFLs, three different IFLs, or an even greater number of different IFLs. The resulting multi-layer IFL or composite IFL may be used in lieu of a single-material IFL. For example, a composite IFL may be used any IFL shown in the example of FIG. 2, such as IFL 3903, IFL 3905, IFL 3907, IFL 3909, or IFL 3911. While the composite IFL differs from a single-material IFL, the assembly of a perovskite material PV cell having multi-layer IFLs is not substantially different than the assembly of a perovskite material PV cell having only single-material IFLs.

Generally, the composite IFL may be made using any of the materials discussed herein as suitable for an IFL. In one embodiment, the IFL comprises a layer of $Al_2O_3$ and a layer of ZnO or M:ZnO (doped ZnO, e.g., Be:ZnO, Mg:ZnO, Ca:ZnO, Sr:ZnO, Ba:ZnO, Sc:ZnO, Y:ZnO, Nb:ZnO). In an embodiment, the IFL comprises a layer of $ZrO_2$ and a layer of ZnO or M:ZnO. In certain embodiments, the IFL comprises multiple layers. In some embodiments, a multi-layer IFL generally has a conductor layer, a dielectric layer, and a semi-conductor layer. In particular embodiments the layers may repeat, for example, a conductor layer, a dielectric layer, a semi-conductor layer, a dielectric layer, and a semi-conductor layer. Examples of multi-layer IFLs include an IFL having an ITO layer, an $Al_2O_3$ layer, a ZnO layer, and a second $Al_2O_3$ layer; an IFL having an ITO layer, an $Al_2O_3$ layer, a ZnO layer, a second $Al_2O_3$ layer, and a second ZnO layer; an IFL having an ITO layer, an $Al_2O_3$ layer, a ZnO layer, a second Al$_2$O$_3$ layer, a second ZnO layer, and a third Al$_2$O$_3$ layer; and IFLs having as many layers as necessary to achieve the desired performance characteristics. As discussed previously, references to certain stoichiometric ratios are not intended to limit the ratios of component elements in IFL layers according to various embodiments.

Arranging two or more adjacent IFLs as a composite IFL may outperform a single IFL in perovskite material PV cells where attributes from each IFL material may be leveraged in a single IFL. For example, in the architecture having an ITO layer, an Al$_2$O$_3$ layer, and a ZnO layer, where ITO is a conducting electrode, Al$_2$O$_3$ is a dielectric material and ZnO is a n-type semiconductor, ZnO acts as an electron acceptor with well performing electron transport properties (e.g., mobility). Additionally, Al$_2$O$_3$ is a physically robust material that adheres well to ITO, homogenizes the surface by capping surface defects (e.g., charge traps), and improves device diode characteristics through suppression of dark current.

Additionally, some perovskite material PV cells may include so called "tandem" PV cells having more than one perovskite photoactive layer. For example, both photoactive materials 3908 and 3906 of FIG. 2 may be perovskite materials. In such tandem PV cells an interfacial layer between the two photoactive layers, such as IFL 3907 (i.e., a recombination layer) of FIG. 2 may comprise a multilayer, or composite, IFL. In some embodiments, the layers sandwiched between the two photoactive layers of a tandem PV device may include an electrode layer.

A tandem PV device may include the following layers, listed in order from either top to bottom or bottom to top: a first substrate, a first electrode, a first interfacial layer, a first perovskite material, a second interfacial layer, a second electrode, a third interfacial layer, a second perovskite material, a fourth interfacial layer, and a third electrode. In some embodiments, the first and third interfacial layers may be hole transporting interfacial layers and the second and fourth interfacial layers may be electron transporting interfacial layers. In other embodiments, the first and third interfacial layers may be electron transporting interfacial layers and the second and fourth interfacial layers may be hole transporting interfacial layers. In yet other embodiments, the first and fourth interfacial layers may be hole transporting interfacial layers and the second and third interfacial layers may be electron transporting interfacial layers. In other embodiments, the first and fourth interfacial layers may be electron transporting interfacial layers and the second and third interfacial layers may be hole transporting interfacial layers. In tandem PV devices the first and second perovskite materials may have different band gaps. In some embodiments, the first perovskite material may be formamidinium lead bromide (FAPbBr$_3$) and the second perovskite material may be formamidinium lead iodide (FAPbI$_3$). In other embodiments, the first perovskite material may be methylammonium lead bromide (MAPbBr$_3$) and the second perovskite material may be formamidinium lead iodide (FAPbI$_3$). In other embodiments, the first perovskite material may be methylammonium lead bromide (MAPbBr$_3$) and the second perovskite material may be methylammonium lead iodide (MAPbI$_3$).

Perovskite Material

A perovskite material may be incorporated into one or more aspects of a PV or other device. A perovskite material according to some embodiments may be of the general formula $C_wM_yX_z$, where: C comprises one or more cations (e.g., an amine, ammonium, phosphonium, a Group 1 metal, a Group 2 metal, and/or other cations or cation-like compounds); M comprises one or more metals (examples including Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr); X comprises one or more anions; and w, y, and z represent real numbers between 1 and 20. In some embodiments, C may include one or more organic cations. In some embodiments, each organic cation C may be larger than each metal M, and each anion X may be capable of bonding with both a cation C and a metal M. In particular embodiments, a perovskite material may be of the formula $CMX_3$.

In certain embodiments, C may include an ammonium, an organic cation of the general formula $[NR_4]^+$ where the R groups may be the same or different groups. Suitable R groups include, but are not limited to: hydrogen, methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenl, alkoxyphenyl, pyridine, naphthalene); cyclic complexes where at least one nitrogen is contained within the ring (e.g., pyridine, pyrrole, pyrrolidine, piperidine, tetrahydroquinoline); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (e.g., acetic acid, propanoic acid); and ester or amide derivatives thereof; any amino acid (e.g., glycine, cysteine, proline, glutamic acid, arginine, serine, histidine, 5-ammoniumvaleric acid) including alpha, beta, gamma, and greater derivatives; any silicon containing group (e.g., siloxane); and any alkoxy or group, —OCxHy, where x=0-20, y=1-42.

In certain embodiments, C may include a formamidinium, an organic cation of the general formula $[R_2NCRNR_2]^+$ where the R groups may be the same or different groups. Suitable R groups include, but are not limited to: hydrogen, methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenl, alkoxyphenyl, pyridine, naphthalene); cyclic complexes where at least one nitrogen is contained within the ring (e.g., imidazole, benzimidazole, pyrimidine, (azolidinylidenemethyl)pyrrolidine, triazole); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (acetic acid, propanoic acid) and ester or amide derivatives thereof; any amino acid (e.g., glycine, cysteine, proline, glutamic acid, arginine, serine, histidine, 5-ammoniumvaleric acid) including alpha, beta, gamma, and greater derivatives; any silicon containing group (e.g., siloxane); and any alkoxy or group, —OCxHy, where x=0-20, y=1-42.

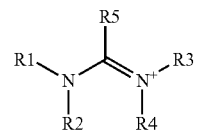

Formula 1

Formula 1 illustrates the structure of a formamidinium cation having the general formula of $[R_2NCRNR_2]^+$ as described above. Formula 2 illustrates examples structures of several formamidinium cations that may serve as a cation "C" in a perovskite material.

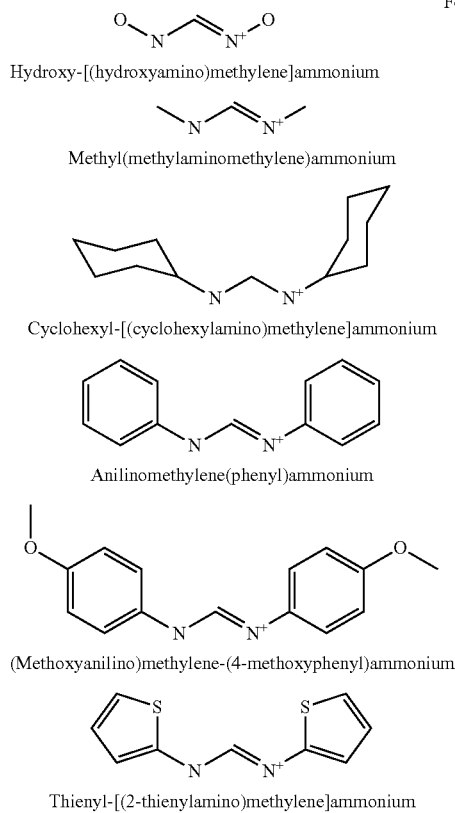

Formula 2

Hydroxy-[(hydroxyamino)methylene]ammonium

Methyl(methylaminomethylene)ammonium

Cyclohexyl-[(cyclohexylamino)methylene]ammonium

Anilinomethylene(phenyl)ammonium (Methoxyanilino)methylene-(4-methoxyphenyl)ammonium Thienyl-[(2-thienylamino)methylene]ammonium In certain embodiments, C may include a guanidinium, an organic cation of the general formula $[(R_2N)_2C=NR_2]^+$ where the R groups may be the same or different groups. Suitable R groups include, but are not limited to: hydrogen, methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenyl, alkoxyphenyl, pyridine, naphthalene); cyclic complexes where at least one nitrogen is contained within the ring (e.g., octahydropyrimido[1,2-a]pyrimidine, pyrimido[1,2-a]pyrimidine, hexahydroimidazo[1,2-a]imidazole, hexahydropyrimidin-2-imine); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (acetic acid, propanoic acid) and ester or amide derivatives thereof; any amino acid (e.g., glycine, cysteine, proline, glutamic acid, arginine, serine, histidine, 5-ammoniumvaleric acid) including alpha, beta, gamma, and greater derivatives; any silicon containing group (e.g., siloxane); and any alkoxy or group, —OCxHy, where x=0-20, y=1-42.

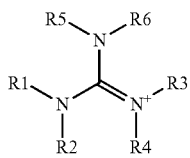

Formula 3

Formula 3 illustrates the structure of a guanidinium cation having the general formula of $[(R_2N)_2C=NR_2]^+$ as described above. Formula 4 illustrates examples of structures of several guanidinium cations that may serve as a cation "C" in a perovskite material.

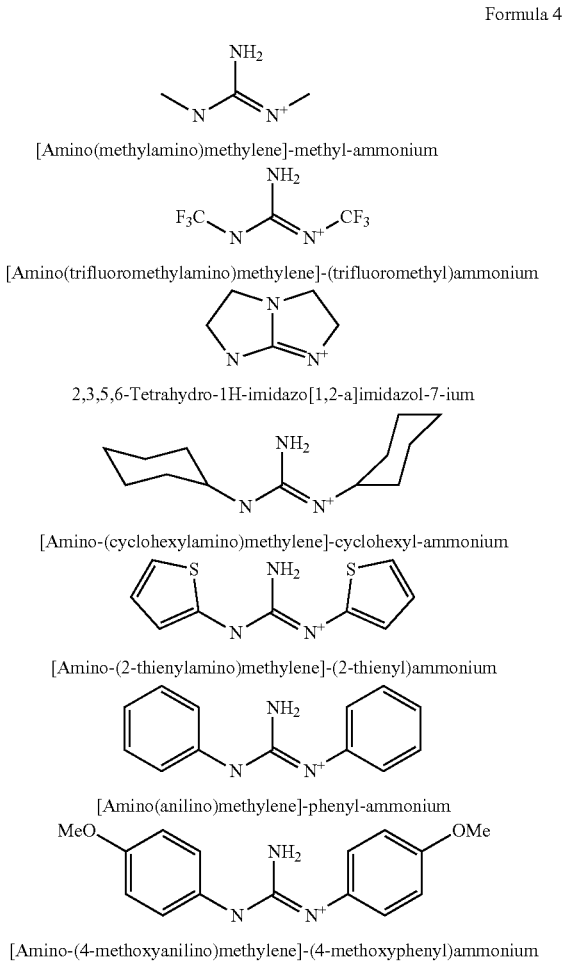

Formula 4

[Amino(methylamino)methylene]-methyl-ammonium

[Amino(trifluoromethylamino)methylene]-(trifluoromethyl)ammonium 2,3,5,6-Tetrahydro-1H-imidazo[1,2-a]imidazol-7-ium

[Amino-(cyclohexylamino)methylene]-cyclohexyl-ammonium

[Amino-(2-thienylamino)methylene]-(2-thienyl)ammonium

[Amino(anilino)methylene]-phenyl-ammonium

[Amino-(4-methoxyanilino)methylene]-(4-methoxyphenyl)ammonium

In certain embodiments, C may include an ethene tetramine cation, an organic cation of the general formula $[(R_2N)_2C=C(NR_2)_2]^+$ where the R groups may be the same or different groups. Suitable R groups include, but are not limited to: hydrogen, methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenl, alkoxyphenyl, pyridine, naphthalene); cyclic complexes where at least one nitrogen is contained within the ring (e.g., 2-hexahydropyrimidin-2-ylidenehexahydropyrimidine, octahydropyrazino[2,3-b]pyrazine, pyrazino[2, 3-b]pyrazine, quinoxalino[2,3-b]quinoxaline); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (acetic acid, propanoic acid) and ester or amide derivatives thereof; any amino acid (e.g., glycine, cysteine, proline, glutamic acid, arginine, serine, histidine, 5-ammoniumvaleric acid) including alpha, beta, gamma, and greater derivatives; any silicon containing group (e.g., siloxane); and any alkoxy or group, —OCxHy, where x=0-20, y=1-42.

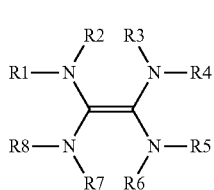

Formula 5

Formula 5 illustrates the structure of an ethene tetramine cation having the general formula of $[(R_2N)_2C=C(NR_2)_2]^+$ as described above. Formula 6 illustrates examples of structures of several ethene tetramine ions that may serve as a cation "C" in a perovskite material.

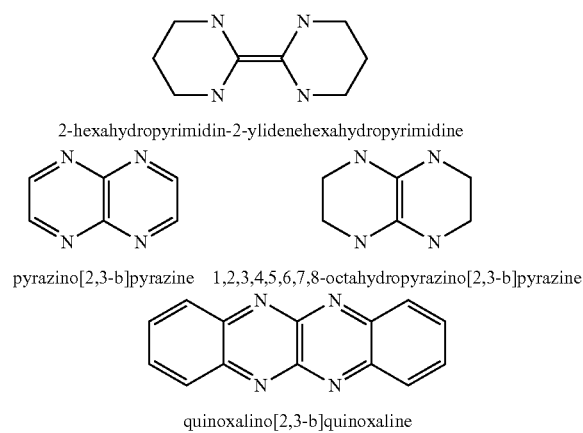

Formula 6

2-hexahydropyrimidin-2-ylidenehexahydropyrimidine pyrazino[2,3-b]pyrazine  1,2,3,4,5,6,7,8-octahydropyrazino[2,3-b]pyrazine quinoxalino[2,3-b]quinoxaline In certain embodiments, C may include an imidazolium cation, an aromatic, cyclic organic cation of the general formula [CRNRCRNRCR]$^+$ where the R groups may be the same or different groups. Suitable R groups may include, but are not limited to: hydrogen, methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenyl, alkoxyphenyl, pyridine, naphthalene); cyclic complexes where at least one nitrogen is contained within the ring (e.g., 2-hexahydropyrimidin-2-ylidenehexahydropyrimidine, octahydropyrazino[2,3-b]pyrazine, pyrazino[2,3-b]pyrazine, quinoxalino[2,3-b]quinoxaline); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (acetic acid, propanoic acid) and ester or amide derivatives thereof; any amino acid (e.g., glycine, cysteine, proline, glutamic acid, arginine, serine, histidine, 5-ammoniumvaleric acid) including alpha, beta, gamma, and greater derivatives; any silicon containing group (e.g., siloxane); and any alkoxy or group, —OCxHy, where x=0-20, y=1-42.

In certain embodiments, C may include a pyridium cation, an aromatic, cyclic organic cation of the general formula [CRCRCRCRCRNR]$^+$ where the R groups may be the same or different groups. Suitable R groups may include, but are not limited to: hydrogen, methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenyl, alkoxyphenyl, pyridine, naphthalene); cyclic complexes where at least one nitrogen is contained within the ring (e.g., 2-hexahydropyrimidin-2-ylidenehexahydropyrimidine, octahydropyrazino[2,3-b]pyrazine, pyrazino[2,3-b]pyrazine, quinoxalino[2,3-b]quinoxaline); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (acetic acid, propanoic acid) and ester or amide derivatives thereof; any amino acid (e.g., glycine, cysteine, proline, glutamic acid, arginine, serine, histidine, 5-ammoniumvaleric acid) including alpha, beta, gamma, and greater derivatives; any silicon containing group (e.g., siloxane); and any alkoxy or group, -OCxHy, where x=0-20, y=1-42.

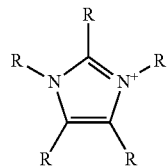

Formula 7

In some embodiments, X may include one or more halides. In certain embodiments, X may instead or in addition include a Group 16 anion. In certain embodiments, the Group 16 anion may be oxide, sulfide, selenide, or telluride. In certain embodiments, X may instead or in addition include one or more a pseudohalides (e.g., cyanide, cyanate, isocyanate, fulminate, thiocyanate, isothiocyanate, azide, tetracarbonylcobaltate, carbamoyldicyanomethanide, dicyanonitrosomethanide, dicyanamide, and tricyanomethanide).

In one embodiment, a perovskite material may comprise the empirical formula $CMX_3$ where: C comprises one or more of the aforementioned cations, a Group 1 metal, a Group 2 metal, and/or other cations or cation-like compounds; M comprises one or more metals (examples including Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr); and X comprises one or more of the aforementioned anions.

In another embodiment, a perovskite material may comprise the empirical formula $C'M_2X_6$ where: C' comprises a cation with a 2+ charge including one or more of the aforementioned cations, diammonium butane, a Group 1 metal, a Group 2 metal, and/or other cations or cation-like compounds; M comprises one or more metals (examples including Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr); and X comprises one or more of the aforementioned anions.

In another embodiment, a perovskite material may comprise the empirical formula C'MX$_4$ where: C' comprises a cation with a 2+ charge including one or more of the aforementioned cations, diammonium butane, a Group 1 metal, a Group 2 metal, and/or other cations or cation-like compounds; M comprises one or more metals (examples including Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr); and X comprises one or more of the aforementioned anions. In such an embodiment, the perovskite material may have a 2D structure.

In one embodiment, a perovskite material may comprise the empirical formula $C_3M_2X_9$ where: C comprises one or more of the aforementioned cations, a Group 1 metal, a Group 2 metal, and/or other cations or cation-like compounds; M comprises one or more metals (examples including Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr); and X comprises one or more of the aforementioned anions.

In one embodiment, a perovskite material may comprise the empirical formula $CM_2X_7$ where: C comprises one or more of the aforementioned cations, a Group 1 metal, a Group 2 metal, and/or other cations or cation-like compounds; M comprises one or more metals (examples including Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr n); and X comprises one or more of the aforementioned anions.

In one embodiment, a perovskite material may comprise the empirical formula $C_2MX_4$ where: C comprises one or more of the aforementioned cations, a Group 1 metal, a Group 2 metal, and/or other cations or cation-like compounds; M comprises one or more metals (examples including Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr); and X comprises one or more of the aforementioned anions.

Perovskite materials may also comprise mixed ion formulations where C, M, or X comprise two or more species, for example, $Cs_{0.1}FA_{0.9}Pb(I_{0.9}Cl_{0.1})_3$; $Rb_{0.1}FA_{0.9}Pb(I_{0.9}Cl_{0.1})_3$ $Cs_{0.1}FA_{0.9}PbI_3$; $FAPb_{0.5}Sn_{0.5}I_3$; $FA_{0.83}Cs_{0.17}Pb(I_{0.6}Br_{0.4})_3$; $FA_{0.83}Cs_{0.12}Rb_{0.05}Pb(I_{0.6}Br_{0.4})_3$ and $FA_{0.85}MA_{0.15}Pb(I_{0.85}Br_{0.15})_3$.

Composite Perovskite Material Device Design

In some embodiments, the present disclosure may provide composite design of PV and other similar devices (e.g., batteries, hybrid PV batteries, FETs, LEDs, nonlinear optics (NLOs), waveguides, etc.) including one or more perovskite materials. For example, one or more perovskite materials may serve as either or both of first and second active material of some embodiments (e.g., active materials 3906a and 3908a of FIG. 3). In more general terms, some embodiments of the present disclosure provide PV or other devices having an active layer comprising one or more perovskite materials. In such embodiments, perovskite material (that is, material including any one or more perovskite materials(s)) may be employed in active layers of various architectures. Furthermore, perovskite material may serve the function(s) of any one or more components of an active layer (e.g., charge transport material, mesoporous material, photoactive material, and/or interfacial material, each of which is discussed in greater detail below). In some embodiments, the same perovskite materials may serve multiple such functions, although in other embodiments, a plurality of perovskite materials may be included in a device, each perovskite material serving one or more such functions. In certain embodiments, whatever role a perovskite material may serve, it may be prepared and/or present in a device in various states. For example, it may be substantially solid in some embodiments. A solution or suspension may be coated or otherwise deposited within a device (e.g., on another component of the device such as a mesoporous, interfacial, charge transport, photoactive, or other layer, and/or on an electrode). Perovskite materials in some embodiments may be formed in situ on a surface of another component of a device (e.g., by vapor deposition as a thin-film solid). Any other suitable means of forming a layer comprising perovskite material may be employed.

In general, a perovskite material device may include a first electrode, a second electrode, and an active layer comprising a perovskite material, the active layer disposed at least partially between the first and second electrodes. In some embodiments, the first electrode may be one of an anode and a cathode, and the second electrode may be the other of an anode and cathode. An active layer according to certain embodiments may include any one or more active layer components, including any one or more of: charge transport material; liquid electrolyte; mesoporous material; photoactive material (e.g., a dye, silicon, cadmium telluride, cadmium sulfide, cadmium selenide, copper indium gallium selenide, gallium arsenide, germanium indium phosphide, semiconducting polymers, other photoactive materials)); and interfacial material. Any one or more of these active layer components may include one or more perovskite materials. In some embodiments, some or all of the active layer components may be in whole or in part arranged in sub-layers. For example, the active layer may comprise any one or more of: an interfacial layer including interfacial material; a mesoporous layer including mesoporous material; and a charge transport layer including charge transport material. Further, an interfacial layer may be included between any two or more other layers of an active layer according to some embodiments and/or between an active layer component and an electrode. Reference to layers herein may include either a final arrangement (e.g., substantially discrete portions of each material separately definable within the device), and/or reference to a layer may mean arrangement during construction of a device, notwithstanding the possibility of subsequent intermixing of material(s) in each layer. Layers may in some embodiments be discrete and comprise substantially contiguous material (e.g., layers may be as stylistically illustrated in FIG. 2).

In some embodiments, a perovskite material device may be a field effect transistor (FET). An FET perovskite material device may include a source electrode, drain electrode, gate electrode, dielectric layer, and a semiconductor layer. In some embodiments the semiconductor layer of an FET perovskite material device may be a perovskite material.

A perovskite material device according to some embodiments may optionally include one or more substrates. In some embodiments, either or both of the first and second electrode may be coated or otherwise disposed upon a substrate, such that the electrode is disposed substantially between a substrate and the active layer. The materials of composition of devices (e.g., substrate, electrode, active layer and/or active layer components) may in whole or in part be either rigid or flexible in various embodiments. In some embodiments, an electrode may act as a substrate, thereby negating the need for a separate substrate.

Furthermore, a perovskite material device according to certain embodiments may optionally include an anti-reflective layer or anti-reflective coating (ARC). In addition, a perovskite material device may include any one or more additives, such as any one or more of the additives discussed above with respect to some embodiments of the present disclosure.

Figure 2:
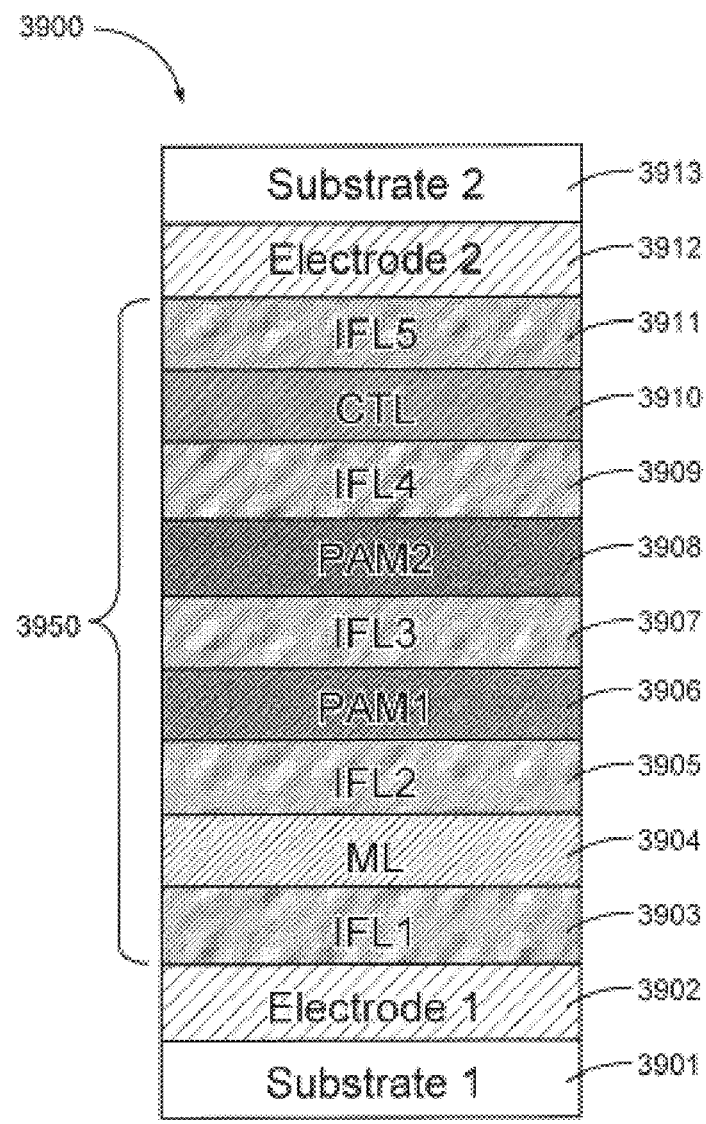
FIG. 2 is a stylized diagram showing components of an example PV device, according to some embodiments of the present disclosure.

Description of some of the various materials that may be included in a perovskite material device will be made in part with reference to FIG. 2. FIG. 2 is a stylized diagram of a perovskite material device 3900 according to some embodiments. Although various components of the device 3900 are illustrated as discrete layers comprising contiguous material, it should be understood that FIG. 2 is a stylized diagram; thus, embodiments in accordance with it may include such discrete layers, and/or substantially intermixed, non-contiguous layers, consistent with the usage of "layers" previously discussed herein. The device 3900 includes first and second substrates 3901 and 3913. A first electrode 3902 is disposed upon an inner surface of the first substrate 3901, and a second electrode 3912 is disposed on an inner surface of the second substrate 3913. An active layer 3950 is sandwiched between the two electrodes 3902 and 3912. The active layer 3950 includes a mesoporous layer 3904; first and second photoactive materials 3906 and 3908; a charge transport layer 3910, and several interfacial layers. FIG. 2 furthermore illustrates an example device 3900 according to embodiments wherein sub-layers of the active layer 3950 are separated by the interfacial layers, and further wherein interfacial layers are disposed upon each electrode 3902 and 3912. In particular, second, third, and fourth interfacial layers 3905, 3907, and 3909 are respectively disposed between each of the mesoporous layer 3904, first photoactive material 3906, second photoactive material 3908, and charge transport layer 3910. First and fifth interfacial layers 3903 and 3911 are respectively disposed between (i) the first electrode 3902 and mesoporous layer 3904; and (ii) the charge transport layer 3910 and second electrode 3912. Thus, the architecture of the example device depicted in FIG. 2 may be characterized as: substrate—electrode—active layer—electrode—substrate. The architecture of the active layer 3950 may be characterized as: interfacial layer—mesoporous layer—interfacial layer—photoactive material—interfacial layer—photoactive material—interfacial layer—charge transport layer—interfacial layer. As noted previously, in some embodiments, interfacial layers need not be present; or, one or more interfacial layers may be included only between certain, but not all, components of an active layer and/or components of a device.

A substrate, such as either or both of first and second substrates 3901 and 3913, may be flexible or rigid. If two substrates are included, at least one should be transparent or translucent to electromagnetic (EM) radiation (such as, e.g., UV, visible, or IR radiation). If one substrate is included, it may be similarly transparent or translucent, although it need not be, so long as a portion of the device permits EM radiation to contact the active layer 3950. Suitable substrate materials include any one or more of: glass; sapphire; magnesium oxide (MgO); mica; polymers (e.g., PEN, PET, PEG, polyolefin, polypropylene, polyethylene, polycarbonate, PMMA, polyamide, vinyl, Kapton); ceramics; carbon; composites (e.g., fiberglass, Kevlar; carbon fiber); fabrics (e.g., cotton, nylon, silk, wool); wood; drywall; tiles (e.g. ceramic, composite, or clay); metal; steel; silver; gold; aluminum; magnesium; concrete; and combinations thereof.

As previously noted, an electrode (e.g., one of electrodes 3902 and 3912 of FIG. 2) may be either an anode or a cathode. In some embodiments, one electrode may function as a cathode, and the other may function as an anode. Either or both electrodes 3902 and 3912 may be coupled to leads, cables, wires, or other means enabling charge transport to and/or from the device 3900. An electrode may constitute any conductive material, and at least one electrode should be transparent or translucent to EM radiation, and/or be arranged in a manner that allows EM radiation to contact at least a portion of the active layer 3950. Suitable electrode materials may include any one or more of: indium tin oxide or tin-doped indium oxide (ITO); fluorine-doped tin oxide (FTO); cadmium oxide (CdO); zinc indium tin oxide (ZITO); aluminum zinc oxide (AZO); aluminum (Al); gold (Au); silver (Ag); calcium (Ca); chromium (Cr); copper (Cu); magnesium (Mg); titanium (Ti); steel; carbon (and allotropes thereof); doped carbon (e.g., nitrogen-doped); nanoparticles in core-shell configurations (e.g., silicon-carbon core-shell structure); and combinations thereof.

Mesoporous material (e.g., the material included in mesoporous layer 3904 of FIG. 2) may include any pore-containing material. In some embodiments, the pores may have diameters ranging from about 1 to about 100 nm; in other embodiments, pore diameter may range from about 2 to about 50 nm. Suitable mesoporous material includes any one or more of: any interfacial material and/or mesoporous material discussed elsewhere herein; aluminum (Al); bismuth (Bi); cerium (Ce); hafnium (Hf); indium (In); molybdenum (Mo); niobium (Nb); nickel (Ni); silicon (Si); titanium (Ti); vanadium (V); zinc (Zn); zirconium (Zr); an oxide of any one or more of the foregoing metals (e.g., alumina, ceria, titania, zinc oxide, zirconia, etc.); a sulfide of any one or more of the foregoing metals; a nitride of any one or more of the foregoing metals; and combinations thereof. In some embodiments, any material disclosed herein as an IFL may be a mesoporous material. In other embodiments, the device illustrated by FIG. 2 may not include a mesoporous material layer and include only thin-film, or "compact," IFLs that are not mesoporous.

Photoactive material (e.g., first or second photoactive material 3906 or 3908 of FIG. 2) may comprise any photoactive compound, such as any one or more of silicon (for example, polycrystalline silicon, single-crystalline silicon, or amorphous silicon), cadmium telluride, cadmium sulfide, cadmium selenide, copper indium gallium selenide, copper indium selenide, copper zinc tin sulfide, gallium arsenide, germanium, germanium indium phosphide, indium phosphide, one or more semiconducting polymers (e.g., polythiophenes (e.g., poly(3-hexylthiophene) and derivatives thereof, or P3HT); carbazole-based copolymers such as polyheptadecanylcarbazole dithienylbenzothiadiazole and derivatives thereof (e.g., PCDTBT); other copolymers such as polycyclopentadithiophene—benzothiadiazole and derivatives thereof (e.g., PCPDTBT), polybenzodithiophenyl-thienothiophenediyl and derivatives thereof (e.g., PTB6, PTB7, PTB7-th, PCE-10); poly(triaryl amine) compounds and derivatives thereof (e.g., PTAA); polyphenylene vinylenes and derivatives thereof (e.g., MDMO-PPV, MEH-PPV), and combinations thereof.

In certain embodiments, photoactive material may instead or in addition comprise a dye (e.g., N719, N3, other ruthenium-based dyes). In some embodiments, a dye (of whatever composition) may be coated onto another layer (e.g., a mesoporous layer and/or an interfacial layer). In some embodiments, photoactive material may include one or more perovskite materials. Perovskite-material-containing photoactive substance may be of a solid form, or in some embodiments it may take the form of a dye that includes a suspension or solution comprising perovskite material. Such a solution or suspension may be coated onto other device components in a manner similar to other dyes. In some embodiments, solid perovskite-containing material may be deposited by any suitable means (e.g., vapor deposition, solution deposition, direct placement of solid material). Devices according to various embodiments may include one, two, three, or more photoactive compounds (e.g., one, two, three, or more perovskite materials, dyes, or combinations thereof). In certain embodiments including multiple dyes or other photoactive materials, each of the two or more dyes or other photoactive materials may be separated by one or more interfacial layers. In some embodiments, multiple dyes and/or photoactive compounds may be at least in part intermixed.

Charge transport material (e.g., charge transport material of charge transport layer 3910 in FIG. 2) may include solid-state charge transport material (i.e., a colloquially labeled solid-state electrolyte), or it may include a liquid electrolyte and/or ionic liquid. Any of the liquid electrolyte, ionic liquid, and solid-state charge transport material may be referred to as charge transport material. As used herein, "charge transport material" refers to any material, solid, liquid, or otherwise, capable of collecting charge carriers and/or transporting charge carriers. For instance, in PV devices according to some embodiments, a charge transport material may be capable of transporting charge carriers to an electrode. Charge carriers may include holes (the transport of which could make the charge transport material just as properly labeled "hole transport material") and electrons. Holes may be transported toward an anode, and electrons toward a cathode, depending upon placement of the charge transport material in relation to either a cathode or anode in a PV or other device. Suitable examples of charge transport material according to some embodiments may include any one or more of: perovskite material; $I^-/I_3^-$; Co complexes; polythiophenes (e.g., poly(3-hexylthiophene) and derivatives thereof, or P3HT); carbazole-based copolymers such as polyheptadecanylcarbazole dithienylbenzothiadiazole and derivatives thereof (e.g., PCDTBT); other copolymers such as polycyclopentadithiophene—benzothiadiazole and derivatives thereof (e.g., PCPDTBT), polybenzodithiophenyl-thienothiophenediyl and derivatives thereof (e.g., PTB6, PTB7, PTB7-th, PCE-10); poly(triaryl amine) compounds and derivatives thereof (e.g., PTAA); Spiro-OMeTAD; polyphenylene vinylenes and derivatives thereof (e.g., MDMO-PPV, MEH-PPV); fullerenes and/or fullerene derivatives (e.g., C60, PCBM); carbon nanotubes; graphite; graphene; carbon black; amorphous carbon; glassy carbon; carbon fiber; and combinations thereof. In certain embodiments, charge transport material may include any material, solid or liquid, capable of collecting charge carriers (electrons or holes), and/or capable of transporting charge carriers. Charge transport material of some embodiments therefore may be n- or p-type active, ambipolar, and/or intrinsic semi-conducting material. Charge transport material may be disposed proximate to one of the electrodes of a device. It may in some embodiments be disposed adjacent to an electrode, although in other embodiments an interfacial layer may be disposed between the charge transport material and an electrode (as shown, e.g., in FIG. 2 with the fifth interfacial layer 3911). In certain embodiments, the type of charge transport material may be selected based upon the electrode to which it is proximate. For example, if the charge transport material collects and/or transports holes, it may be proximate to an anode so as to transport holes to the anode. However, the charge transport material may instead be placed proximate to a cathode and be selected or constructed so as to transport electrons to the cathode.

As previously noted, devices according to various embodiments may optionally include an interfacial layer between any two other layers and/or materials, although devices according to some embodiments need not contain any interfacial layers. Thus, for example, a perovskite material device may contain zero, one, two, three, four, five, or more interfacial layers (such as the example device of FIG. 2, which contains five interfacial layers 3903, 3905, 3907, 3909, and 3911). An interfacial layer may include a thin-coat interfacial layer in accordance with embodiments previously discussed herein (e.g., comprising alumina and/or other metal-oxide particles, and/or a titania/metal-oxide bilayer, and/or other compounds in accordance with thin-coat interfacial layers as discussed elsewhere herein). An interfacial layer according to some embodiments may include any suitable material for enhancing charge transport and/or collection between two layers or materials; it may also help prevent or reduce the likelihood of charge recombination once a charge has been transported away from one of the materials adjacent to the interfacial layer. Suitable interfacial materials may include any one or more of: any mesoporous material and/or interfacial material discussed elsewhere herein; Ag; Al; Au; B; Bi; Ca; Cd; Ce; Co; Cu; Fe; Ga; Ge; H; In; Mg; Mn; Mo; Nb; Ni; Pt; Sb; Sc; Si; Sn; Ta; Ti; V; W; Y; Zn; Zr; carbides of any of the foregoing metals (e.g., SiC, $Fe_3C$; WC); silicides of any of the foregoing metals (e.g., $Mg_2Si$, $SrSi_2$, $Sn_2Si$); oxides of any of the foregoing metals (e.g., alumina, silica, titania, $SnO_2$, ZnO); sulfides of any of the foregoing metals (e.g., CdS, $MoS_2$, $SnS_2$); nitrides of any of the foregoing metals (e.g., $Mg_3N_2$, TiN, BN, $Si_3N_4$); selenides of any of the foregoing metals (e.g., CdSe, $FeSe_2$, ZnSe); tellurides of any of the foregoing metals (e.g., CdTe, $TiTe_2$, ZnTe); phosphides of any of the foregoing metals (e.g., InP, GaP); arsenides of any of the foregoing metals (e.g., $CoAs_3$, GaAs, InGaAs, NiAs); antimonides of any of the foregoing metals (e.g., AlSb, GaSb, InSb); halides of any of the foregoing metals (e.g., CuCl, CuI, $BiI_3$); pseudohalides of any of the foregoing metals (e.g., CuSCN, $AuCN_2$); carbonates of any of the foregoing metals (e.g., $CaCO_3$, $Ce_2(CO_3)_3$); functionalized or non-functionalized alkyl silyl groups; graphite; graphene; fullerenes; carbon nanotubes; any mesoporous material and/or interfacial material discussed elsewhere herein; and combinations thereof (including, in some embodiments, bilayers, trilayers, or multilayers of combined materials). In some embodiments, an interfacial layer may include perovskite material. Further, interfacial layers may comprise doped embodiments of any interfacial material mentioned herein (e.g., Y-doped ZnO, N-doped single-wall carbon nanotubes). Interfacial layers may also comprise a compound having three of the above materials (e.g., $CuTiO_3$, $Zn_2SnO_4$) or a compound having four of the above materials (e.g., CoNiZnO).

Figure 3:
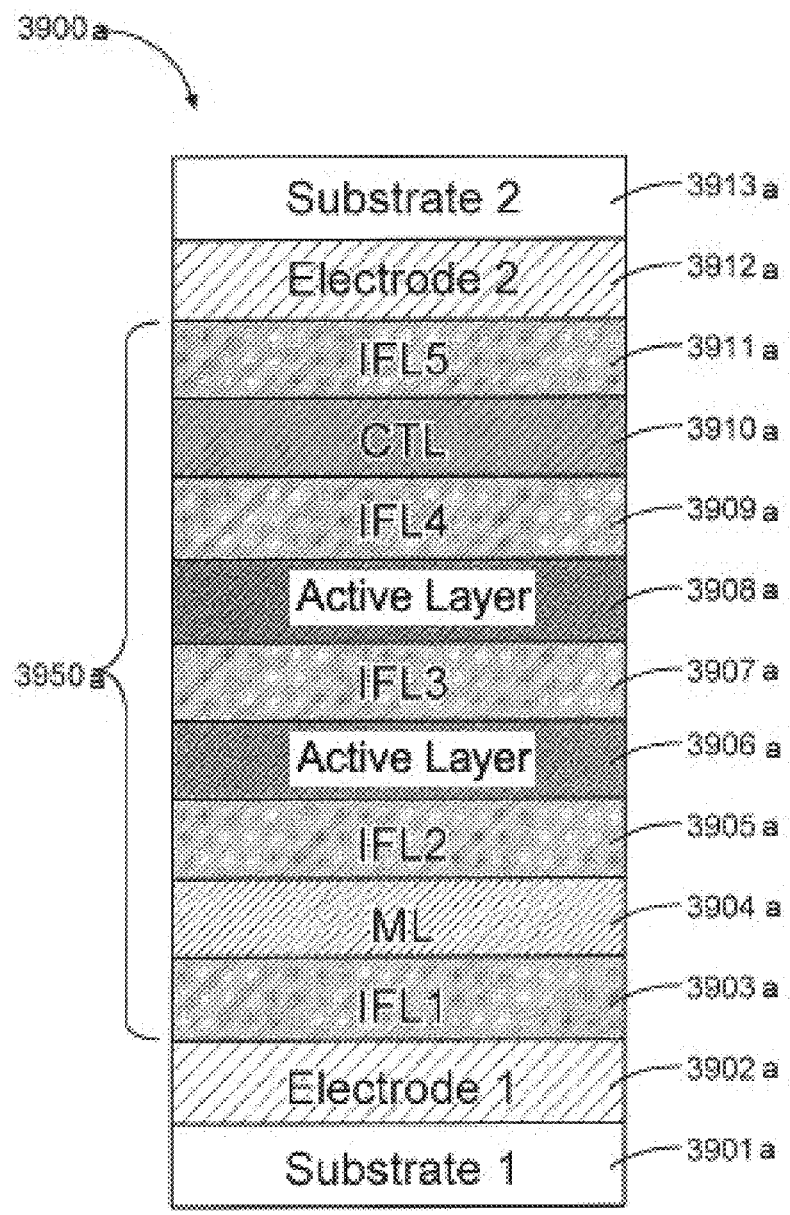
FIG. 3 is a stylized diagram showing components of an example device, according to some embodiments of the present disclosure.

As an example, FIG. 3 illustrates an embodiment of a perovskite material device 3900a having a similar structure to perovskite material device 3900 illustrated by FIG. 2. FIG. 3 is a stylized diagram of a perovskite material device 3900a according to some embodiments. Although various components of the device 3900a are illustrated as discrete layers comprising contiguous material, it should be understood that FIG. 3 is a stylized diagram; thus, embodiments in accordance with it may include such discrete layers, and/or substantially intermixed, non-contiguous layers, consistent with the usage of "layers" previously discussed herein. FIG. 3 includes an active layers 3906a and 3908a. One or both of active layers 3906a and 3908a may, in some embodiments, include any perovskite photoactive materials described above with respect to FIG. 2. In other embodiments, one or both of active layers 3906a and 3908a may include any photoactive material described herein, such as, thin film semiconductors (e.g., CdTe, CZTS, CIGS), photoactive polymers, dye sensitized photoactive materials, fullerenes, small molecule photoactive materials, and crystalline and polycrystalline semiconductor materials (e.g., silicon, GaAs, InP, Ge). In yet other embodiments, one or both of active layers 3906a and 3908a may include a light emitting diode (LED), field effect transistor (FET), thin film battery layer, or combinations thereof. In embodiments, one of active layers 3906a and 3908a may include a photoactive material and the other may include a light emitting diode (LED), field effect transistor (FET), thin film battery layer, or combinations thereof. For example, active layer 3908a may comprise a perovskite material photoactive layer and active layer 3906b may comprise a field effect transistor layer. Other layers illustrated of FIG. 3, such as layers 3901a, 3902a, 3903a, 3904a, 3905a, 3907a (i.e., a recombination layer), 3909a, 3910a, 3911a, 3912a, and 3913a, may be analogous to such corresponding layers as described herein with respect to FIG. 2.

Figure 4:
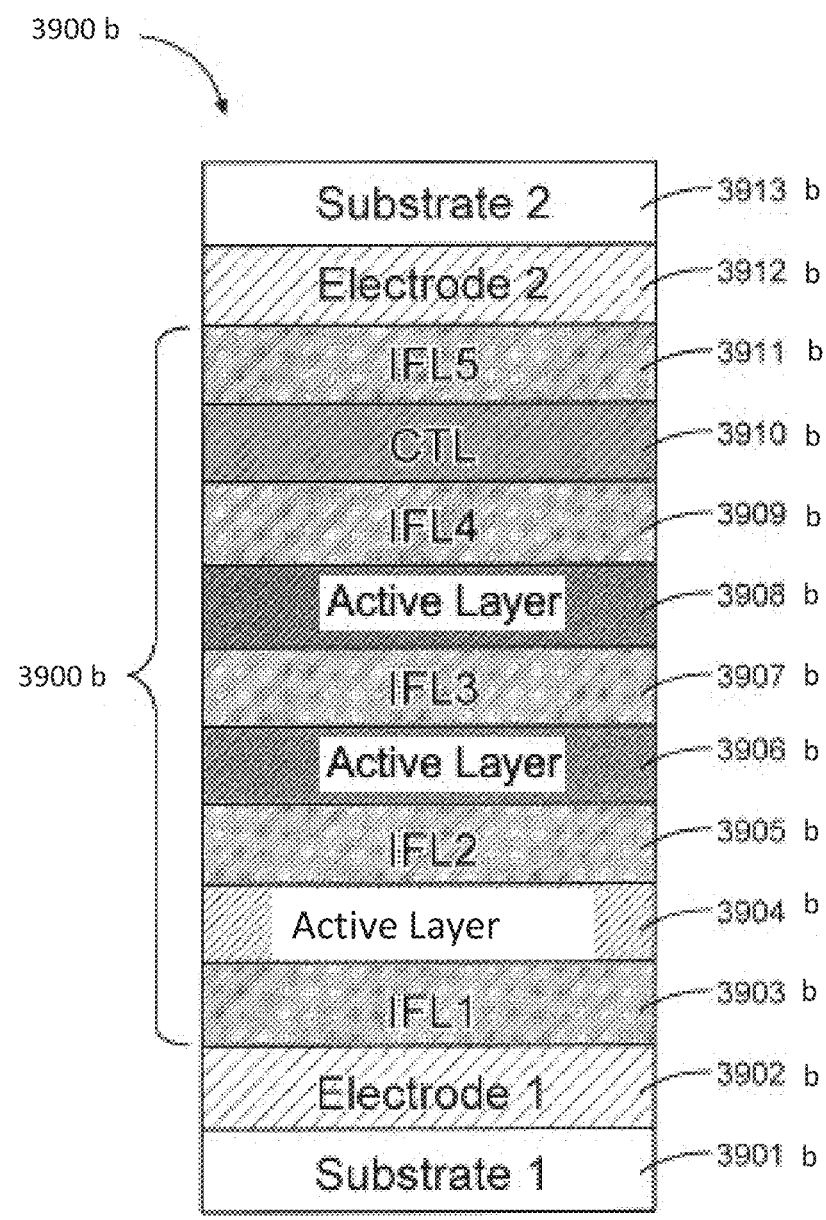
FIG. 4 is a stylized diagram showing components of an example device, according to some embodiments of the present disclosure.

Additionally, in some embodiments, a perovskite material may have three or more active layers. As an example, FIG. 4 illustrates an embodiment of a perovskite material device 3900b having a similar structure to perovskite material device 3900 illustrated by FIG. 2. FIG. 3 is a stylized diagram of a perovskite material device 3900b according to some embodiments. Although various components of the device 3900b are illustrated as discrete layers comprising contiguous material, it should be understood that FIG. 4 is a stylized diagram; thus, embodiments in accordance with it may include such discrete layers, and/or substantially intermixed, non-contiguous layers, consistent with the usage of "layers" previously discussed herein. FIG. 4 includes an active layers 3904b, 3906b and 3908b. One or more of active layers 3904b, 3906b and 3908b may, in some embodiments, include any perovskite photoactive materials described above with respect to FIG. 2. In other embodiments, one or more of active layers 3904b, 3906b and 3908b may include any photoactive material described herein, such as, thin film semiconductors (e.g., CdTe, CZTS, CIGS), photoactive polymers, dye sensitized photoactive materials, fullerenes, small molecule photoactive materials, and crystalline and polycrystalline semiconductor materials (e.g., silicon, GaAs, InP, Ge). In yet other embodiments, one or more of active layers 3904b, 3906b and 3908b may include a light emitting diode (LED), field effect transistor (FET), thin film battery layer, or combinations thereof. In embodiments, one or more of active layers of active layers 3904b, 3906b and 3908b may include a photoactive material and the other may include a light emitting diode (LED), field effect transistor (FET), thin film battery layer, or combinations thereof. For example, active layer 3908a and 3906b may both comprise perovskite material photoactive layers and active layer 3904b may comprise a field effect transistor layer. Other layers illustrated of FIG. 3, such as layers 3901b, 3902b, 3903b, 3904b, 3905b (i.e., a recombination layer), 3907b (i.e., a recombination layer), 3909b, 3910b, 3911b, 3912b, and 3913b, may be analogous to such corresponding layers as described herein with respect to FIG. 2.

Additional, more specific, example embodiments of perovskite devices will be discussed in terms of further stylized depictions of example devices. The stylized nature of these depictions, FIGS. 1-4, similarly is not intended to restrict the type of device which may in some embodiments be constructed in accordance with any one or more of FIGS. 1-4. That is, the architectures exhibited in FIGS. 1-4 may be adapted so as to provide the BHJs, batteries, FETs, hybrid PV batteries, serial multi-cell PVs, parallel multi-cell PVs and other similar devices of other embodiments of the present disclosure, in accordance with any suitable means (including both those expressly discussed elsewhere herein, and other suitable means, which will be apparent to those skilled in the art with the benefit of this disclosure).

Formulation of the Perovskite Material Active Layer

As discussed earlier, in some embodiments, a perovskite material in the active layer may have the formulation $CMX_{3-y}X'_y$ ($0 \geq y \geq 3$), where: C comprises one or more cations (e.g., an amine, ammonium, a Group 1 metal, a Group 2 metal, formamidinium, guanidinium, ethene tetramine, phosphonium, imidazolium, and/or other cations or cation-like compounds); M comprises one or more metals (e.g., Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr); and X and X' comprise one or more anions. In one embodiment, the perovskite material may comprise $CPbI_{3-y}Cl_y$. In some embodiments, the perovskite material may comprise two or more anions or three or more anions. In certain embodiments, the perovskite material may comprise two or more metals or three or more metals. In some embodiments, the perovskite material may comprise two more cations or three or more cations.

In some embodiments, a perovskite material in the active layer may have the formulation $C_{1-x}C'_xMX_3$ ($0 \geq x \geq 1$), where C and C' comprise one or more cations (e.g., an amine, ammonium, a Group 1 metal, a Group 2 metal, formamidinium, guanidinium, ethene tetramine, phosphonium, imidazolium, and/or other cations or cation-like compounds); M comprises one or more metals (e.g., Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr); and X comprises one or more anions.

In some embodiments, a perovskite material in the active layer may have the formulation $CM_{1-z}M'_zX_3$ ($0 \geq z \geq 1$), where: C comprises one or more cations (e.g., an amine, ammonium, a Group 1 metal, a Group 2 metal, formamidinium, guanidinium, ethene tetramine, phosphonium, imidazolium, and/or other cations or cation-like compounds); M and M' comprise one or more metals (e.g., Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr); and X comprises one or more anions.

In some embodiments, a perovskite material in the active layer may have the formulation $C_{1-x}C'_xM_{1-z}M'_zX_{3-y}X'_y$ ($0 \geq x \geq 1$; $0 \geq y \geq 3$; $0 \geq z \geq 1$), where: C and C' comprise one or more cations (e.g., an amine, ammonium, a Group 1 metal, a Group 2 metal, formamidinium, guanidinium, ethene tetramine, phosphonium, imidazolium, and/or other cations or cation-like compounds); M and M' comprise one or more metals (e.g., Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr); and X and X' comprise one or more anions. In certain embodiments, the perovskite material may be deposited as an active layer in a PV device by, for example, blade coating, drop casting, spin casting, slot-die printing, screen printing, or ink-jet printing onto a substrate layer using the steps described below.

First, a lead halide precursor ink is formed. An amount of lead halide may be massed in a clean, dry vessel in a controlled atmosphere environment (e.g., a controlled atmosphere box with glove-containing portholes allows for materials manipulation in an air-free environment). Suitable lead halides include, but are not limited to, lead (II) iodide, lead (II) bromide, lead (II) chloride, and lead (II) fluoride. The lead halide may comprise a single species of lead halide or it may comprise a lead halide mixture in a precise ratio. In certain embodiments, the lead halide mixture may comprise any binary, ternary, or quaternary ratio of 0.001-100 mol % of iodide, bromide, chloride, or fluoride. In one embodiment, the lead halide mixture may comprise lead (II) chloride and lead (II) iodide in a ratio of about 10:90 mol:mol. In other embodiments, the lead halide mixture may comprise lead (II) chloride and lead (II) iodide in a ratio of about 5:95, about 7.5:92.5, or about 15:85 mol:mol.

Alternatively, other lead salt precursors may be used in conjunction with or in lieu of lead halide salts to form the precursor ink. Suitable precursor salts may comprise any combination of lead (II) or lead (IV) and the following anions: nitrate, nitrite, carboxylate, acetate, acetonyl acetonate, formate, oxalate, sulfate, sulfite, thiosulfate, phosphate, tetrafluoroborate, hexafluorophosphate, tetra(perfluorophenyl) borate, hydride, oxide, peroxide, hydroxide, nitride, arsenate, arsenite, perchlorate, carbonate, bicarbonate, chromate, dichromate, iodate, bromate, chlorate, chlorite, hypochlorite, hypobromite, cyanide, cyanate, isocyanate, fulminate, thiocyanate, isothiocyanate, azide, tetracarbonylcobaltate, carbamoyldicyanomethanide, dicyanonitrosomethanide, dicyanamide, tricyanomethanide, amide, and permanganate.

The precursor ink may further comprise a lead (II) or lead (IV) salt in mole ratios of 0 to 100% to the following metal ions Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr as a salt of the aforementioned anions.

A solvent may then be added to the vessel to dissolve the lead solids to form the lead halide precursor ink. Suitable solvents include, but are not limited to, dry N-cyclohexyl-2-pyrrolidone, alkyl-2-pyrrolidone, dimethylformamide, dialkylformamide, dimethylsulfoxide (DMSO), methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations thereof. In one embodiment, the lead solids are dissolved in dry dimethylformamide (DMF). The lead solids may be dissolved at a temperature between about 20° C. to about 150° C. In one embodiment, the lead solids are dissolved at about 85° C. The lead solids may be dissolved for as long as necessary to form a solution, which may take place over a time period up to about 72 hours. The resulting solution forms the base of the lead halide precursor ink. In some embodiments, the lead halide precursor ink may have a lead halide concentration between about 0.001M and about 10M. In one embodiment, the lead halide precursor ink has a lead halide concentration of about 1 M.

Optionally, certain additives may be added to the lead halide precursor ink to affect the final perovskite crystallinity and stability. In some embodiments, the lead halide precursor ink may further comprise an amino acid (e.g., 5-aminovaleric acid, histidine, glycine, lysine), an amino acid hydrohalide (e.g., 5-amino valeric acid hydrochloride), an IFL surface-modifying (SAM) agent (such as those discussed earlier in the specification), or a combination thereof. Amino acids suitable for lead halide precursor inks may include, but are not limited to α-amino acids, β-amino acids, γ-amino acids, δ-amino acids, and any combination thereof. In one embodiment, formamidinium chloride may be added to the lead halide precursor ink. In other embodiments, the halide of any cation discussed earlier in the specification may be used. In some embodiments, combinations of additives may be added to the lead halide precursor ink including, for example, the combination of formamidinium chloride and 5-amino valeric acid hydrochloride.

By way of explanation, and without limiting the disclosure to any particular theory of mechanism, it has been found that formamidinium chloride and 5-amino valeric acid improve perovskite PV device stability when they are used as additives or counter-cations in a one-step perovskite device fabrication. It has also been found that chloride, in the form of $PbCl_2$, improves perovskite PV device performance when added to a $PbI_2$ precursor solution in a two-step method. It has been found that the two-step perovskite thin film deposition process may be improved by adding formamidinium chloride and/or 5-amino valeric acid hydrochloride directly to a lead halide precursor solution (e.g., $PbI_2$) to leverage both advantages with a single material. Other perovskite film deposition processes may likewise be improved by the addition of formamidinium chloride, 5-amino valeric acid hydrochloride, or $PbCl_2$ to a lead halide precursor solution.

The additives, including formamidinium chloride and/or 5-amino valeric acid hydrochloride. may be added to the lead halide precursor ink at various concentrations depending on the desired characteristics of the resulting perovskite material. In one embodiment, the additives may be added in a concentration of about 1 nM to about 1 M. In another embodiment, the additives may be added in a concentration of about 1 µM to about 1 M. In another embodiment, the additives may be added in a concentration of about 1 µM to about 1 mM.

Optionally, in certain embodiments, water may be added to the lead halide precursor ink. By way of explanation, and without limiting the disclosure to any particular theory or mechanism, the presence of water affects perovskite thin-film crystalline growth. Under normal circumstances, water may be absorbed as vapor from the air. However, it is possible to control the perovskite PV crystallinity through the direct addition of water to the lead halide precursor ink in specific concentrations. Suitable water includes distilled, deionized water, or any other source of water that is substantially free of contaminants (including minerals). It has been found, based on light I-V sweeps, that the perovskite PV light-to-power conversion efficiency may nearly triple with the addition of water compared to a completely dry device.

The water may be added to the lead halide precursor ink at various concentrations depending on the desired characteristics of the resulting perovskite material. In one embodiment, the water may be added in a concentration of about 1 nL/mL to about 1 mL/mL. In another embodiment, the water may be added in a concentration of about 1 µL/mL to about 0.1 mL/mL. In another embodiment, the water may be added in a concentration of about 1 µL/mL to about 20 µL/mL.

The lead halide precursor ink may then be deposited on the desired substrate. Suitable substrate layers may include any of the substrate layers identified earlier in this disclosure. As noted above, the lead halide precursor ink may be deposited through a variety of means, including but not limited to, drop casting, spin casting, slot-die printing, screen printing, or ink-jet printing. In certain embodiments, the lead halide precursor ink may be spin-coated onto the substrate at a speed of about 500 rpm to about 10,000 rpm for a time period of about 5 seconds to about 600 seconds. In one embodiment, the lead halide precursor ink may be spin-coated onto the substrate at about 3000 rpm for about 30 seconds. The lead halide precursor ink may be deposited on the substrate at an ambient atmosphere in a humidity range of about 0% relative humidity to about 50% relative humidity. The lead halide precursor ink may then be allowed to dry in a substantially water-free atmosphere, i.e., less than 30% relative humidity, to form a thin film.

The thin film may then be thermally annealed for a time period up to about 24 hours at a temperature of about 20° C.

to about 300° C. In one embodiment, the thin film may be thermally annealed for about ten minutes at a temperature of about 50° C. The perovskite material active layer may then be completed by a conversion process in which the precursor film is submerged or rinsed with a solution comprising a solvent or mixture of solvents (e.g., DMF, isopropanol, methanol, ethanol, butanol, chloroform chlorobenzene, dimethylsulfoxide, water) and salt (e.g., methylammonium iodide, formamidinium iodide, guanidinium iodide, 1,2,2-triaminovinylammonium iodide, 5-aminovaleric acid hydroiodide) in a concentration between 0.001M and 10M. In certain embodiments, the thin films may also be thermally post-annealed in the same fashion as in the first line of this paragraph.

In some embodiments, a lead salt precursor may be deposited onto a substrate to form a lead salt thin film. The substrate may have a temperature about equal to ambient temperature or have a controlled temperature between 0° C. and 500° C. The lead salt precursor may be deposited by a variety of methods known in the art, including but not limited to spin-coating, slot-die printing, ink-jet printing, gravure printing, screen printing, sputtering, PE-CVD, thermal evaporation, spray coating. In certain embodiments, the deposition of the lead salt precursor may comprise sheet-to-sheet or roll-to-roll manufacturing methodologies. Deposition of the lead salt precursor may be performed in a variety of atmospheres at ambient pressure (e.g. about one atmosphere, depending on elevation and atmospheric conditions) or at pressures less than atmospheric or ambient (e.g., 1 mTorr to 500 mTorr). The deposition atmosphere may comprise ambient air, a controlled humidity environment (e.g., 0-100 g $H_2O/m^3$ of gas), pure argon, pure nitrogen, pure oxygen, pure hydrogen, pure helium, pure neon, pure krypton, pure $CO_2$ or any combination of the preceding gases. A controlled humidity environment may include an environment in which the absolute humidity or the % relative humidity is held at a fixed value, or in which the absolute humidity or the % relative humidity varies according to predetermined set points or a predetermined function. In particular embodiments, deposition may occur in a controlled humidity environment having a % relative humidity greater than or equal to 0% and less than or equal to 50%. In other embodiments, deposition may occur in a controlled humidity environment containing greater than or equal to 0 g $H_2O/m^3$ gas and less than or equal to 20 g $H_2O/m^3$ gas.

The lead salt precursor may be a liquid, a gas, solid, or combination of these states of matter such as a solution, suspension, colloid, foam, gel, or aerosol. In some embodiments, the lead salt precursor may be a solution containing one or more solvents. For example, the lead salt precursor may contain one or more of N-cyclohexyl-2-pyrrolidone, alkyl-2-pyrrolidone, dimethylformamide, dialkylformamide, dimethylsulfoxide (DMSO), acetonitrile, methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations thereof. The lead salt precursor may comprise a single lead salt (e.g., lead (II) iodide, lead (II) thiocyanate) or any combination of those disclosed herein (e.g., $PbI_2+PbCl_2$; $PbI_2+Pb(SCN)_2$). The lead salt precursor may also contain one or more additives such as an amino acid (e.g., 5-aminovaleric acid hydroiodide), 1,8-diiodooctane, 1,8-dithiooctane, formamidinium halide, acetic acid, trifluoroacetic acid, a methylammonium halide, or water. The lead halide precursor ink may be allowed to dry in a substantially water-free atmosphere, i.e., less than 30% relative humidity, to form a thin film. The thin film may then be thermally annealed for a time period of up to about 24 hours at a temperature of about 20° C. to about 300° C. Annealing may be performed in a variety of atmospheres at ambient pressure (e.g. about one atmosphere, depending on elevation and atmospheric conditions) or at pressures less than atmospheric or ambient (e.g., 1 mTorr to 500 mTorr). An annealing atmosphere may comprise ambient air, a controlled humidity environment (e.g., 0-100 g $H_2O/m^3$ of gas), pure argon, pure nitrogen, pure oxygen, pure hydrogen, pure helium, pure neon, pure krypton, pure $CO_2$ or any combination of the preceding gases. A controlled humidity environment may include an environment in which the absolute humidity or the % relative humidity is held at a fixed value, or in which the absolute humidity or the % relative humidity varies according to predetermined set points or a predetermined function. In particular embodiments, annealing may occur in a controlled humidity environment having a % relative humidity greater than or equal to 0% and less than or equal to 50%. In other embodiments, annealing may occur in a controlled humidity environment containing greater than or equal to 0 g $H_2O/m^3$ gas and less than or equal to 20 g $H_2O/m^3$ gas After the lead salt precursor is deposited, a second salt precursor (e.g., formamidinium iodide, formamidinium thiocyanate, guanidinium thiocyanate) may be deposited onto the lead salt thin film, where the lead salt thin film may have a temperature about equal to ambient temperature or have a controlled temperature between 0° C. and 500° C. The second salt precursor, in some embodiments, may be deposited at ambient temperature or at elevated temperature between about 25° C. and 125° C. The second salt precursor may be deposited by a variety of methods known in the art, including but not limited to spin-coating, slot-die printing, ink-jet printing, gravure printing, screen printing, sputtering, PE-CVD, thermal evaporation, or spray coating. Deposition of the second salt precursor may be performed in a variety of atmospheres at ambient pressure (e.g. about one atmosphere, depending on elevation and atmospheric conditions) or at pressures less than atmospheric or ambient (e.g., 1 mTorr to 500 mTorr). The deposition atmosphere may comprise ambient air, a controlled humidity environment (e.g., 0-100 g $H_2O/m^3$ of gas), pure argon, pure nitrogen, pure oxygen, pure hydrogen, pure helium, pure neon, pure krypton, pure $CO_2$ or any combination of the preceding gases. A controlled humidity environment may include an environment in which the absolute humidity or the % relative humidity is held at a fixed value, or in which the absolute humidity or the % relative humidity varies according to predetermined set points or a predetermined function. In particular embodiments, deposition may occur in a controlled humidity environment having a % relative humidity greater than or equal to 0% and less than or equal to 50%. In other embodiments, deposition may occur in a controlled humidity environment containing greater than or equal to 0 g $H_2O/m^3$ gas and less than or equal to 20 g $H_2O/m^3$ gas.

In some embodiments the second salt precursor may be a solution containing one or more solvents. For example, the second salt precursor may contain one or more of dry N-cyclohexyl-2-pyrrolidone, alkyl-2-pyrrolidone, dimethylformamide, dialkylformamide, dimethylsulfoxide (DMSO), acetonitrile, methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations thereof.

After deposition of the lead salt precursor and second salt precursor, the substrate may be annealed. Annealing the substrate may convert the lead salt precursor and second salt precursor to a perovskite material, (e.g. $FAPbI_3$, GAPb $(SCN)_3$, $FASnI_3$). Annealing may be performed in a variety of atmospheres at ambient pressure (e.g. about one atmosphere, depending on elevation and atmospheric conditions) or at pressures less than atmospheric or ambient (e.g., 1 mTorr to 500 mTorr). An annealing atmosphere may comprise ambient air, a controlled humidity environment (e.g., 0-100 g $H_2O/m^3$ of gas), pure argon, pure nitrogen, pure oxygen, pure hydrogen, pure helium, pure neon, pure krypton, pure $CO_2$ or any combination of the preceding gases. A controlled humidity environment may include an environment in which the absolute humidity or the % relative humidity is held at a fixed value, or in which the absolute humidity or the % relative humidity varies according to predetermined set points or a predetermined function. In particular embodiments, annealing may occur in a controlled humidity environment having a % relative humidity greater than or equal to 0% and less than or equal to 50%. In other embodiments, annealing may occur in a controlled humidity environment containing greater than or equal to 0 g $H_2O/m^3$ gas and less than or equal to 20 g $H_2O/m^3$ gas. In some embodiments, annealing may occur at a temperature greater than or equal to 50° C. and less than or equal to 300° C. Unless described as otherwise, any annealing or deposition step described herein may be carried out under the preceding conditions.

For example, in a particular embodiment, a $FAPbI_3$ perovskite material may be formed by the following process. First a lead (II) halide precursor comprising about a 90:10 mole ratio of $PbI_2$ to $PbCl_2$ dissolved in anhydrous DMF may be deposited onto a substrate by spin-coating or slot-die printing. The lead halide precursor ink may be allowed to dry in a substantially water-free atmosphere, i.e., less than 30% relative humidity, for approximately one hour (+15 minutes) to form a thin film. The thin film may be subsequently thermally annealed for about ten minutes at a temperature of about 50° C. (±10° C.). In other embodiments, the lead halide precursor may be deposited by ink-jet printing, gravure printing, screen printing, sputtering, PE-CVD, atomic-layer deposition, thermal evaporation, or spray coating. Next, a formamidinium iodide precursor comprising a 25-60 mg/mL concentration of formamidinium iodide dissolved in anhydrous isopropyl alcohol may be deposited onto the lead halide thin film by spin coating or slot-die printing. In other embodiments, the formamidinium iodide precursor may be deposited by ink-jet printing, gravure printing, screen printing, sputtering, PE-CVD, atomic-layer deposition, thermal evaporation, or spray coating. After depositing the lead halide precursor and formamidinium iodide precursor, the substrate may be annealed at about 25% relative humidity (about 4 to 7 g $H_2O/m^3$ air) and between about 125° C. and 200° C. to form a formamidinium lead iodide ($FAPbI_3$) perovskite material.

In another embodiment, a perovskite material may comprise $C'CPbX_3$, where C' is one or more Group 1 metals (i.e. Li, Na, K, Rb, Cs). In a particular embodiment M' may be cesium (Cs). In another embodiment C' may be rubidium (Rb). In another embodiment C' may be sodium (Na). In another embodiment C' may be potassium (K). In yet other embodiments, a perovskite material may comprise $C'_vC_wPb_yX_z$, where C' is one or more Group 1 metals and v, w, y, and z represent real numbers between 1 and 20. In certain embodiments, the perovskite material may be deposited as an active layer in a PV device by, for example, drop casting, spin casting, gravure coating, blade coating, reverse gravure coating, slot-die printing, screen printing, or ink-jet printing onto a substrate layer using the steps described below.

First, a lead halide solution is formed. An amount of lead halide may be massed in a clean, dry vessel in a controlled atmosphere environment. Suitable lead halides include, but are not limited to, lead (II) iodide, lead (II) bromide, lead (II) chloride, and lead (II) fluoride. The lead halide may comprise a single species of lead halide or it may comprise a lead halide mixture in a precise ratio. In one embodiment the lead halide may comprise lead (II) iodide. In certain embodiments, the lead halide mixture may comprise any binary, ternary, or quaternary ratio of 0.001-100 mol % of iodide, bromide, chloride, or fluoride. In one embodiment, the lead halide mixture may comprise lead (II) chloride and lead (II) iodide in a ratio of about 10:90 mol:mol. In other embodiments, the lead halide mixture may comprise lead (II) chloride and lead (II) iodide in a ratio of about 5:95, about 7.5:92.5, or about 15:85 mol:mol.

Alternatively, other lead salt precursors may be used in conjunction with or in lieu of lead halide salts to form a lead salt solution. Suitable precursor lead salts may comprise any combination of lead (II) or lead (IV) and the following anions: nitrate, nitrite, carboxylate, acetate, formate, oxalate, sulfate, sulfite, thiosulfate, phosphate, tetrafluoroborate, hexafluorophosphate, tetra(perfluorophenyl) borate, hydride, oxide, peroxide, hydroxide, nitride, arsenate, arsenite, perchlorate, carbonate, bicarbonate, chromate, dichromate, iodate, bromate, chlorate, chlorite, hypochlorite, hypobromite, cyanide, cyanate, isocyanate, fulminate, thiocyanate, isothiocyanate, azide, tetracarbonylcobaltate, carbamoyldicyanomethanide, dicyanonitrosomethanide, dicyanamide, tricyanomethanide, amide, and permanganate.

The lead salt solution may further comprise a lead (II) or lead (IV) salt in mole ratios of 0 to 100% to the following metal ions Be, Mg, Ca, Sr, Ba, Fe, Cd, Co, Ni, Cu, Ag, Au, Hg, Sn, Ge, Ga, Pb, In, Tl, Sb, Bi, Ti, Zn, Cd, Hg, and Zr as a salt of the aforementioned anions.

A solvent may then be added to the vessel to dissolve the lead halide solids to form the lead halide solution. Suitable solvents include, but are not limited to, dry N-cyclohexyl-2-pyrrolidone, alkyl-2-pyrrolidone, dimethylformamide (DMF), dialkylformamide, dimethylsulfoxide (DMSO), acetonitrile, methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations thereof. In one embodiment, the lead solids are dissolved in dry dimethylformamide (DMF). The lead halide solids may be dissolved at a temperature between about 20° C. to about 150° C. In one embodiment, the lead halide solids are dissolved at about 85° C. The lead halide solids may be dissolved for as long as necessary to form a solution, which may take place over a time period up to about 72 hours. The resulting solution forms the base of the lead halide precursor ink. In some embodiments, the lead halide precursor ink may have a lead halide concentration between about 0.001M and about 10M. In one embodiment, the lead halide precursor ink has a lead halide concentration of about 1 M. In some embodiments, the lead halide solution may further comprise an amino acid (e.g., 5-aminovaleric acid, histidine, glycine, lysine), an amino acid hydrohalide (e.g., 5-amino valeric acid hydrochloride), an IFL surface-modifying (SAM) agent (such as those discussed earlier in the specification), or a combination thereof.

Next, a Group 1 metal halide solution is formed. An amount of Group 1 metal halide may be massed in a clean, dry vessel in a controlled atmosphere environment. Suitable Group 1 metal halides include, but are not limited to, cesium iodide, cesium bromide, cesium chloride, cesium fluoride, rubidium iodide, rubidium bromide, rubidium chloride, rubidium fluoride, lithium iodide, lithium bromide, lithium chloride, lithium fluoride, sodium iodide, sodium bromide, sodium chloride, sodium fluoride, potassium iodide, potassium bromide, potassium chloride, potassium fluoride. The Group 1 metal halide may comprise a single species of Group 1 metal halide or it may comprise a Group 1 metal halide mixture in a precise ratio. In one embodiment the Group 1 metal halide may comprise cesium iodide. In another embodiment the Group 1 metal halide may comprise rubidium iodide. In another embodiment the Group 1 metal halide may comprise sodium iodide. In another embodiment the Group 1 metal halide may comprise potassium iodide.

Alternatively, other Group 1 metal salt precursors may be used in conjunction with or in lieu of Group 1 metal halide salts to form a Group 1 metal salt solution. Suitable precursor Group 1 metal salts may comprise any combination of Group 1 metals and the following anions: nitrate, nitrite, carboxylate, acetate, formate, oxalate, sulfate, sulfite, thiosulfate, phosphate, tetrafluoroborate, hexafluorophosphate, tetra(perfluorophenyl) borate, hydride, oxide, peroxide, hydroxide, nitride, arsenate, arsenite, perchlorate, carbonate, bicarbonate, chromate, dichromate, iodate, bromate, chlorate, chlorite, hypochlorite, hypobromite, cyanide, cyanate, isocyanate, fulminate, thiocyanate, isothiocyanate, azide, tetracarbonylcobaltate, carbamoyldicyanomethanide, dicyanonitrosomethanide, dicyanamide, tricyanomethanide, amide, and permanganate.

A solvent may then be added to the vessel to dissolve the Group 1 metal halide solids to form the Group 1 metal halide solution. Suitable solvents include, but are not limited to, dry N-cyclohexyl-2-pyrrolidone, alkyl-2-pyrrolidone, dimethylformamide (DMF), dialkylformamide, dimethylsulfoxide (DMSO), acetonitrile, methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations thereof. In one embodiment, the lead solids are dissolved in dry dimethylsulfoxide (DMSO). The Group 1 metal halide solids may be dissolved at a temperature between about 20° C. to about 150° C. In one embodiment, the Group 1 metal halide solids are dissolved at room temperature (i.e., about 25° C.). The Group 1 metal halide solids may be dissolved for as long as necessary to form a solution, which may take place over a time period up to about 72 hours. The resulting solution forms the Group 1 metal halide solution. In some embodiments, the Group 1 metal halide solution may have a Group 1 metal halide concentration between about 0.001M and about 10M. In one embodiment, the Group 1 metal halide solution has a Group 1 metal halide concentration of about 1 M. In some embodiments, the Group 1 metal halide solution may further comprise an amino acid (e.g., 5-aminovaleric acid, histidine, glycine, lysine), an amino acid hydrohalide (e.g., 5-amino valeric acid hydrochloride), an IFL surface-modifying (SAM) agent (such as those discussed earlier in the specification), or a combination thereof.

Next, the lead halide solution and the Group 1 metal halide solution are mixed to form a thin-film precursor ink. The lead halide solution and Group 1 metal halide solution may be mixed in a ratio such that the resulting thin-film precursor ink has a molar concentration of the Group 1 metal halide that is between 0% and 25% of the molar concentration of the lead halide. In particular embodiments, the thin-film precursor ink may have a molar concentration of the Group 1 metal halide that is 1% of the molar concentration of the lead halide. In particular embodiments, the thin-film precursor ink may have a molar concentration of the Group 1 metal halide that is 5% of the molar concentration of the lead halide. In particular embodiments, the thin-film precursor ink may have a molar concentration of the Group 1 metal halide that is 10% of the molar concentration of the lead halide. In particular embodiments, the thin-film precursor ink may have a molar concentration of the Group 1 metal halide that is 15% of the molar concentration of the lead halide. In particular embodiments, the thin-film precursor ink may have a molar concentration of the Group 1 metal halide that is 20% of the molar concentration of the lead halide. In particular embodiments, the thin-film precursor ink may have a molar concentration of the Group 1 metal halide that is 25% of the molar concentration of the lead halide. In some embodiments the lead halide solution and the Group 1 metal halide solution may be stirred or agitated during or after mixing.

The thin-film precursor ink may then be deposited on the desired substrate. Suitable substrate layers may include any of the substrate layers identified earlier in this disclosure. As noted above, the thin-film precursor ink may be deposited through a variety of means, including but not limited to, drop casting, spin casting, gravure coating, blade coating, reverse gravure coating, slot-die printing, screen printing, or ink-jet printing. In certain embodiments, the thin-film precursor ink may be spin-coated onto the substrate at a speed of about 500 rpm to about 10,000 rpm for a time period of about 5 seconds to about 600 seconds. In one embodiment, the thin-film precursor ink may be spin-coated onto the substrate at about 3000 rpm for about 30 seconds. The thin-film precursor ink may be deposited on the substrate at an ambient atmosphere in a humidity range of about 0% relative humidity to about 50% relative humidity. The thin-film precursor ink may then be allowed to dry in a substantially water-free atmosphere, i.e., less than 30% relative humidity or 7 g $H_2O/m^3$, to form a thin film.

The thin film can then be thermally annealed for a time period up to about 24 hours at a temperature of about 20° C. to about 300° C. In one embodiment, the thin film may be thermally annealed for about ten minutes at a temperature of about 50° C. The perovskite material active layer may then be completed by a conversion process in which the precursor film is submerged or rinsed with a salt solution comprising a solvent or mixture of solvents (e.g., DMF, isopropanol, methanol, ethanol, butanol, chloroform chlorobenzene, dimethylsulfoxide, water) and salt (e.g., methylammonium iodide, formamidinium iodide, guanidinium iodide, 1,2,2-triaminovinylammonium iodide, 5-aminovaleric acid hydroiodide) in a concentration between 0.001M and 10M. In certain embodiments, the perovskite material thin films can also be thermally post-annealed in the same fashion as in the first line of this paragraph.

In some embodiments, the salt solution may be prepared by massing the salt in a clean, dry vessel in a controlled atmosphere environment. Suitable salts include, but are not limited to, methylammonium iodide, formamidinium iodide, guanidinium iodide, imidazolium iodide, ethene tetramine iodide, 1,2,2-triaminovinylammonium iodide, and 5-aminovaleric acid hydroiodide. Other suitable salts may include any organic cation described above in the section entitled "Perovskite Material." The salt may comprise a single species of salt or it may comprise a salt mixture in a precise ratio. In one embodiment the salt may comprise methylammonium iodide. In another embodiment the salt may comprise formamidinium iodide. Next, a solvent may then be added to the vessel to dissolve the salt solids to form the salt solution. Suitable solvents include, but are not limited to, DMF, acetonitrile, isopropanol, methanol, ethanol, butanol, chloroform chlorobenzene, dimethylsulfoxide, water, and combinations thereof. In one embodiment, formamidinium iodide salt solids are dissolved in isopropanol. The salt solids may be dissolved at a temperature between about 20° C. to about 150° C. In one embodiment, the salt solids are dissolved at room temperature (i.e. about 25° C.). The salt solids may be dissolved for as long as necessary to form a solution, which may take place over a time period up to about 72 hours. The resulting solution forms the salt solution. In some embodiments, the salt solution may have a salt concentration between about 0.001M and about 10M. In one embodiment, the salt solution has a salt concentration of about 1 M.

For example, using the process described above with a lead (II) iodide solution, a cesium iodide solution, and a methylammonium (MA) iodide salt solution may result in a perovskite material having the a formula of $Cs_iMA_{1-i}PbI_3$, where i equals a number between 0 and 1. As another example, using a lead (II) iodide solution, a rubidium iodide solution, and a formamidinium (FA) iodide salt solution may result in a perovskite material having the a formula of $Rb_iFA_{1-i}PbI_3$, where i equals a number between 0 and 1. As another example, using a lead (II) iodide solution, a cesium iodide solution, and a formamidinium (FA) iodide salt solution may result in a perovskite material having the a formula of $Cs_iFA_{1-i}PbI_3$, where i equals a number between 0 and 1. As another example, using a lead (II) iodide solution, a potassium iodide solution, and a formamidinium (FA) iodide salt solution may result in a perovskite material having the a formula of $K_iFA_{1-i}PbI_3$, where i equals a number between 0 and 1. As another example, the using a lead (II) iodide solution, a sodium iodide solution, and a formamidinium (FA) iodide salt solution may result in a perovskite material having the a formula of $Na_iFA_{1-i}PbI_3$, where i equals a number between 0 and 1. As another example, the using a lead (II) iodide-lead (II) chloride mixture solution, a cesium iodide solution, and a formamidinium (FA) iodide salt solution may result in a perovskite material having the a formula of $Cs_iFA_{1-i}PbI_{3-y}Cl_y$, where i equals a number between 0 and 1 and y represents a number between 0 and 3.

In a particular embodiment, the lead halide solution as described above may have a ratio of 90:10 of $PbI_2$ to $PbCl_2$ on a mole basis. A cesium iodide (CsI) solution may be added to the lead halide solution by the method described above to form a thin film precursor ink with 10 mol % CsI. A $FAPbI_3$ perovskite material may be produced according to the method described above using this thin film precursor solution. The addition of cesium ions through the CsI solution as described above may cause chloride anions and cesium atoms to incorporate into the $FAPbI_3$ crystal lattice. This may result in a greater degree of lattice contraction compared to addition of cesium or rubidium ions as described above without addition of chloride ions. Table 1 below shows lattice parameters for $FAPbI_3$ perovskite materials with 10 mol % rubidium and 20 mol % chloride (e.g. 10 mol % $PbCl_2$), 10 mol % cesium, and 10 mol % cesium with 20 mol % chloride, wherein the mol % concentration represents the concentration of the additive with respect to the lead atoms in the lead halide solution. As can be seen in Table 1, the $FAPbI_3$ perovskite material with cesium and chloride added has smaller lattice parameters than the other two perovskite material samples.

TABLE 1

| Sample Details | (001) d-spacing | (002) d-spacing |
| --- | --- | --- |
| 10 mol % RbI + 10 mol % $PbCl_2$ | 6.3759(15) | 3.1822(5) |
| 10 mol % CsI + 0 mol % $PbCl_2$ | 6.3425(13) | 3.1736(8) |
| 10 mol % CsI + 10 mol % $PbCl_2$ | 6.3272(13) | 3.1633(4) |

Figure 29:
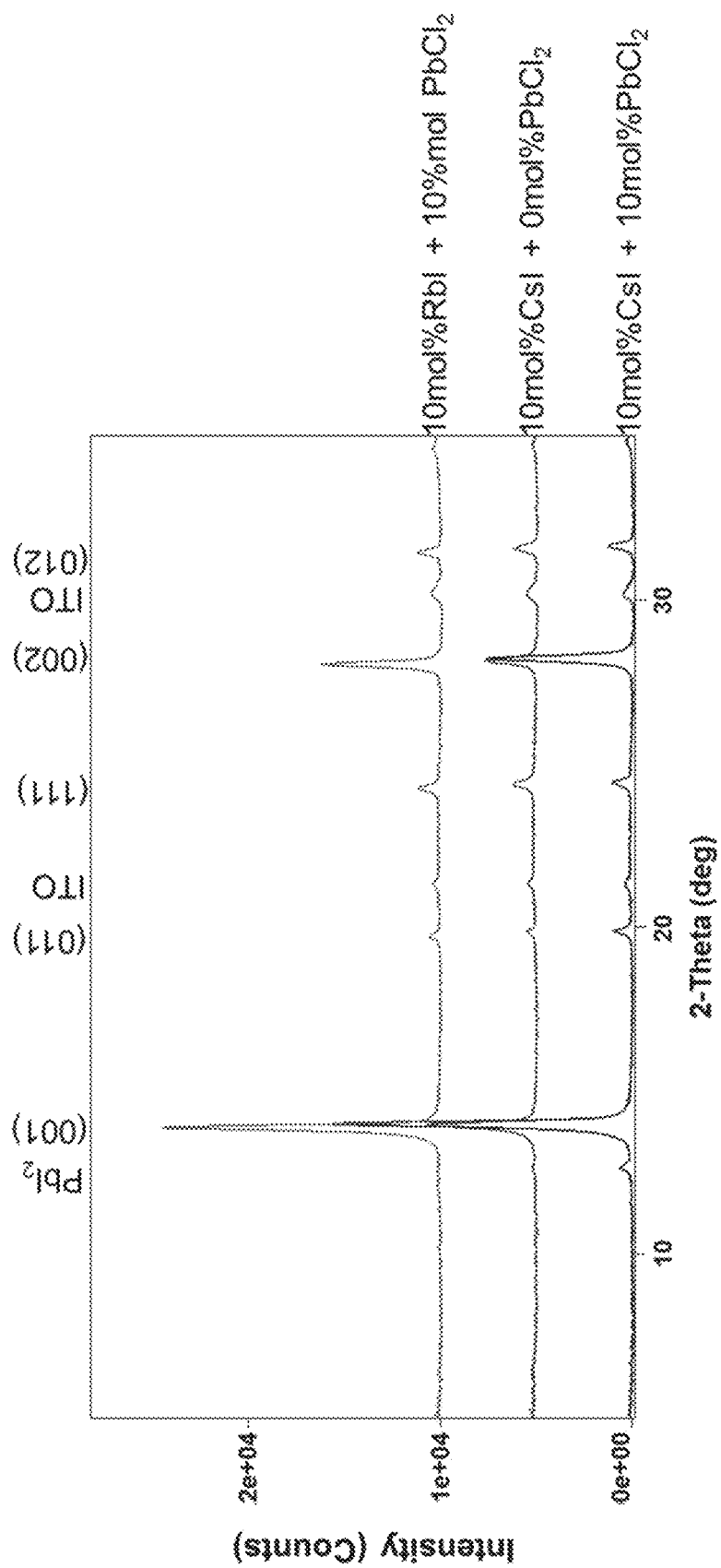
FIG. 29 illustrates x-ray diffraction patterns of perovskites materials, according to some embodiments of the present disclosure.

Additionally, data shows that the $FAPbI_3$ perovskite material with rubidium, cesium and/or chloride added has a Pm3-m cubic structure. $FAPbI_3$ perovskites with up to and including 10 mol % Rb and 10 mol % Cl, or 10 mol % Cs, or 10 mol % Cs and 10 mol % Cl have been observed to maintain a cubic Pm3-m cubic crystal structure. FIG. 29 shows x-ray diffraction patterns corresponding to each of the samples presented in Table 1. Tables 2-4 provide the x-ray diffraction peaks and intensity for the three perovskite materials shown in Table 1. The data were collected at ambient conditions on a Rigaku Miniflex 600 using a Cu Kα radiation source at a scan rate of 1.5 degrees 2θ/min.

TABLE 2

10 mol % RbI + 10 mol % PbCl2

| 2-theta (deg) | d (ang.) | Height (cps) | Peak Identity (phase, miller index) |
| --- | --- | --- | --- |
| | | | PbI2, (001) |
| 13.878(3) | 6.3759(15) | 12605(126) | Perovskite, (001) |
| 19.707(15) | 4.501(3) | 489(25) | Perovskite, (011) |
| 21.320(14) | 4.164(3) | 286(19) | ITO, (112) |
| 24.227(19) | 3.671(3) | 1022(36) | Perovskite, (111) |
| 28.017(4) | 3.1822(5) | 5683(84) | Perovskite, (002) |
| 30.13(4) | 2.964(4) | 344(21) | ITO, (112) |
| 31.403(14) | 2.8464(13) | 913(34) | Perovskite, (012) |

TABLE 3

10 mol % CsI & 0 mol % PbCl2

| 2-theta (deg) | d (ang.) | Height (cps) | Peak Identity phase (miller index) |
| --- | --- | --- | --- |
| 12.614(14) | 7.012(8) | 99(11) | PbI2, (001) |
| 13.952(3) | 6.3425(13) | 4921(78) | Perovskite, (001) |
| 19.826(12) | 4.475(3) | 392(22) | Perovskite, (011) |
| 21.274(14) | 4.173(3) | 281(19) | ITO, (112) |
| 24.333(15) | 3.655(2) | 1031(36) | Perovskite, (111) |
| 28.094(7) | 3.1736(8) | 2332(54) | Perovskite, (002) |
| 30.15(4) | 2.962(4) | 364(21) | ITO, (112) |
| 31.531(12) | 2.8351(10) | 941(34) | Perovskite, (012) |

TABLE 4

10 mol % CsI & 10 mol % PbCl2

| 2-theta (deg) | d (ang.) | Height (cps) | Peak Identity phase (miller index) |
| --- | --- | --- | --- |
| 12.635(6) | 7.000(3) | 395(22) | PbI2, (001) |
| 13.985(3) | 6.3272(13) | 13692(131) | Perovskite, (001) |
| 19.867(11) | 4.465(2) | 807(32) | Perovskite, (011) |
| 21.392(13) | 4.150(2) | 254(18) | ITO, (112) |
| 24.41(2) | 3.643(3) | 918(34) | Perovskite, (111) |
| 28.188(4) | 3.1633(4) | 6797(92) | Perovskite, (002) |
| 30.14(4) | 2.963(4) | 348(21) | ITO, (112) |
| 31.633(15) | 2.8262(13) | 1027(36) | Perovskite, (012) |

A geometrically expected x-ray diffraction pattern for cubic Pm3-m material with a lattice constant=6.3375 Å under Cu—Kα radiation is shown in Table 5. As can be seen from the data, the perovskite materials produced with 10 mol % Rb and 10 mol % Cl, 10 mol % Cs, and 10% Cs and 10% Cl each have diffraction patterns conforming to the expected pattern for a cubic, Pm3-m perovskite material.

TABLE 5

Geometrically Expected Diffraction Pattern for Cubic PM3-m, lattice constant = 6.3375 Å; Cu—Kα Radiation)

| 2-Theta (degrees) | d-spacing (angstroms) | Miller Index |
|---|---|---|
| 13.963 | 6.3375 | (0 0 1) |
| 19.796 | 4.4813 | (0 1 1) |
| 24.306 | 3.659 | (1 1 1) |
| 28.138 | 3.1688 | (0 0 2) |
| 31.541 | 2.8342 | (0 1 2) |

Enhanced Perovskite

Figure 5:
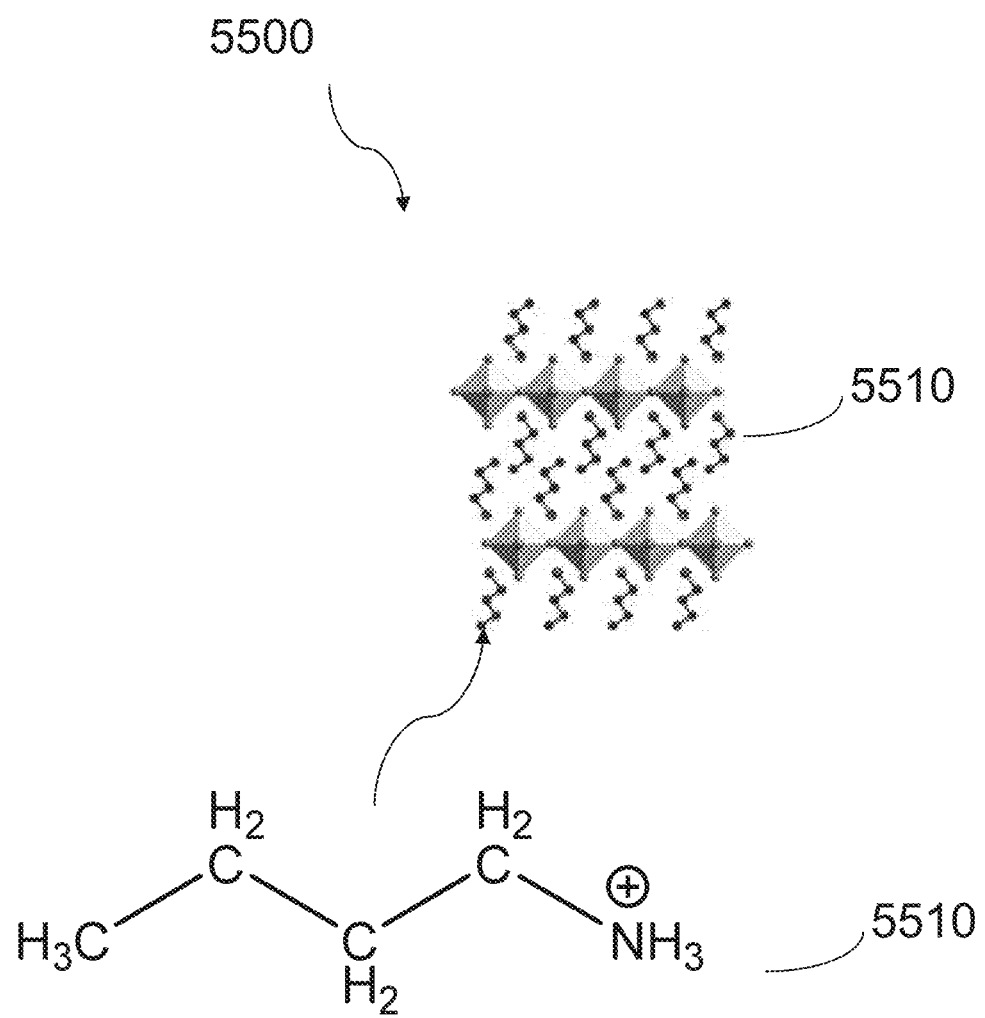
FIG. 5 is a stylized diagram showing an illustration of a Ruddlesden-Popper perovskite.

So-called "layered" 2D perovskites are known to form when perovskites are formulated with organic cations having alkyl chains longer than the methylammonium and formamidinium cations described previously herein. Layered 2D perovskites include structures such as the Ruddlesden-Popper phase, Dion-Jacobson phase, and Aurivillius phase. For example, by substituting 1-butylammonium in place of the methylammonium or the other cations described above, during formation of a perovskite in a "one-step" method (not described herein), a Ruddlesden-Popper 2D perovskite may result. In such perovskites the 1-butylammonium prevents the perovskite from forming a full crystalline lattice, and instead causes the perovskite to form in "sheets" of perovskite having a single crystal structure in thickness. FIG. 5 illustrates a structure of a Ruddlesden-Popper perovskite 5500 with a 1-butylammonium cation 5510. As can be seen from FIG. 5, the "tails" of the butylammonium cation 5510 result in a separation between the lead and iodide portion of the perovskite material and other lead and iodide structures, resulting in "sheets" of 2D perovskites. Accordingly, introduction of "bulky organic" cations, such as 1-butylammonium or benzylammonium during formation of a perovskite material may be undesirable if the Ruddlesden-Popper form of the perovskite is not desired.

Figure 6:
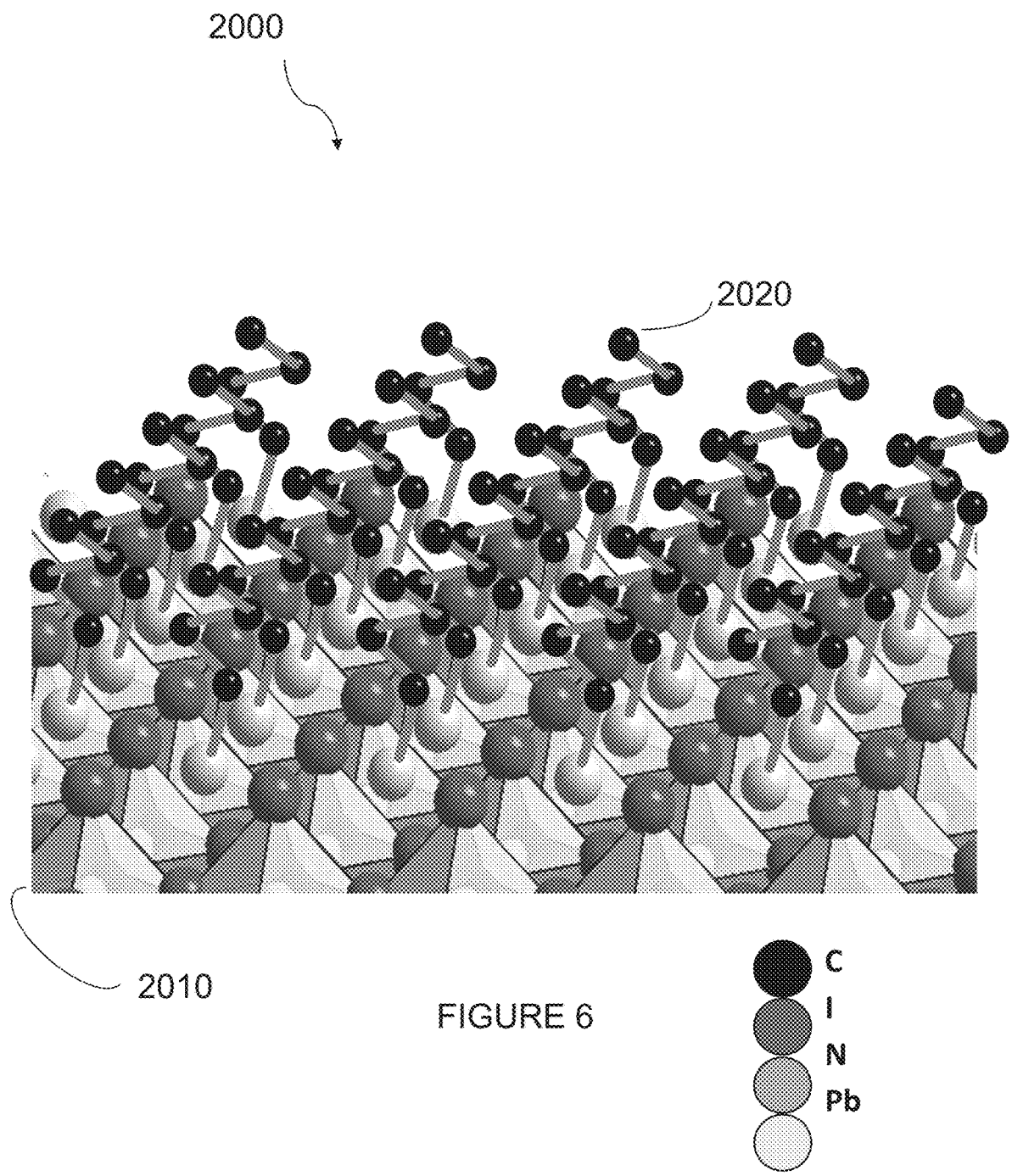
FIG. 6 is a stylized diagram showing an illustration of a perovskite material with addition of an alkyl ammonium cation, according to some embodiments of the present disclosure.
Figure 30:
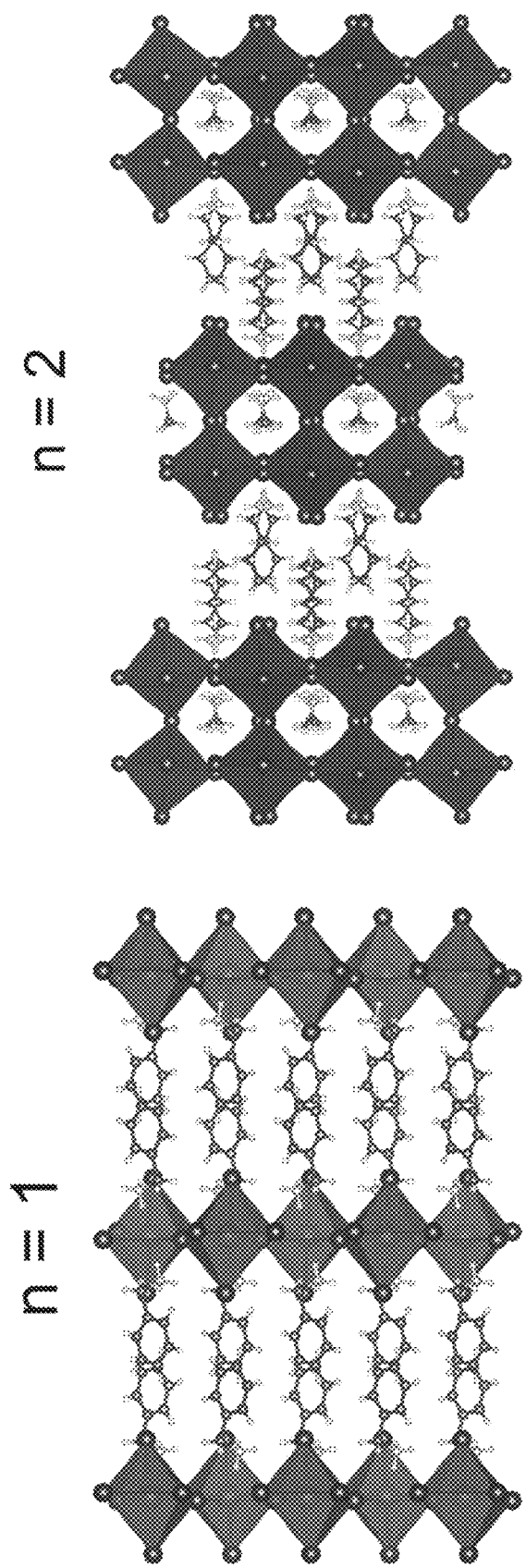
FIG. 30 provides a stylized illustration of thicknesses of inorganic metal halide sublattices of perovskite materials, according to some embodiments of the present disclosure.

However, addition of a dilute amount of 1-butylammonium solution prior to annealing the perovskite material may result in a perovskite as shown in FIG. 6. FIG. 6 illustrates an embodiment of a perovskite material 2000 with addition of an alkyl ammonium cation for surface passivation. In the illustrated embodiment, the surface of a formamidinium lead iodide (FAPbI$_3$) perovskite material 2010 is shown with 1-butylammonium cation 2020 at the surface. The 1-butylammonium cation, or other "bulky" organic cations as described herein, may diffuse into the perovskite material near the surface of the perovskite material crystal lattice, in some embodiments. In particular embodiments, the 1-butylammonium cation, or other "bulky" organic cations as described herein, may reside 50 nm or less into the perovskite material from the crystal lattice surfaces or grain boundaries. The inclusion of "bulky" organic cations, such as 1-butylammonium, near or at the surface of a perovskite material may result in the formula of the perovskite material deviating from the "ideal" stoichiometry of perovskite materials disclosed herein. For example, inclusion of such organic cations may cause the perovskite material to have a formula that is either substoichiometric or superstoichiometric with respect to the CMX$_3$ formula described herein. In this case, the general formula for the perovskite material may be expressed as C$_x$M$_y$X$_z$, where x, y and z are real numbers. In some embodiments, a perovskite material may have the formula C'$_2$C$_{n-1}$M$_n$X$_{3n+1}$, where n is an integer. For example, when n=1 the perovskite material may have the formula C'$_2$MX$_4$, when n=2 the perovskite material may have the formula C'$_2$CM$_2$X$_7$, when n=3 the perovskite material may have the formula C'$_2$C$_2$M$_3$X$_{10}$, when n=4 the perovskite material may have the formula C'$_2$C$_3$M$_4$X$_{13}$, and so on. As illustrated by FIG. 30, the n-value indicates the thickness of an inorganic metal halide sublattice of the perovskite material. A phase of the perovskite material having the formula C'$_2$C$_{n-1}$M$_n$X$_{3n+1}$, may form in regions where a bulky organic cation has diffused into, or otherwise entered into, the crystal lattice of a perovskite material. For example, such a phase may be present within 50 nanometers of a crystal lattice surface (e.g. a surface or grain boundary) of a perovskite material that has been formed including a bulky organic cation as disclosed herein.

The carbon "tails" of the 1-butyl ammonium ion may provide a protective property to the surface of the perovskite by effectively keeping other molecules away from the surface. In some embodiments, the alkyl group "tail" of the 1-butyl ammonium ion may be oriented away from or parallel to the surface of the perovskite material. In particular, the 1-butylammonium "tails" have hydrophobic properties, which prevents water molecules from contacting the surface of the perovskite and protects the surface of the perovskite material 2010 from water in the environment. Additionally, the 1-butylammonium cations may also act to passivate the surface and any grain boundaries or defects with the perovskite material 2010. Passivation refers to an electrical characteristic that prevents charge accumulation or "trap states" at the surface or grain boundaries of the perovskite material 2010. By acting to passivate portions of perovskite material 2010 the 1-butylammonium may facilitate improved charge transfer in and out of the perovskite material 2010 and improve the electrical properties of the photoactive layer.

In some embodiments, other organic cations may be applied in place of, or in combination with, 1-butylammonium. Examples of other "bulky organic" organic cations that may act as to surface passivate perovskite material, include, but are not limited to, ethylammonium, propylammonium, n-butylammonium; perylene n-butylamine-imide; butane-1,4-diammonium; 1-pentylammonium; 1-hexylammonium; poly(vinylammonium); phenylethylammonium; benzyl ammonium; 3-phenyl-1-propylammonium; 4-phenyl-1-butylammonium; 1,3-dimethylbutylammonium; 3,3-dimethylbutylammonium; 1-heptylammonium; 1-octylammonium; 1-nonylammonium; 1-decylammonium; and 1-icosanyl ammonium. Additionally, bulky organic cations with a tail that contains one or more heteroatoms in addition to the cationic species, the heteroatom may coordinate with, bind to, or integrate with the perovskite material crystal lattice. A heteroatom may be any atom in the tail that is not hydrogen or carbon, including nitrogen, sulfur, oxygen, or phosphorous.

Other examples of "bulky" organic cations may include the following molecules functionalized with an ammonium group, phosphonium group, or other cationic group that may integrate into a surface "C-site of a perovskite material: benzene, pyridine, naphthalene, anthracene, xanthene, phenathrene, tetracene chrysene, tetraphene, benzo[c]phenathrene, triphenylene, pyrene, perylene, corannulene, coronene, substituted dicarboxylic imides, aniline, N-(2-aminoethyl)-2-isoindole-1,3-dione, 2-(1-aminoethyl)naphthalene, 2-triphenylene-O-ethylamine ether, benzylamine, benzylammonium salts, N-n-butyl-N'-4-aminobutylperylene-3,4,9,10-bis(dicarboximide), 1-(4-alkylphenyl)methanamine, 1-(4-alkyl-2-phenyl)ethanamine, 1-(4-alkylphenyl)methanamine, 1-(3-alkyl-5-alkylphenyl)methanamine, 1-(3-alkyl-5-alkyl-2-phenyl)ethanamine, 1-(4-alkyl-2-phenyl)ethanamine, 2-Ethylamine-7-alkyl-Naphthalene, 2-Ethylamine-6-alkyl-Naphthalene, 1-Ethylamine-7-alkyl-Naphthalene, 1-Ethylamine-6-alkyl-Naphthalene, 2-Methylamine-7-alkyl-Naphthalene, 2-Methylamine-6-alkyl-Naphthalene, 1-Methylamine-7-alkyl-Naphthalene, 1-Methylamine-6-alkyl-Naphthalene, N-n-aminoalkyl-N'-4-aminobutylperylene-3,4,9,10-bis(dicarboximide), 1-(3-Butyl-5-methoxybutylphenyl)methanamine, 1-(4-Pentylphenyl)methanamine, 1-[4-(2-Methylpentyl)-2-phenyl]ethanamine, 1-(3-Butyl-5-pentyl-2-phenyl)ethanamine, 2-(5-[4-Methylpentyl]-2-naphthyl)ethanamine, N-7-tridecyl-N'-4-aminobutylperylene-3,4,9,10-bis(dicarboximide), N-n-heptyl-N'-4-aminobutylperylene-3,4,9,10-bis(dicarboximide), 2-(6-[3-Methoxylpropyl]-2-naphthyl)ethanamine. FIGS. 17-28 provide illustrations of the structures of these organic molecules, according to certain embodiments. With respect to FIGS. 17 and 18, each "R-group," $R_x$ may be any of H, R', Me, Et, Pr, Ph, Bz, F, Cl, Br, I, $NO_2$, OR', $NR'_2$, SCN, CN, $N_3$, SR', where R' may be any alkyl, alkenyl, or alkynyl chain. Additionally, at least one of the illustrated $R_x$ groups may be $(CH_2)_n EX_y$ or $(CH_2)_n C(EX_y)_2$ where n and y=0, 1, 2, or greater, n and y may or may not be equal, E is selected from the group consisting of C, Si, O, S, Se, Te, N, P, As, or B, and X is a halide or pseudohalide such as F, Cl, Br, I, CN, SCN, or H. Further, with respect to FIG. 19, the illustrated molecules may include any hydrohalide of each illustrated amine, for example benzylammonium salts, where the illustrated X group may be F, Cl, Br, I, SCN, CN, or any other pseudohalide. Other non-halide acceptable anions may include: nitrate, nitrite, carboxylate, acetate, acetonyl acetonate, formate, oxalate, sulfate, sulfite, thiosulfate, phosphate, tetrafluoroborate, hexafluorophosphate, tetra(perfluorophenyl) borate, hydride, oxide, peroxide, hydroxide, nitride, arsenate, arsenite, perchlorate, carbonate, bicarbonate, chromate, dichromate, iodate, bromate, chlorate, chlorite, hypochlorite, hypobromite, cyanide, cyanate, isocyanate, fulminate, thiocyanate, isothiocyanate, azide, tetracarbonylcobaltate, carbamoyldicyanomethanide, dicyanonitrosomethanide, dicyanamide, tricyanomethanide, amide, and permanganate. Suitable R groups may also include, but are not limited to: hydrogen, methyl, ethyl, propyl, butyl, pentyl group or isomer thereof; any alkane, alkene, or alkyne CxHy, where x=1-20, y=1-42, cyclic, branched or straight-chain; alkyl halides, CxHyXz, x=1-20, y=0-42, z=1-42, X=F, Cl, Br, or I; any aromatic group (e.g., phenyl, alkylphenl, alkoxyphenyl, pyridine, naphthalene); cyclic complexes where at least one nitrogen is contained within the ring (e.g., pyridine, pyrrole, pyrrolidine, piperidine, tetrahydroquinoline); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (e.g., acetic acid, propanoic acid); and ester or amide derivatives thereof; any amino acid (e.g., glycine, cysteine, proline, glutamic acid, arginine, serine, histidine, 5-ammoniumvaleric acid) including alpha, beta, gamma, and greater derivatives; any silicon containing group (e.g., siloxane); and any alkoxy or group, —OCxHy, where x=0-20, y=1-42.

Figure 7:
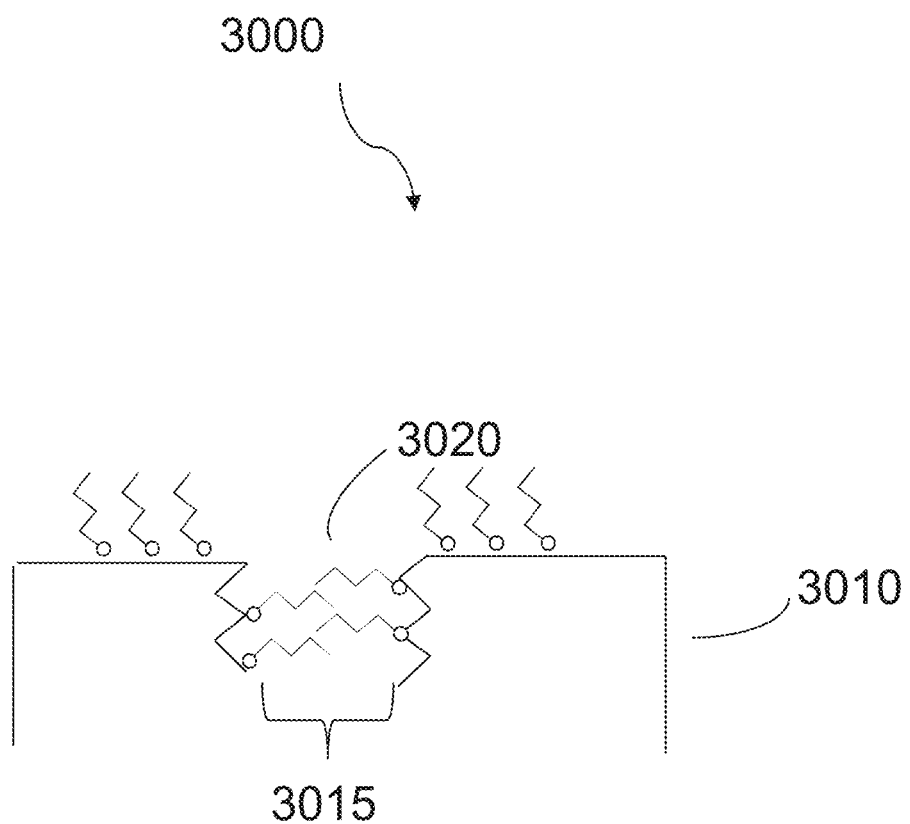
FIG. 7 is a stylized diagram showing an illustration of a perovskite material with a 1-butylammonium surface layer, according to some embodiments of the present disclosure.

Additionally, in some embodiments, the bulky organic cation may passivate grain boundaries and surface defects in the perovskite material. FIG. 7 illustrates an example embodiment of a perovskite material layer 3000 with 1-butylammonium 3020 passivating both the surface and grain boundaries 3015 of a bulk perovskite material 3010. As described above, the alkyl tails of these ions may also form a hydrophobic layer which repels water and other polar species and impedes such species from reaching the surface of the perovskite material. As can be seen in FIG. 7, the "tails" of the bulky organic cations may not be chemically connected (e.g., covalently or ionically bonded) to the surface or grain boundaries 3015 of the perovskite material layer 3000. As used herein, "tails" of any bulky organic cation refers to the non-ionic carbon structure of the bulky organic cation. For example, the tail of 1-butylammonium is the butyl group and the tail of benzylammonium is the benzyl group.

The tails of the bulky organic cation may also assume other arrangements with respect to the surface or grain boundary of a perovskite material. Generally, the cationic "head" of a bulky organic cation will not diffuse more than 50 nanometers past the surface or a grain boundary of a perovskite material. The tail may interact weakly with the perovskite material and be oriented away from the perovskite material crystal grain surface. The tail may have an intermolecular interaction (e.g., dipole-dipole or hydrogen bonding) with the perovskite material crystal grain surface resulting in a configuration where the tail is oriented towards the perovskite material crystal grain surface. In some embodiments, the tails of some bulky organic cations present in the perovskite material may not interact with the surfaces or grain boundaries of the perovskite material and the tails of other bulky organic cations in the perovskite material may interact with the surfaces or grain boundaries of the perovskite material. The tail may contain a heteroatom or anion (i.e., a zwitterion) with at least one electron lone pair that may interact covalently (e.g., a coordination covalent bond) with the perovskite material crystal grain surface via a metal atom (e.g., Pb, Sn, Ge, In, Bi, Cu, Ag, Au) present in the perovskite material. The tail may also include a cationic species, such as diammonium butane as described herein, that may incorporate into the perovskite material by substituting on at least two "C" cation sites (such as formamidinium). A tail including a cationic species may also bridge two layers of a 2D perovskite material, lie prone across the perovskite material crystal grain surface, or orient away from the perovskite material crystal grain surface in a similar manner to that described with respect to a non-ionic tail. In another embodiment, a bulky organic cation having a sufficiently bulky tail, such as an imidazolium cation, may simply reside on the perovskite surface or grain boundary without diffusing into the perovskite material.

Figure 8:
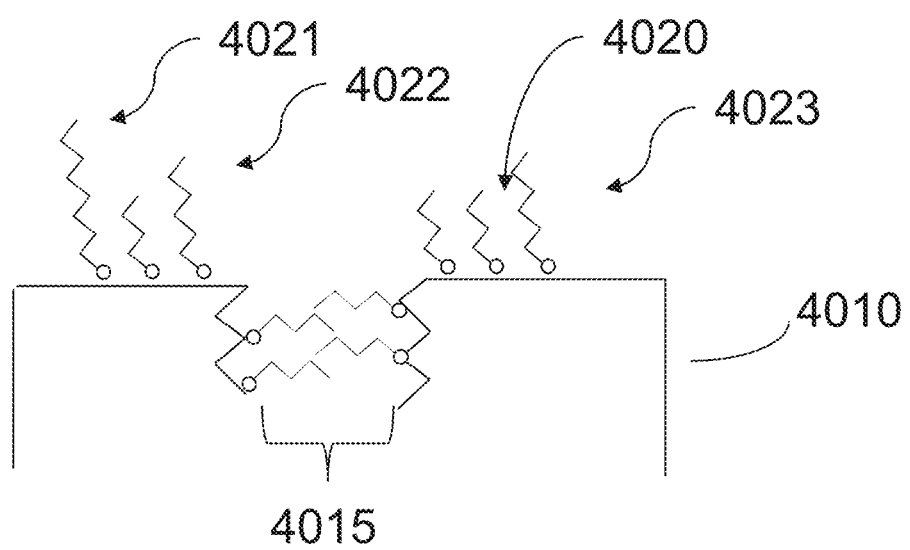
FIG. 8 is a stylized diagram showing an illustration of a perovskite material with a surface layer of multiple bulky organic cations, according to some embodiments of the present disclosure.
Figure 8A:
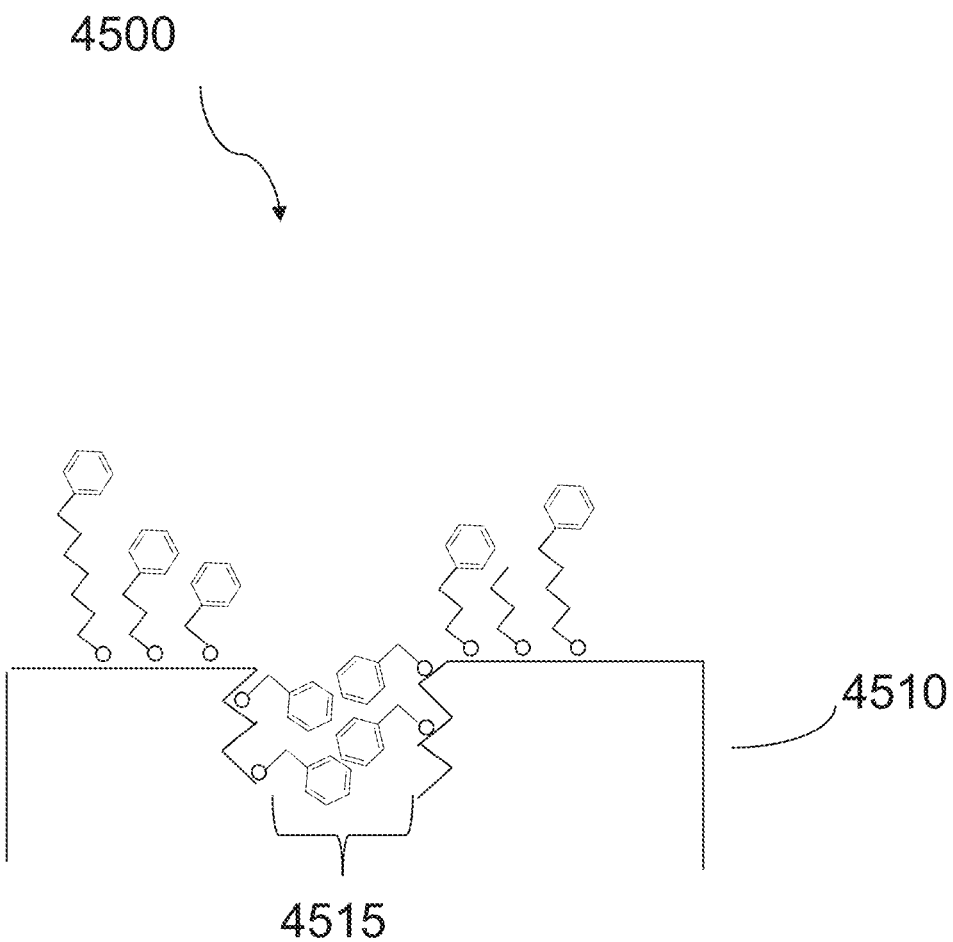
FIG. 8A is a stylized diagram showing an illustration of a perovskite material with a surface layer of multiple bulky organic cations, according to some embodiments of the present disclosure.

Additionally, in other embodiments, the bulky organic cations with tail groups that vary in length or size may be applied to the perovskite to passivate grain boundaries and surface defects in the perovskite material. FIG. 8 illustrates an example embodiment of a perovskite material layer 4000 with a combination of 1-butylammonium 4020, 1-nonylammonium 4021, 1-heptylammonium 4022, and 1-hexyl ammonium 4023 passivating both the surface and grain boundaries 4015 of a bulk perovskite material 4010. In particular embodiments, any mixture of the alkylammonium compounds identified above may be applied to a perovskite material as described herein. FIG. 8 illustrates an example embodiment of a perovskite material layer 4000 with a combination of 1-butylammonium 4020, 1-nonylammonium 4021, 1-heptylammonium 4022, and 1-hexyl ammonium 4023 passivating both the surface and grain boundaries 4015 of a bulk perovskite material 4010. In particular embodiments, any mixture of the alkylammonium compounds identified above may be applied to a perovskite material as described herein. In some embodiments bulky organic cations may include a benzyl group. FIG. 8A illustrates an example embodiment of a perovskite material layer 4500 with a variety of bulky organic cations containing benzyl groups passivating both the surface and grain boundaries 4515 of a bulk perovskite material 4510.

Figure 9:
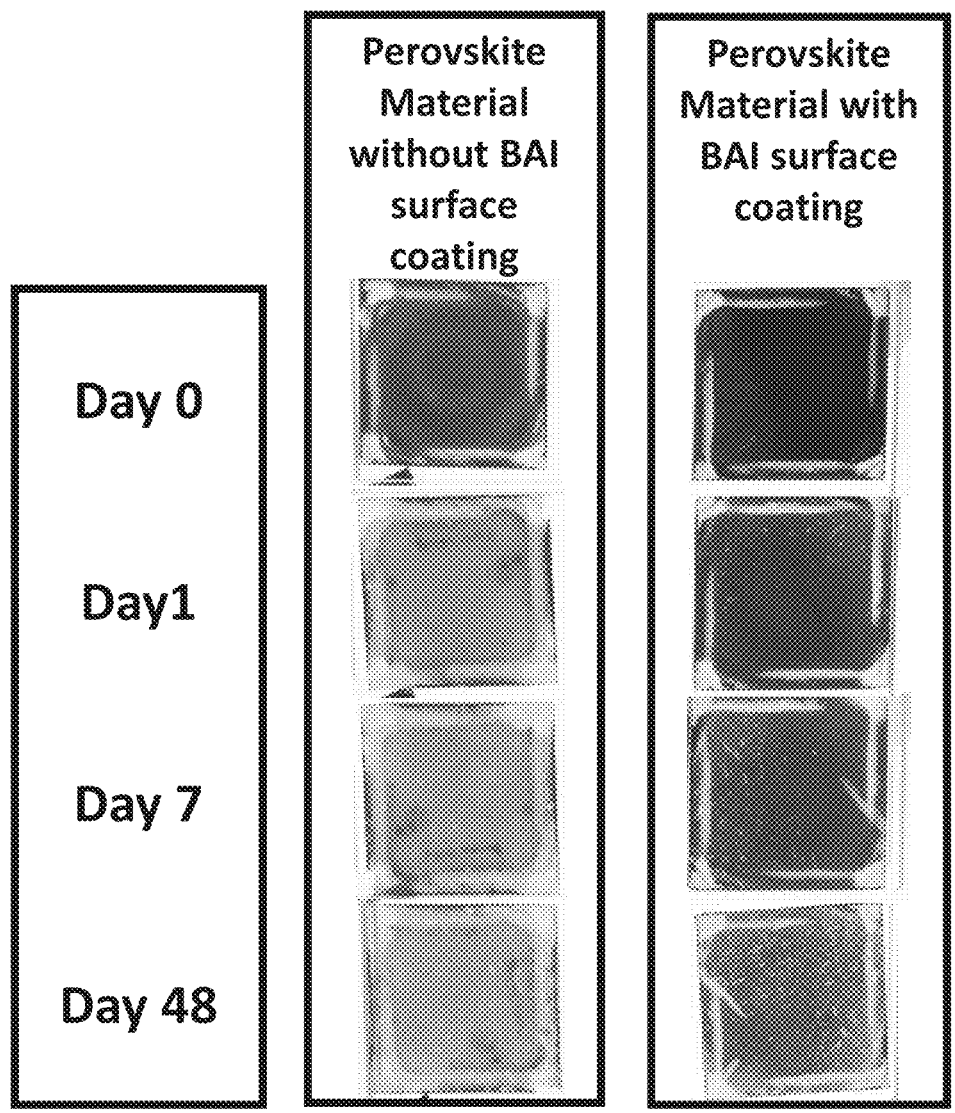
FIG. 9 is an illustration of a comparison of images taken of a perovskite material with and without a 1-butylammonium ("BAI") surface coating, according to some embodiments of the present disclosure.

Addition of a 1-butylammonium surface coating to a perovskite material as described above has been shown to increase the high temperature durability of the perovskite in damp environments. FIG. 9 shows a comparison of images taken of a perovskite material with and without a 1-butylammonium ("BAI") surface coating over a period of 48 days. Both perovskite materials had the same composition and were exposed to an environment having a temperature of 85° C. at 55% relative humidity for 48 days. As can be seen from the photographs, the perovskite material having no 1-butylammonium surface coating lightens in color significantly after one day of exposure to the environment, indicating that the perovskite material has degraded significantly. The perovskite material having the 1-butylammonium surface coating shows a gradual lightening of color over 48 days and remains partially dark after 48 days. This indicates that the perovskite material with the 1-butylammonium surface coating is more robust than a perovskite material without a 1-butylammonium surface coating during extended exposure to a high-temperature environment.

Figure 10:
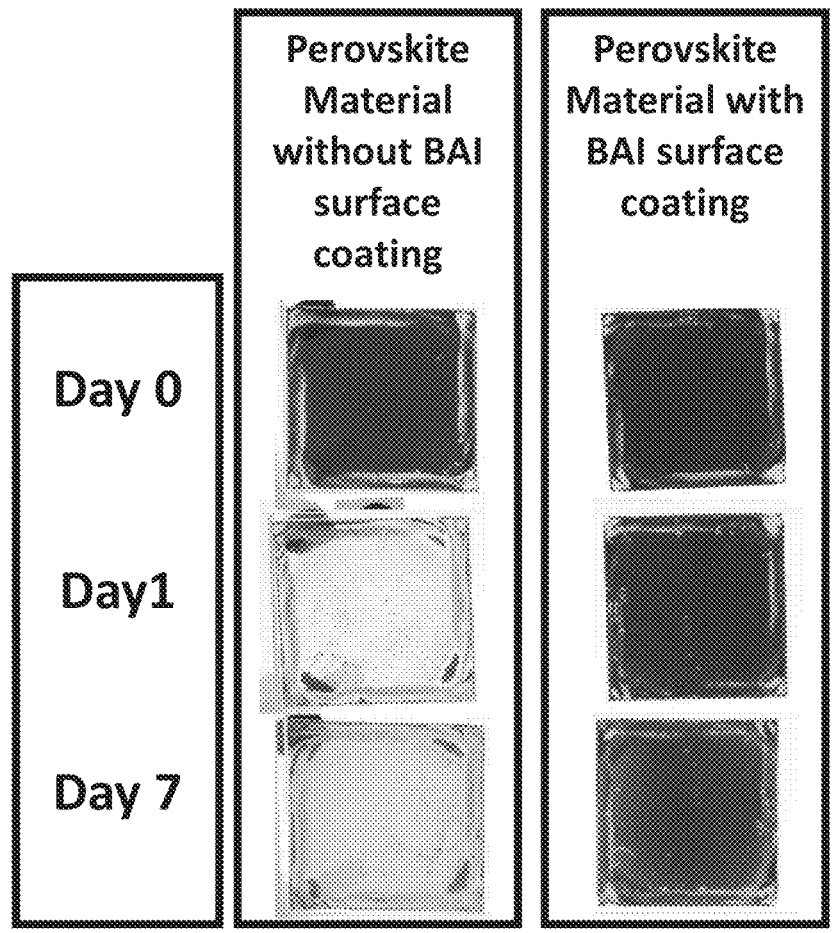
FIG. 10 is a stylized diagram showing an illustration of a comparison of images taken of a perovskite material with and without a 1-butylammonium ("BAI") surface coating, according to some embodiments of the present disclosure.
Figure 11A:
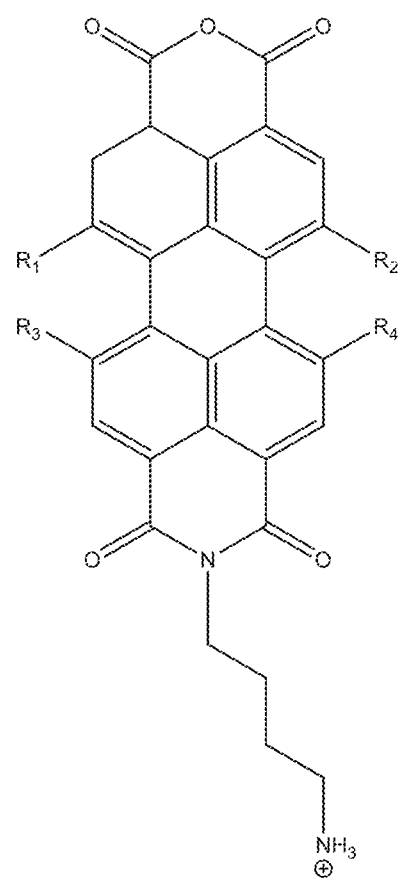
FIGS. 11A-D illustrate various perylene monoimides and diimides that may be applied to the surface of a perovskite material, according to some embodiments of the present disclosure.
Figure 11B:
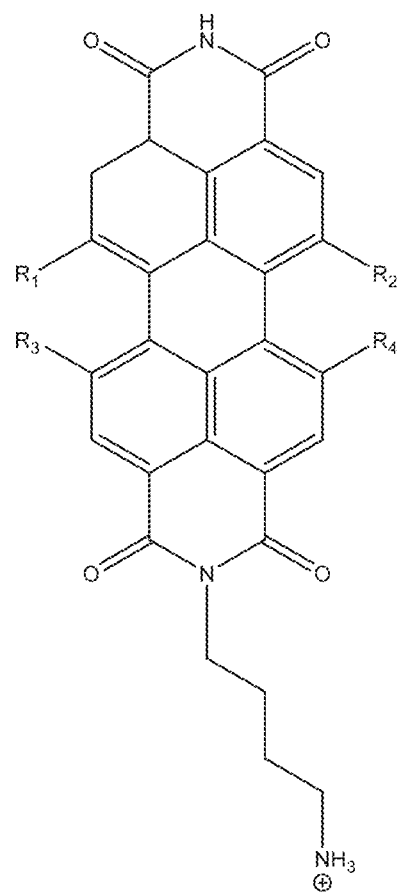
Figure 11C:
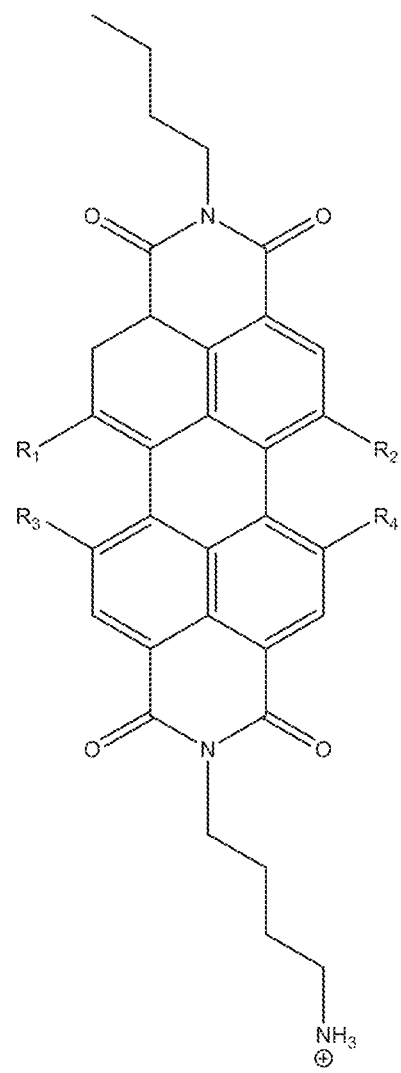
Figure 11D:
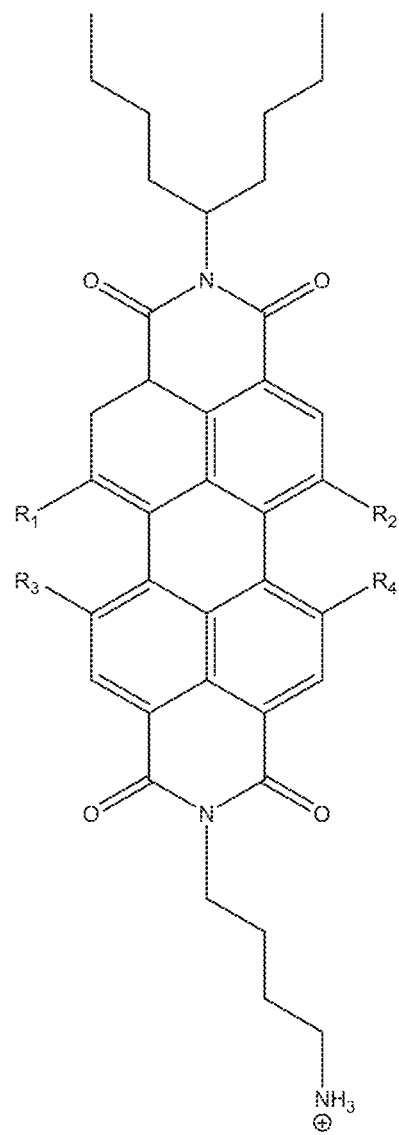

FIG. 10 shows a comparison of images taken of a perovskite material with and without a 1-butylammonium ("BAI") surface coating over a period of seven days. Both perovskite materials had the same composition and were exposed to an environment having a temperature of 85° C. at 0% relative humidity for 7 days. As can be seen from the photographs, the perovskite material having no 1-butylammonium surface coating lightens in color significantly after one day of exposure to the environment, indicating that the perovskite material has degraded significantly. The perovskite material having the 1-butylammonium surface coating shows very little change in color after seven days. This indicates that the perovskite material with the 1-butylammonium surface coating did not completely break down during extended exposure to a high-temperature, high-humidity environment.

Figure 12:
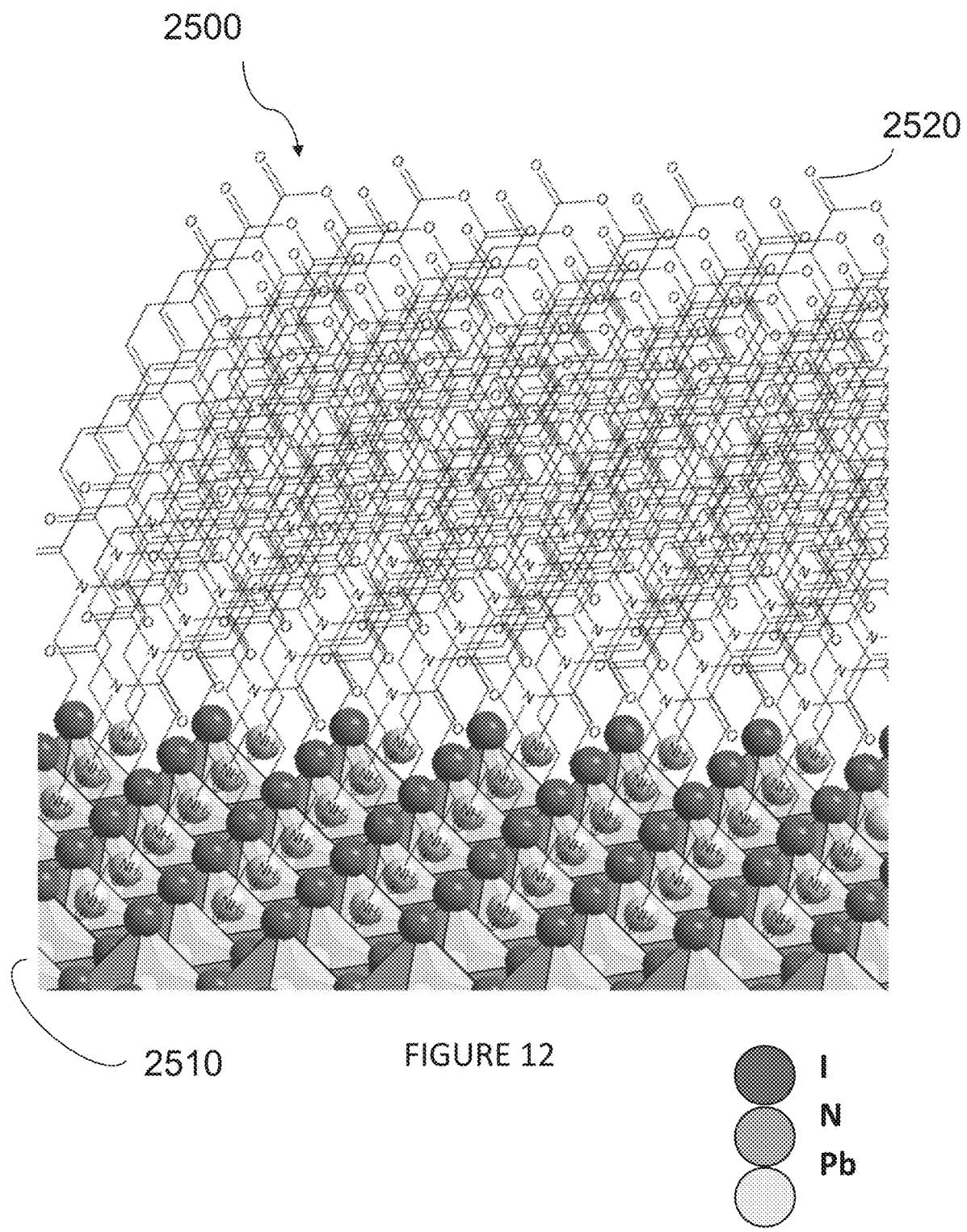
FIG. 12 is a stylized diagram showing an illustration of a perovskite material with addition of a perylene monoimides ammonium cation, according to some embodiments of the present disclosure.

In other embodiments, perylene n-butylamine-imide may be applied to the surface of a perovskite material as described above with respect to 1-butylammonium. FIGS. 11A-D illustrate various perylene monoimides and diimides that may be applied to the surface of a perovskite material according to the present disclosure. FIG. 12 illustrates an embodiment of a perovskite material 2500 with addition of an alkyl ammonium cation for surface passivation. In the illustrated embodiment, the surface of a formamidinium lead iodide (FAPbI$_3$) perovskite material 2510 is shown with perylene n-butylamine-imide 2520 at the surface. As with the 1-butylammonium illustrated in FIG. 6, the carbon "tails" of the perylene n-butylamine-imide ion may provide a protective property to the surface of the perovskite by effectively keeping other molecules away from the surface. In particular, the perylene n-butylamine-imide "tails" have hydrophobic properties, which prevents water molecules from contacting the surface of the perovskite and protects the surface of the perovskite material 2510 from water in the environment. Additionally, the perylene n-butylamine-imide cations may also act to passivate the surface and any grain boundaries or defects with the perovskite material 2510. By acting to passivate portions of perovskite material 2510 the perylene n-butylamine-imide may facilitate improved charge transfer in and out of the perovskite material 2510 and improve the electrical properties of the photoactive layer.

An example method for depositing the 1-butylammonium prior to annealing the perovskite material is described below.

First, a lead halide precursor ink is formed. An amount of lead halide may be massed in a clean, dry vessel in a controlled atmosphere environment (e.g., controlled atmosphere box with glove-containing portholes allows for materials manipulation in an air-free environment). Suitable lead halides include, but are not limited to, lead (II) iodide, lead (II) bromide, lead (II) chloride, and lead (II) fluoride. The lead halide may comprise a single species of lead halide or it may comprise a lead halide mixture in a precise ratio. In certain embodiments, the lead halide mixture may comprise any binary, ternary, or quaternary ratio of 0.001-100 mol % of iodide, bromide, chloride, or fluoride. In one embodiment, the lead halide mixture may comprise lead (II) chloride and lead (II) iodide in a ratio of about 10:90 mol:mol. In other embodiments, the lead halide mixture may comprise lead (II) chloride and lead (II) iodide in a ratio of about 5:95, about 7.5:92.5, or about 15:85 mol:mol.

Alternatively, other lead salt precursors may be used in conjunction with or in lieu of lead halide salts to form the precursor ink. Suitable precursor salts may comprise any combination of lead (II) or lead (IV) and the following anions: nitrate, nitrite, carboxylate, acetate, acetonyl acetonate, formate, oxalate, sulfate, sulfite, thiosulfate, phosphate, tetrafluoroborate, hexafluorophosphate, tetra(perfluorophenyl) borate, hydride, oxide, peroxide, hydroxide, nitride, arsenate, arsenite, perchlorate, carbonate, bicarbonate, chromate, dichromate, iodate, bromate, chlorate, chlorite, hypochlorite, hypobromite, cyanide, cyanate, isocyanate, fulminate, thiocyanate, isothiocyanate, azide, tetracarbonylcobaltate, carbamoyldicyanomethanide, dicyanonitrosomethanide, dicyanamide, tricyanomethanide, amide, and permanganate.

The precursor ink may further comprise a lead (II) or lead (IV) salt in mole ratios of 0 to 100% to the following metal ions Be, Mg, Ca, Sr, Ba, Fe, Cd, Co, Ni, Cu, Ag, Au, Hg, Sn, Ge, Ga, In, Tl, Sb, Bi, Ti, Zn, Cd, Hg, and Zr as a salt of the aforementioned anions.

A solvent may then be added to dissolve the lead solids to form the lead halide precursor ink. Suitable solvents include, but are not limited to, dry N-cyclohexyl-2-pyrrolidone, alkyl-2-pyrrolidone, dimethylformamide, dialkylformamide, dimethylsulfoxide (DMSO), methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, alkylnitrile, arylnitrile, acetonitrile, alkoxylalcohols, alkoxyethanol, 2-methoxyethanol, glycols, propylene glycol, ethylene glycol, and combinations thereof. In one embodiment, the lead solids are dissolved in dry dimethylformamide (DMF). The lead solids may be dissolved at a temperature between about 20° C. to about 150° C. In some embodiments, the solvent may further comprise 2-methoxyethanol and acetonitrile. In some embodiments, 2-methoxyethanol and acetonitrile may be added in a volume ratio of from about 25:75 to about 75:25, or at least 25:75. In certain embodiments, the solvent may include a ratio of 2-methoxyethanol and acetonitrile to DMF of from about 1:100 to about 1:1, or from about 1:100 to about 1:5, on a volume basis. In certain embodiments, the solvent may include a ratio of 2-methoxyethanol and acetonitrile to DMF of at least about 1:100 on a volume basis. In one embodiment, the lead solids are dissolved at about 85° C. The lead solids may be dissolved for as long as necessary to form a solution, which may take place over a time period up to about 72 hours. The resulting solution forms the base of the lead halide precursor ink. In some embodiments, the lead halide precursor ink may have a lead halide concentration between about 0.001M and about 10M. In one embodiment, the lead halide precursor ink has a lead halide concentration of about 1 M.

Optionally, certain additives may be added to the lead halide precursor ink to affect the final perovskite crystallinity and stability. In some embodiments, the lead halide precursor ink may further comprise an amino acid (e.g., 5-aminovaleric acid, histidine, glycine, lysine), an amino acid hydrohalide (e.g., 5-amino valeric acid hydrochloride), an IFL surface-modifying (SAM) agent (such as those discussed earlier in the specification), or a combination thereof. In one embodiment, formamidinium chloride may be added to the lead halide precursor ink. In other embodiments, the halide of any cation discussed earlier in the specification may be used. In some embodiments, combinations of additives may be added to the lead halide precursor ink including, for example, the combination of formamidinium chloride and 5-amino valeric acid hydrochloride.

The additives, including formamidinium chloride and/or 5-amino valeric acid hydrochloride may be added to the lead halide precursor ink at various concentrations depending on the desired characteristics of the resulting perovskite material. In one embodiment, the additives may be added in a concentration of about 1 nM to about 1 M. In another embodiment, the additives may be added in a concentration of about 1 µM to about 1 M. In another embodiment, the additives may be added in a concentration of about 1 µM to about 1 mM.

In some embodiments, a Group 1 metal halide solution is formed to be added to the lead halide precursor ink. An amount of Group 1 metal halide may be massed in a clean, dry vessel in a controlled atmosphere environment. Suitable Group 1 metal halides include, but are not limited to, cesium iodide, cesium bromide, cesium chloride, cesium fluoride, rubidium iodide, rubidium bromide, rubidium chloride, rubidium fluoride, lithium iodide, lithium bromide, lithium chloride, lithium fluoride, sodium iodide, sodium bromide, sodium chloride, sodium fluoride, potassium iodide, potassium bromide, potassium chloride, potassium fluoride. The Group 1 metal halide may comprise a single species of Group 1 metal halide or it may comprise a Group 1 metal halide mixture in a precise ratio. In one embodiment the Group 1 metal halide may comprise cesium iodide. In another embodiment the Group 1 metal halide may comprise rubidium iodide. In another embodiment the Group 1 metal halide may comprise sodium iodide. In another embodiment the Group 1 metal halide may comprise potassium iodide.

Alternatively, other Group 1 metal salt precursors may be used in conjunction with or in lieu of Group 1 metal halide salts to form a Group 1 metal salt solution. Suitable precursor Group 1 metal salts may comprise any combination of Group 1 metals and the following anions: nitrate, nitrite, carboxylate, acetate, formate, oxalate, sulfate, sulfite, thiosulfate, phosphate, tetrafluoroborate, hexafluorophosphate, tetra(perfluorophenyl) borate, hydride, oxide, peroxide, hydroxide, nitride, arsenate, arsenite, perchlorate, carbonate, bicarbonate, chromate, dichromate, iodate, bromate, chlorate, chlorite, hypochlorite, hypobromite, cyanide, cyanate, isocyanate, fulminate, thiocyanate, isothiocyanate, azide, tetracarbonylcobaltate, carbamoyldicyanomethanide, dicyanonitrosomethanide, dicyanamide, tricyanomethanide, amide, and permanganate.

A solvent may then be added to the vessel to dissolve the Group 1 metal halide solids to form the Group 1 metal halide solution. Suitable solvents include, but are not limited to, dry N-cyclohexyl-2-pyrrolidone, alkyl-2-pyrrolidone, dimethylformamide (DMF), dialkylformamide, dimethylsulfoxide (DMSO), methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations thereof. In one embodiment, the lead solids are dissolved in dry dimethylsulfoxide (DMSO). The Group 1 metal halide solids may be dissolved at a temperature between about 20° C. to about 150° C. In one embodiment, the Group 1 metal halide solids are dissolved at room temperature (i.e. about 25° C.). The Group 1 metal halide solids may be dissolved for as long as necessary to form a solution, which may take place over a time period up to about 72 hours. The resulting solution forms the Group 1 metal halide solution. In some embodiments, the Group 1 metal halide solution may have a Group 1 metal halide concentration between about 0.001M and about 10M. In one embodiment, the Group 1 metal halide solution has a Group 1 metal halide concentration of about 1 M. In some embodiments, the Group 1 metal halide solution may further comprise an amino acid (e.g., 5-aminovaleric acid, histidine, glycine, lysine), an amino acid hydrohalide (e.g., 5-amino valeric acid hydrochloride), an IFL surface-modifying (SAM) agent (such as those discussed earlier in the specification), or a combination thereof.

Next, the lead halide solution and the Group 1 metal halide solution are mixed to form a thin-film precursor ink. The lead halide solution and Group 1 metal halide solution may be mixed in a ratio such that the resulting thin-film precursor ink has a molar concentration of the Group 1 metal halide that is between 0% and 25% of the molar concentration of the lead halide. In particular embodiments, the thin-film precursor ink may have a molar concentration of the Group 1 metal halide that is 1% of the molar concentration of the lead halide. In particular embodiments, the thin-film precursor ink may have a molar concentration of the Group 1 metal halide that is 5% of the molar concentration of the lead halide. In particular embodiments, the thin-film precursor ink may have a molar concentration of the Group 1 metal halide that is 10% of the molar concentration of the lead halide. In particular embodiments, the thin-film precursor ink may have a molar concentration of the Group 1 metal halide that is 15% of the molar concentration of the lead halide. In particular embodiments, the thin-film precursor ink may have a molar concentration of the Group 1 metal halide that is 20% of the molar concentration of the lead halide. In particular embodiments, the thin-film precursor ink may have a molar concentration of the Group 1 metal halide that is 25% of the molar concentration of the lead halide. In some embodiments the lead halide solution and the Group 1 metal halide solution may be stirred or agitated during or after mixing.

Optionally, in certain embodiments, water may be added to the lead halide precursor ink. In some embodiments, the solvent may further comprise 2-methoxyethanol and acetonitrile. In some embodiments, 2-methoxyethanol and acetonitrile may be added in a volume ratio of from about 25:75 to about 75:25, or at least 25:75. In certain embodiments, the solvent may include a ratio of 2-methoxyethanol and acetonitrile to DMF of from about 1:100 to about 1:1, or from about 1:100 to about 1:5, on a volume basis. In certain embodiments, the solvent may include a ratio of 2-methoxyethanol and acetonitrile to DMF of at least about 1:100 on a volume basis. By way of explanation, and without limiting the disclosure to any particular theory or mechanism, the presence of water affects perovskite thin-film crystalline growth. Under normal circumstances, water may be absorbed as vapor from the air. However, it is possible to control the perovskite PV crystallinity through the direct addition of water to the lead halide precursor ink in specific concentrations. Suitable water includes distilled, deionized water, or any other source of water that is substantially free of contaminants (including minerals). It has been found, based on light I-V sweeps, that the perovskite PV light-to-power conversion efficiency may nearly triple with the addition of water compared to a completely dry device.

The water may be added to the lead halide precursor ink at various concentrations depending on the desired characteristics of the resulting perovskite material. In one embodiment, the water may be added in a concentration of about 1 nL/mL to about 1 mL/mL. In another embodiment, the water may be added in a concentration of about 1 µL/mL to about 0.1 mL/mL. In another embodiment, the water may be added in a concentration of about 1 µL/mL to about 20 µL/mL.

The lead halide precursor ink or the thin film precursor ink may then be deposited on the desired substrate. Suitable substrate layers may include any of the substrate layers identified earlier in this disclosure. As noted above, the lead halide precursor ink or the thin film precursor ink may be deposited through a variety of means, including but not limited to, drop casting, spin casting, blade coating, slot-die printing, screen printing, or ink-jet printing. In certain embodiments, the lead halide precursor ink or the thin film precursor ink may be spin-coated onto the substrate at a speed of about 500 rpm to about 10,000 rpm for a time period of about 5 seconds to about 600 seconds. In one embodiment, the lead halide precursor ink or the thin film precursor ink may be spin-coated onto the substrate at about 3000 rpm for about 30 seconds. In some embodiments, multiple subsequent depositions of the precursor ink may be made to form a thin-film layer. The lead halide precursor ink or the thin film precursor ink may be deposited on the substrate at an ambient atmosphere in a humidity range of about 0% relative humidity to about 50% relative humidity. The lead halide precursor ink or the thin film precursor ink may then be allowed to dry in a substantially water-free atmosphere, i.e., less than 30% relative humidity, to form a thin film.

After deposition of the lead halide precursor or thin film precursor, a bulky organic cation as described above (e.g. benzylammonium, phenylethylammonium, ethylammonium, propyl ammonium, n-butylammonium; butane-1,4-diammonium; 1-pentyl ammonium; 1-hexylammonium; poly(vinylammonium); phenylethylammonium; 3-phenyl-1-propylammonium; 4-phenyl-1-butylammonium; 1,3-dimethylbutylammonium; 3,3-dimethylbutylammonium; 1-heptylammonium; 1-octylammonium; 1-nonylammonium; 1-decylammonium; 1-icosanyl ammonium; or any other bulky cation described herein or illustrated in FIGS. 17-28) salt solution may be applied to the thin film resulting from the deposition of the lead salt precursor and the second salt precursor. Bulky organic salts may include halide, nitrate, nitrite, carboxylate, acetate, acetonyl acetonate, formate, oxalate, sulfate, sulfite, thiosulfate, phosphate, tetrafluoroborate, hexafluorophosphate, tetra(perfluorophenyl) borate, hydride, oxide, peroxide, hydroxide, nitride, arsenate, arsenite, perchlorate, carbonate, bicarbonate, chromate, dichromate, iodate, bromate, chlorate, chlorite, hypochlorite, hypobromite, cyanide, cyanate, isocyanate, fulminate, thiocyanate, isothiocyanate, azide, tetracarbonylcobaltate, carbamoyldicyanomethanide, dicyanonitrosomethanide, dicyanamide, tricyanomethanide, amide, and/or permanganate salts of any of the preceding cations. The bulky organic cation salt solution may be formed by dissolving a bulky organic cation salt in a solvent such as an alcohol, dry acetonitrile, N-cyclohexyl-2-pyrrolidone, alkyl-2-pyrrolidone, dimethylformamide (DMF), dialkylformamide, dimethylsulfoxide (DMSO), methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations thereof. In a particular embodiment, the bulky organic cation salt may be dissolved in isopropyl alcohol. In certain embodiments, the bulky organic cation salt solution may have a concentration between 0.0001 M and 1.0 M of the bulky organic cation salt. In other embodiments, the bulky organic cation salt solution may have a concentration between 0.01 M and 0.1 M of the bulky organic cation salt. In particular embodiments, the bulky organic cation salt solution may have a concentration of between 0.02 and 0.05 M of the bulky organic cation salt. In a particular embodiment, the bulky organic cation salt solution may have a concentration of approximately 0.05 M of the bulky organic cation salt. The bulky organic cation salt solution may be deposited onto the perovskite material precursor thin film by any method described herein with respect to solution deposition. These methods may include, spray coating, drop casting, spin casting, blade coating, slot-die printing, screen printing, gravure printing, or ink-jet printing. In one embodiment, the bulky organic cation salt may be 1-butylammonium iodide. In another embodiment, the bulky organic cation salt may be benzylammonium iodide. In yet another embodiment, the bulky organic cation salt may be phenylethylammonium iodide.

The thin film may then be thermally annealed for a time period up to about 24 hours at a temperature of about 20° C. to about 300° C. In one embodiment, the thin film may be thermally annealed for about ten minutes at a temperature of about 50° C. The perovskite material active layer may then be completed by a conversion process in which the precursor film is submerged or rinsed with a solution comprising a solvent or mixture of solvents (e.g., acetonitrile, DMF, isopropanol, methanol, ethanol, butanol, chloroform, chlorobenzene, dimethylsulfoxide, water) and salt (e.g., methylammonium iodide, formamidinium iodide, guanidinium iodide, 1,2,2-triaminovinylammonium iodide, 5-aminovaleric acid hydroiodide) in a concentration between 0.001M and 10M. In certain embodiments, the thin films may also be thermally post-annealed in the same fashion as in the first line of this paragraph.

After the thin film is deposited and, in some embodiments, annealed, a second salt precursor (e.g., formamidinium iodide, formamidinium thiocyanate, or guanidinium thiocyanate) may be deposited onto the lead salt thin film, where the thin film may have a temperature about equal to ambient temperature or have a controlled temperature between 0° C. and 500° C. The second salt precursor may be deposited at ambient temperature or at elevated temperature between about 25° C. and 125° C. The second salt precursor may be deposited by a variety of methods known in the art, including but not limited to spin-coating, blade coating, slot-die printing, ink-jet printing, gravure printing, screen printing, sputtering, PE-CVD, thermal evaporation, or spray coating. In some embodiments, multiple subsequent depositions of the second salt solution may be made to form a thin-film layer. In some embodiments the second salt precursor may be a solution containing one or more solvents. For example, the second salt precursor may contain one or more of dry acetonitrile, N-cyclohexyl-2-pyrrolidone, alkyl-2-pyrrolidone, dimethylformamide, dialkylformamide, dimethylsulfoxide (DMSO), methanol, ethanol, propanol, butanol, tetrahydrofuran, formamide, tert-butylpyridine, pyridine, alkylpyridine, pyrrolidine, chlorobenzene, dichlorobenzene, dichloromethane, chloroform, and combinations thereof.

In some embodiments, any bulky organic cation salt as described herein may be combined with the second salt solution prior to deposition of the second salt solution. In particular embodiments, a bulky organic cation salt solution may be prepared as described above and mixed with the second salt solution prior to deposition of the second salt solution. For example, the bulky organic cation salt solution may have a concentration between 0.0001 M and 1.0 M of the bulky organic cation salt. In other embodiments, the bulky organic cation salt solution may have a concentration between 0.01 M and 0.1 M of the bulky organic cation salt. In particular embodiments, the bulky organic cation salt solution may have a concentration of between 0.02 and 0.05 M of the bulky organic cation salt. In a particular embodiment, the bulky organic cation salt solution may have a concentration of approximately 0.05 M of the bulky organic cation salt. In other embodiments, a bulky organic cation salt solution may be deposited onto a lead halide thin film formed after deposition of a lead halide precursor ink or thin film precursor ink. In another embodiment, a bulky organic cation salt solution may be deposited onto a perovskite precursor thin film after deposition of the second salt solution.

Finally, the substrate with the perovskite material precursor thin film may be annealed. Annealing the substrate may convert the lead salt precursor and second salt precursor to a perovskite material, (e.g. $FAPbI_3$, $GAPb(SCN)_3$, $FASnI_3$), with a surface passivating layer of the bulky organic cation. Annealing may be performed in a variety of atmospheres at ambient pressure (e.g. about one atmosphere (760 Torr), depending on elevation and atmospheric conditions) or at pressures less than atmospheric or ambient (e.g., 1 mTorr to 500 mTorr). An annealing atmosphere may comprise ambient air, a controlled humidity environment (e.g., 0-100 g $H_2O/m^3$ of gas), pure argon, pure nitrogen, pure oxygen, pure hydrogen, pure helium, pure neon, pure krypton, pure $CO_2$ or any combination of the preceding gases. A controlled humidity environment may include an environment in which the absolute humidity or the % relative humidity is held at a fixed value, or in which the absolute humidity or the % relative humidity varies according to predetermined set points or a predetermined function. In particular embodiments, annealing may occur in a controlled humidity environment having a % relative humidity greater than or equal to 0% and less than or equal to 50%. In other embodiments, annealing may occur in a controlled humidity environment containing greater than or equal to 0 g $H_2O/m^3$ gas and less than or equal to 20 g $H_2O/m^3$ gas. In some embodiments, annealing may occur at a temperature greater than or equal to 50° C. and less than or equal to 300° C.

For example, in a particular embodiment, a $FAPbI_3$ perovskite material may be formed by the following process. First a lead (II) halide precursor comprising about a 90:10 mole ratio of $PbI_2$ to $PbCl_2$ dissolved in anhydrous DMF may be deposited onto a substrate by spin-coating, blade coating, or slot-die printing. The lead halide precursor ink may be allowed to dry in a substantially water-free atmosphere, i.e., less than 30% relative humidity or 17 g $H_2O/m^3$, for approximately one hour (+15 minutes) to form a thin film. The thin film may be subsequently thermally annealed for about ten minutes at a temperature of about 50° C. (±10° C.). In other embodiments, the lead halide precursor may be deposited by ink-jet printing, gravure printing, screen printing, blade coating, sputtering, PE-CVD, atomic-layer deposition, thermal evaporation, or spray coating. Next, a 1-butylammonium salt solution having a concentration of 0.05 M in isopropyl alcohol may be deposited onto the lead halide thin film. Next, a formamidinium iodide precursor comprising a 15-100 mg/mL concentration of formamidinium iodide dissolved in anhydrous isopropyl alcohol may be deposited onto the lead halide thin film by spin coating or blade coating. In other embodiments, the formamidinium iodide precursor may be deposited by ink-jet printing, gravure printing, screen printing, slot-die printing, sputtering, PE-CVD, atomic-layer deposition, thermal evaporation, or spray coating. Next, the substrate may be annealed at about 25% relative humidity (about 4 to 7 g $H_2O/m^3$ gas) and between about 100° C. and 200° C. to form a formamidinium lead iodide ($FAPbI_3$) perovskite material, with a surface layer of 1-butylammonium. In alternative embodiments, the 1-butylammonium salt solution may be deposited onto the thin film formed after deposition of the formamidinium iodide precursor. In another embodiment, the 1-butylammonium salt solution may be combined with the lead halide precursor ink prior to deposition of the lead halide precursor ink. In yet another embodiment, the 1-butylammonium salt solution may be combined with the formamidinium iodide precursor prior to deposition of the formamidinium iodide precursor. In yet another embodiment, the 1-butylammonium salt solution may be deposited onto the thin film following deposition of the formamidinium iodide precursor and prior to annealing the thin film and substrate. In yet another embodiment, the 1-butylammonium salt solution may be deposited onto the thin film after annealing the thin film and substrate.

In other embodiments, using the process described above with a lead (II) iodide solution, a cesium iodide solution, a methylammonium (MA) iodide salt solution, and a 1-butylammonium salt solution may result in a perovskite material having the formula of $Cs_iMA_{1-i}PbI_3$, where i equals a number between 0 and 1 with a surface layer of 1-butylammonium. As another example, the using a lead (II) iodide solution, a rubidium iodide solution, a formamidinium (FA) iodide salt solution, and a 1-butylammonium salt solution may result in a perovskite material having the formula of $Rb_iFA_{1-i}PbI_3$, where i equals a number between 0 and 1 with a surface layer of 1-butylammonium layer. As another example, using the process described above with a lead (II) iodide solution, a cesium iodide solution, a formamidinium (FA) iodide salt solution, and a 1-butylammonium salt solution may result in a perovskite material having the formula of $Cs_iFA_{1-i}PbI_3$, where i equals a number between 0 and 1 with a surface layer of 1-butylammonium layer. As another example, the using a lead (II) iodide solution, a potassium iodide solution, a formamidinium (FA) iodide salt solution, and a 1-butylammonium salt solution may result in a perovskite material having the formula of $K_iFA_{1-i}PbI_3$, where i equals a number between 0 and 1 with a surface layer of 1-butylammonium layer. As another example, the using a lead (II) iodide solution, a sodium iodide solution, a formamidinium (FA) iodide salt solution, and a 1-butylammonium salt solution may result in a perovskite material having the formula of Na$_i$FA$_{1-i}$PbI$_3$, where i equals a number between 0 and 1 with a surface layer of 1-butylammonium layer. As another example, the using a lead (II) iodide-lead (II) chloride mixture solution, a cesium iodide solution, a formamidinium (FA) iodide salt solution, and a 1-butylammonium salt solution may result in a perovskite material having the formula of Cs$_i$FA$_{1-i}$PbI$_{3-y}$Cl$_y$, where i equals a number between 0 and 1 and y represents a number between 0 and 3 with a surface layer of 1-butylammonium layer.

In another embodiment, a FAPbI$_3$ perovskite material may be formed by the following process. First a lead (II) halide precursor ink comprising about a 90:10 mole ratio of PbI$_2$ to PbCl$_2$ dissolved in anhydrous DMF may be deposited onto a substrate by spin-coating, blade coating, or slot-die printing. The lead halide precursor ink may be allowed to dry in a substantially water-free atmosphere, i.e., less than 30% relative humidity or 17 g H$_2$O/m$^3$, for approximately one hour (+15 minutes) to form a thin film. The thin film may be subsequently thermally annealed for about ten minutes at a temperature of about 50° C. (±10° C.). In other embodiments, the lead halide precursor may be deposited by ink-jet printing, gravure printing, screen printing, sputtering, PE-CVD, atomic-layer deposition, thermal evaporation, or spray coating. Next, a formamidinium iodide precursor comprising a 15-60 mg/mL concentration of formamidinium iodide dissolved in anhydrous isopropyl alcohol may be deposited onto the lead halide thin film by spin coating or blade coating. In other embodiments, the formamidinium iodide precursor may be deposited by ink-jet printing, gravure printing, screen printing, slot-die printing, sputtering, PE-CVD, atomic-layer deposition, blade coating, thermal evaporation, or spray coating. After depositing the lead halide precursor and formamidinium iodide precursor, a benzylammonium salt solution having a concentration of 0.04 M in isopropyl alcohol may be deposited onto the perovskite material precursor thin film. Next, the substrate may be annealed at about 25% relative humidity (about 4 to 7 g H$_2$O/m$^3$ gas) and between about 100° C. and 200° C. to form a formamidinium lead iodide (FAPbI$_3$) perovskite material, with a surface layer of benzylammonium. In particular embodiments, the benzylammonium salt solution may be deposited onto the lead halide thin film prior to deposition of the formamidinium iodide precursor. In another embodiment, the benzylammonium salt solution may be combined with the lead halide precursor ink prior to deposition of the lead halide precursor ink. In yet another embodiment, the benzylammonium salt solution may be combined with the formamidinium iodide precursor prior to deposition of the formamidinium iodide precursor. In some embodiments, the resulting perovskite material may have a cubic crystal structure in the bulk material away from the surface. The presence of bulky organic cations near the surface of the perovskite material may result in a non-cubic crystal structure near the surface of the perovskite material.

In other embodiments, using the process described above with a lead (II) iodide solution, a cesium iodide solution, a methylammonium (MA) iodide salt solution, and a 1-butylammonium salt solution may result in a perovskite material having the formula of Cs$_i$MA$_{1-i}$PbI$_3$, where i equals a number between 0 and 1 with a surface layer of benzylammonium. As another example, using the process described above with a lead (II) iodide solution, a rubidium iodide solution, a formamidinium (FA) iodide salt solution, and a benzylammonium salt solution may result in a perovskite material having the formula of Rb$_i$FA$_{1-i}$PbI$_3$, where i equals a number between 0 and 1 with a surface layer of benzylammonium layer. As another example, using the process described above with a lead (II) iodide solution, a cesium iodide solution, a formamidinium (FA) iodide salt solution, and a benzylammonium salt solution may result in a perovskite material having the formula of Cs$_i$FA$_{1-i}$PbI$_3$, where i equals a number between 0 and 1 with a surface layer of benzylammonium layer. As another example, using the process described above with a lead (II) iodide solution, a potassium iodide solution, a formamidinium (FA) iodide salt solution, and a benzylammonium salt solution may result in a perovskite material having the formula of K$_i$FA$_{1-i}$PbI$_3$, where i equals a number between 0 and 1 with a surface layer of benzylammonium layer. As another example, using the process described above with a lead (II) iodide solution, a sodium iodide solution, a formamidinium (FA) iodide salt solution, and a benzylammonium salt solution may result in a perovskite material having the formula of Na$_i$FA$_{1-i}$PbI$_3$, where i equals a number between 0 and 1 with a surface layer of benzylammonium r. As another example, using the process described above with a lead (II) iodide-lead (II) chloride mixture solution, a cesium iodide solution, a formamidinium (FA) iodide salt solution, and a benzylammonium salt solution may result in a perovskite material having the formula of Cs$_i$FA$_{1-i}$PbI$_{3-y}$Cl$_y$, where i equals a number between 0 and 1 and y represents a number between 0 and 3 with a surface layer of benzylammonium layer.

A method for producing a perovskite material with benzylammonium is described below. First, a lead iodide precursor ink is prepared by dissolving PbI$_2$, PbCl$_2$, and cesium iodide (CsI) in a mixture of DMF and DMSO solvents. To prepare the lead iodide precursor in, a 1.5 M CsI/DMSO solution is prepared by dissolving CsI in DMSO. The CsI/DMSO solution may be prepared, in a particular embodiment, by stirring CsI into DMSO at a ratio of 1.5 mmol of CsI per 1.0 mL of anhydrous DMSO at room temperature for between 1 hour and 2.5 hours. Next, the aforementioned CsI solution is added to a solution of PbI$_2$, PbCl$_2$, and anhydrous DMF solvent to form a 1.28 M Pb$^{2+}$ solution in which the ratios of Cs to Pb is 1:10 and the ratio of I to Cl is 9:1. In a particular embodiment, the 1.28 M Pb$^{2+}$ solution may be prepared by adding the CsI solution into a vessel containing 1.26 mmol of PbI$_2$, 0.14 mmol of PbCl$_2$, and 1.0 mL of anhydrous DMF solvent for each 93.8 µL of the CsI solution. The Pb$^{2+}$ solution is mixed at a temperature between 50° C. and 100° C. for between 1.5 hour and 2.5 hours before being cooled to form the lead iodide precursor ink. In a particular embodiment, the Pb$^{2+}$ solution may be stirred at 85° C. for two hours before being cooled by stirring the solution in a room temperature environment for one hour. In some embodiments, the lead iodide precursor ink may be filtered prior to deposition of the lead iodide precursor ink. A 0.2 µm filter may be used to filter the lead iodide precursor ink, in a particular embodiment.

Formamidinium iodide (FAI) and benzylammonium iodide (BzAI) solutions are prepared by dissolving FAI and BzAI salts in anhydrous isopropanol (IPA) to form a 0.2 M FAI solution and 0.05 M BzAI solution, respectively. In particular embodiments, both the FAI and BzAI solutions may be held at 75° C. during the following coating process.

Next, the lead iodide precursor ink is deposited onto a substrate and subsequently annealed to form a lead iodide film. In a particular embodiment, the lead iodide precursor ink held at 45° C. may be blade-coated onto a substrate coated with a nickel oxide (NiO) thin film layer and subsequently annealed at 50° C. for 10 minutes to form the lead iodide film.

Next, to form the perovskite material layer, the lead iodide film is first underwashed with one coat of the BzAI solution, followed by three coats of the FAI solution. Following deposition of each of the coats of BzAI solution and FAI solution, the coat is allowed to dry prior to deposition of the following coating. In particular embodiments, both the BzAI and the FAI solutions may be held at 45° C. during deposition of each respective coat. After the third FAI coat has been deposited, the substrate and coatings may be annealed to form the perovskite material layer. In a particular embodiment, after the third FAI has been deposited, the substrate is immediately heated to 157° C. for 5 minutes to anneal the perovskite material layer.

Figure 31:
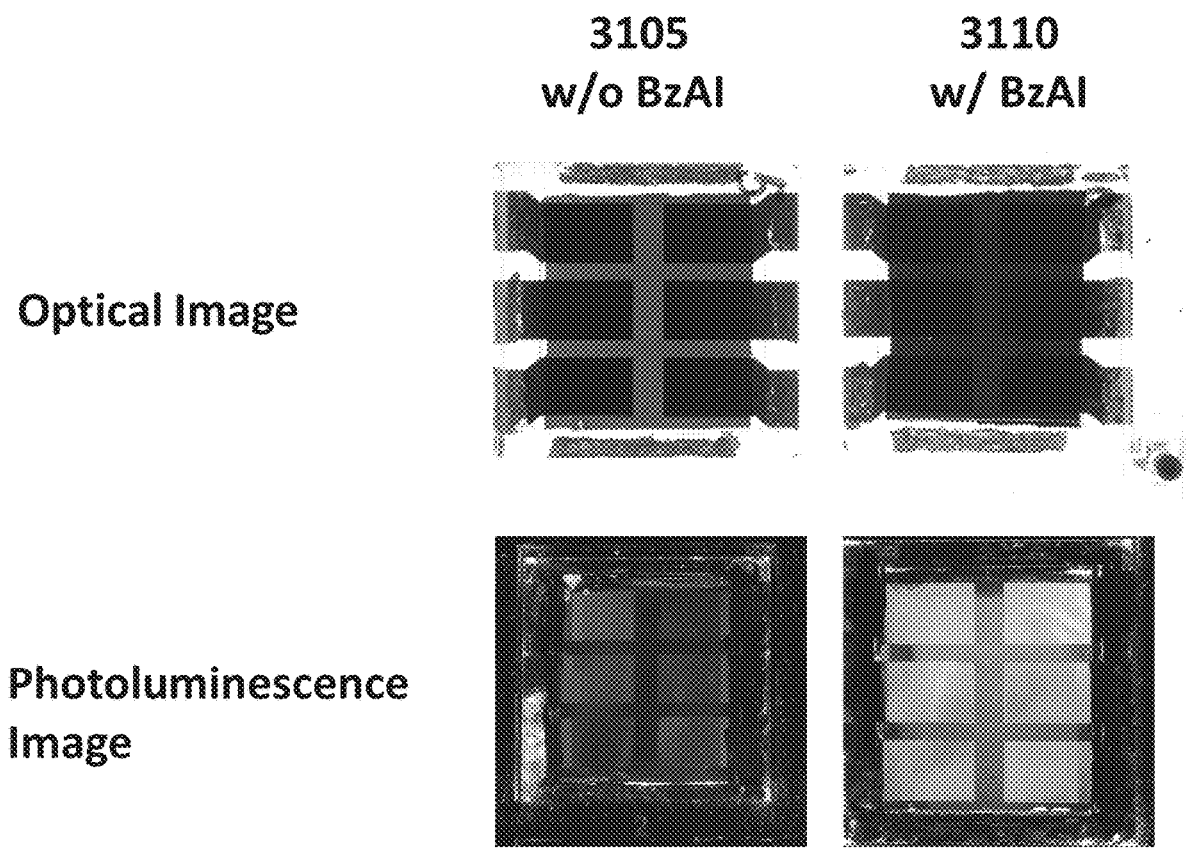
FIG. 31 shows optical and photoluminescence images of perovskite material photovoltaic devices according to some embodiments of the present disclosure.
Figure 32:
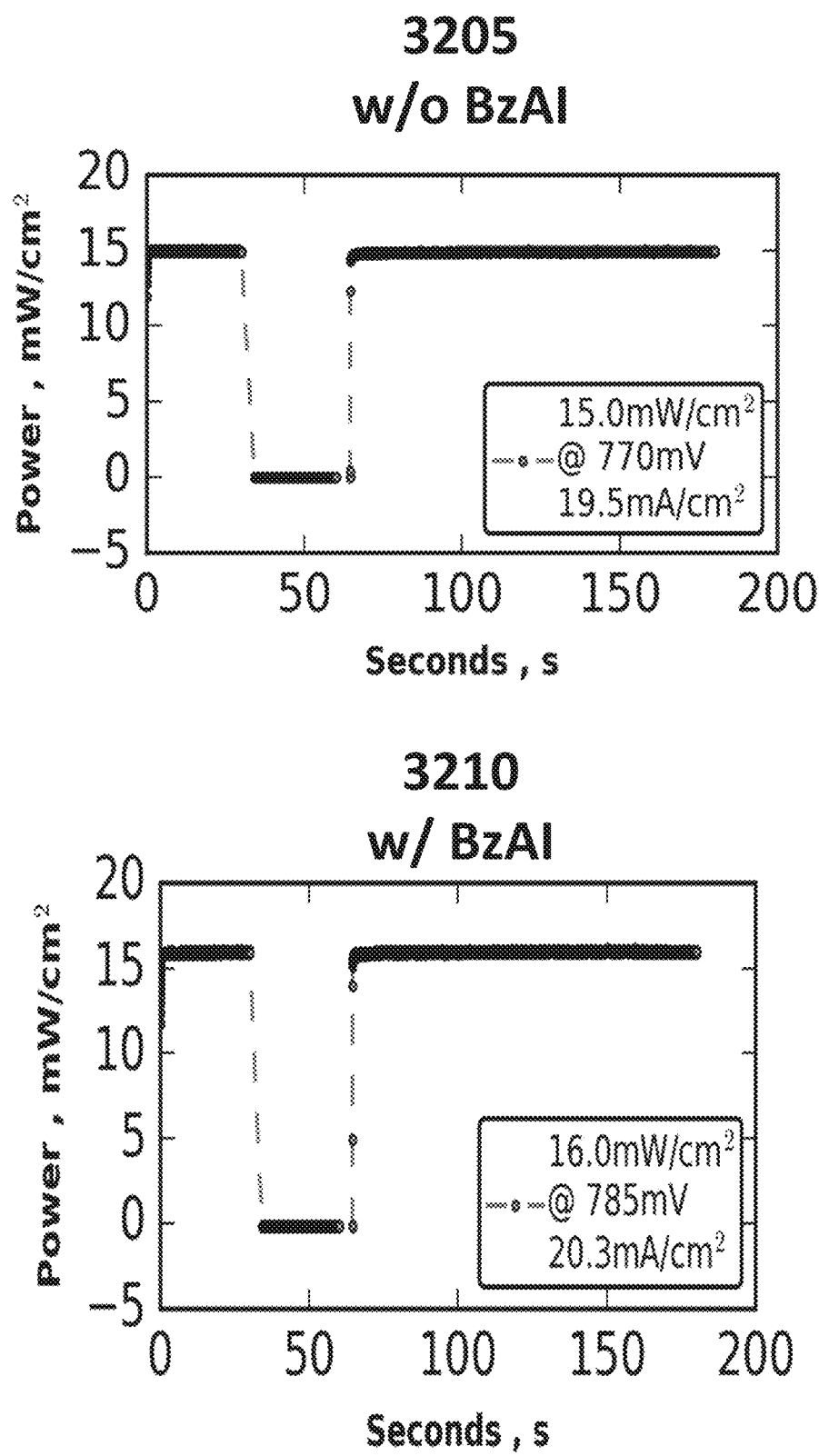
FIG. 32 illustrates power output curves of perovskite material photovoltaic devices, according to some embodiments of the present disclosure.
Figure 33:
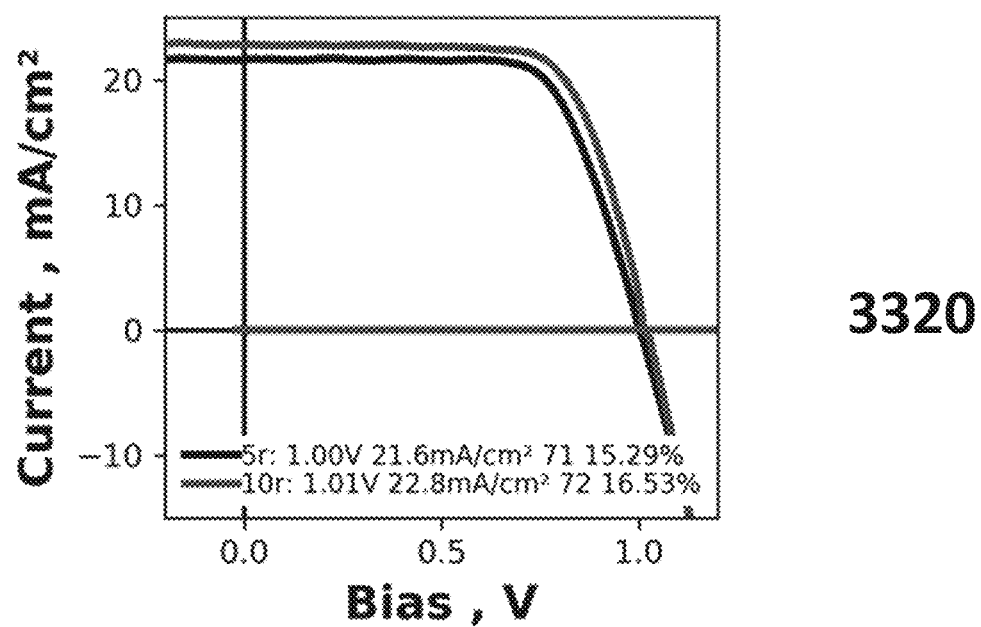
FIG. 33 illustrates current-voltage (I-V) scans of perovskite material photovoltaic devices, according to some embodiments of the present disclosure.
Figure 34:
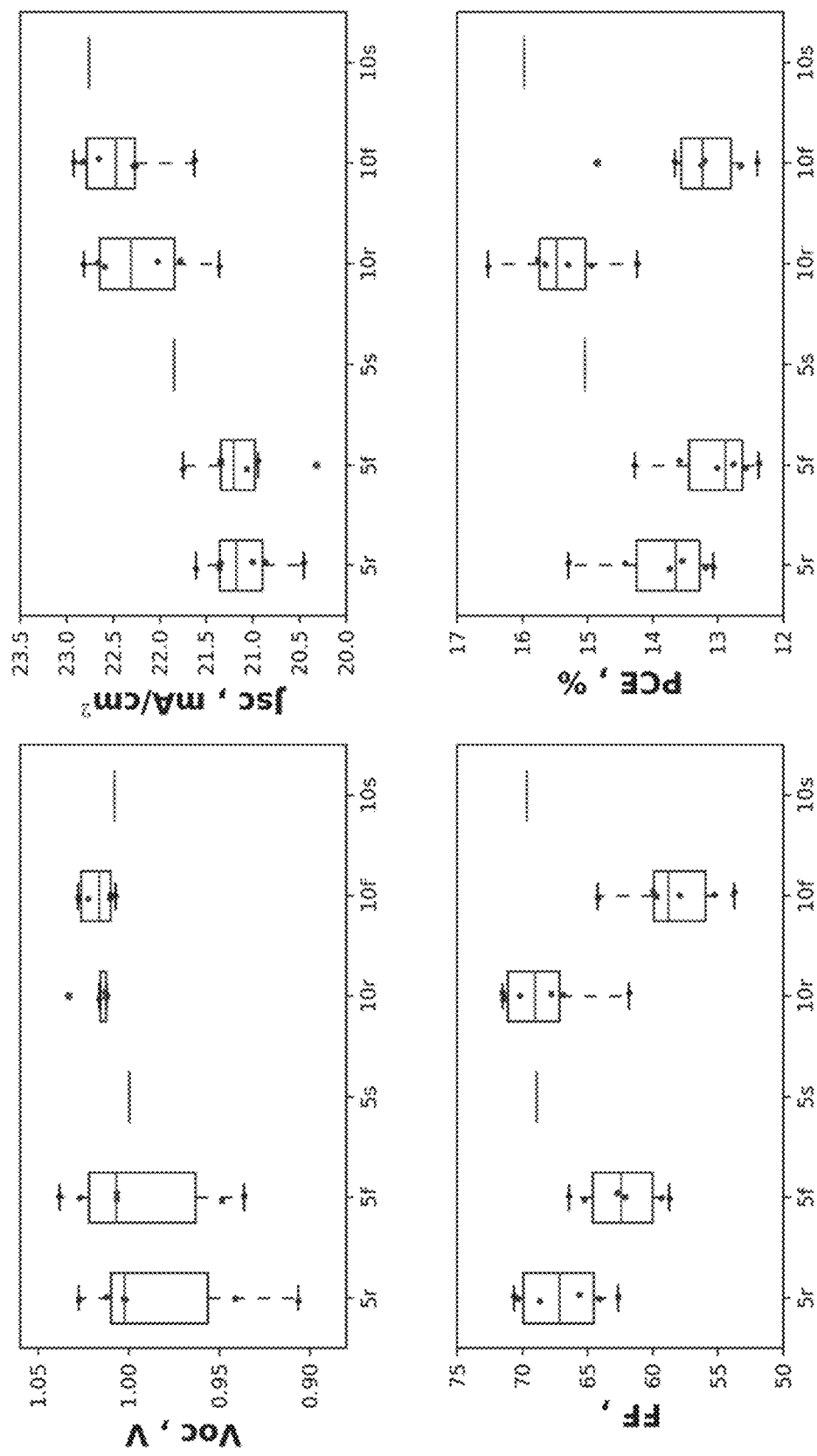
FIG. 34 illustrates box plots for open-circuit voltage (Voc), short-circuit current density (Jsc), Fill Factor (FF) and power conversion efficiency (PCE) for perovskite material photovoltaic devices, according to some embodiments of the present disclosure.
Figure 35:
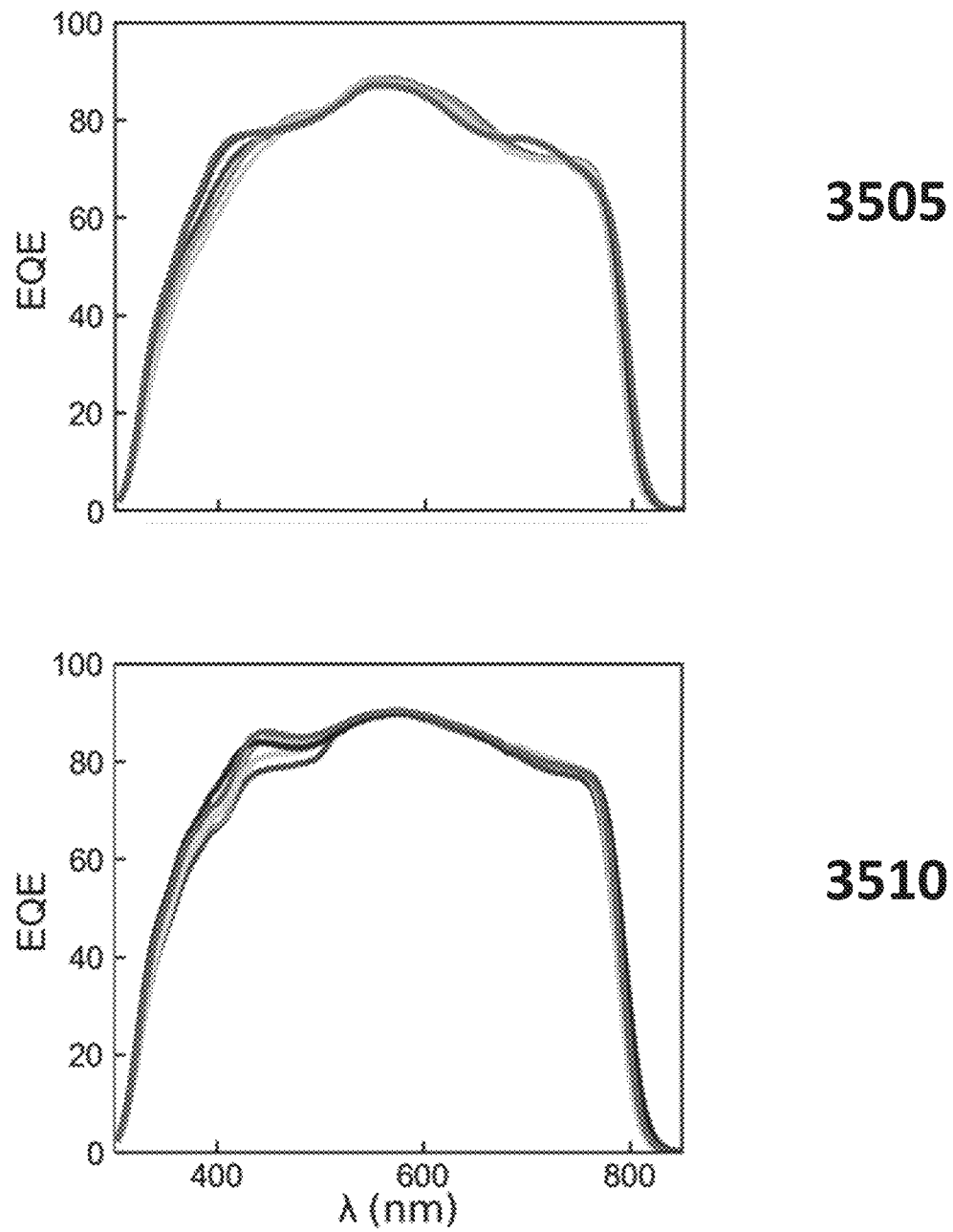
FIG. 35 illustrates external quantum efficiency (EQE) curves of perovskite material photovoltaic devices, according to some embodiments of the present disclosure.
Figure 36:
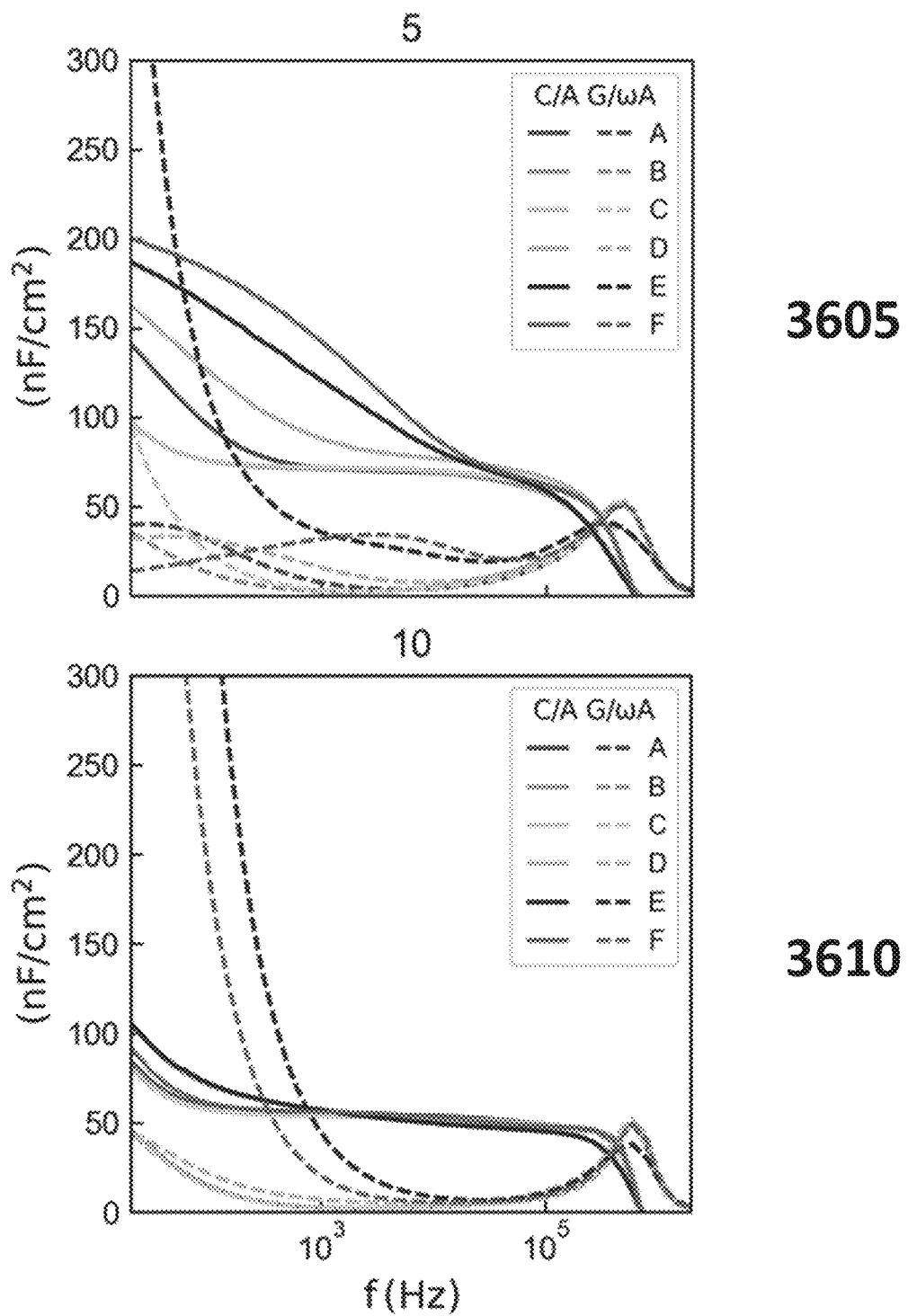
FIG. 36 shows admittance spectroscopy plots of perovskite material photovoltaic devices, according to some embodiments of the present disclosure.

The foregoing method may have several advantages. For example, depositing the BzAI solution onto the lead iodide film prior to deposition of the FAI solution may provide intermediate templating for growth of the 3D FAPbI3 perovskite material by formation of a 2D perovskite material. BzAI may react with lead iodide thin film to form an intermediate 2D perovskite material phase. Upon reacting with FAI after deposition of the FAI solution, the $BzA^+$ cations in the 2D phase may be fully or partially replaced with $FA^+$ cations to form a 3D $FAPbI_3$ framework. Additionally, the BzAI may also passivate crystal defects in the 3D $FAPbI_3$ perovskite material. Photoluminescence intensity of $FAPbI_3$ thin films formed by the process described above is brighter (higher) compared to that of $FAPbI_3$ thin films formed by a process not including BzAI. FIG. 31 illustrates both optical (absorbance) and photoluminescence images of a perovskite material photovoltaic device 3105 produced without addition of BzAI and perovskite material photovoltaic device 3110 produced with BzAI as described herein. FIG. 31 shows that the optical image of perovskite material photovoltaic device 3110 is darker, indicating a higher light absorbance, and the photoluminescence image of perovskite material photovoltaic device 3110 is brighter than perovskite material photovoltaic device 3105. Additionally, power output has been observed to be greater from perovskite material photovoltaic devices incorporating BzAI. FIG. 32 illustrates power output curve 3205 corresponding to a photovoltaic device without BzAI, such as photovoltaic device 3105, and power output curve 3210 corresponding to a photovoltaic device with BzAI as described herein, such as photovoltaic device 3110. The power output measurements depicted in FIG. 32 were measured at maximum power point under 100 $mW/cm^2$ AM1.5G illumination for 180 seconds with an intervening 30 second dark measurement to demonstrate steady-state performance. As can be seen from FIG. 32, a photovoltaic device incorporating BzAI during production produces more power per unit area (16.0 $mW/cm^2$) more voltage (785 mV), and more current per unit area (20.3 $mA/cm^2$) than a photovoltaic device produced without BzAI (15.0 $mW/cm^2$, 770 mV, and 19.5 $mA/cm^2$). FIG. 33 illustrates a current-voltage (I-V) scan 3320 of a perovskite material photovoltaic device produced without BzAI, labeled as the sample "5r" line, and a perovskite material photovoltaic device produced with BzAI, labeled as the sample "10r" line. As can be seen from FIG. 33, the perovskite material photovoltaic device produced with BzAI produces a greater current across a range of bias voltages than does the perovskite material photovoltaic device produced without BzAI. Additionally, FIG. 34 shows box plots for open-circuit voltage (Voc), short-circuit current density (Jsc), Fill Factor (FF) and power conversion efficiency (PCE) for six perovskite material photovoltaic devices produced without BzAI (sample 5, r=reverse scan, f=forward scan, and s=steady-state measurement) and six perovskite material photovoltaic devices produced with BzAI (sample 10). FIG. 35 illustrates external quantum efficiency (EQE) of six perovskite material photovoltaic devices produced without BzAI (plot 3505) and six perovskite material photovoltaic devices produced with BzAI (plot 3510). Each EQE curve of FIG. 35 has been integrated to estimate Jsc in $mA/cm^2$, illustrating that the perovskite material devices produced with BzAI display a higher Jsc (area under the EQE curve) than the perovskite material devices produced without BzAI. Finally, FIG. 36 shows an admittance spectroscopy plot 3605 for perovskite material photovoltaic devices produced without BzAI and an admittance spectroscopy plot 3610 for perovskite material photovoltaic devices produced with BzAI. Admittance spectroscopy plot 3610 shows suppressed ion migration for sample devices including benzylammonium when compared to admittance spectroscopy plot 3605 for sample devices not including benzylammonium. Excessive ion migration is known to have deleterious effects on perovskite material device performance and durability, indicating that the inclusion of benzylammonium in perovskite material photovoltaic devices may increase device performance and durability.

Diammonium Butane Cation Enhanced Perovskite

Incorporation of 1,4-diammonium butane, or other polyammonium organic compounds as described below, into the crystal structure of a perovskite material may improve the properties of that material. In one embodiment, addition of 1,4-diammonium butane into a $FAPbI_3$ perovskite as described below may provide the perovskite material with advantageous properties. In some embodiments, 1,4-diammonium butane may be incorporated into a perovskite material utilizing a 1,4-diammonium butane salt in the place of the bulky organic cation salt in the process described above, and the addition of the 1,4-diammonium butane salt (or other organic polyammonium salt described herein) may occur at any stage of the perovskite production method for which addition of the bulky organic cation salt is described above. The inclusion of organic cations, such as 1,4-diammonium butane, into the crystal structure of a perovskite material may result in the formula of the perovskite material deviating from the "ideal" stoichiometry of perovskite materials disclosed herein. For example, inclusion of such organic cations may cause the perovskite material to have a formula that is either substoichiometric or superstoichiometric with respect to the $FAPbI_3$ formula. In this case, the general formula for the perovskite material may be expressed as $C_xM_yX_z$, where x, y and z are real numbers.

In one embodiment, a 1,4-diammonium butane salt solution may be added to the lead halide precursor ink solution prior to deposition. In certain embodiments, a 1,4-diammonium butane salt may be added to the lead halide precursor ink solution at a concentration of 0.001 mol % to 50 mol %. In some embodiments, the 1,4-diammonium butane salt may be added to the lead halide precursor ink solution at a concentration of 0.1 mol % to 20 mol %. In particular embodiments, the 1,4-diammonium butane salt may be added to the lead halide precursor ink solution at a concentration of 1 mol % to 10 mol %.

In another embodiment, 1,4-diammonium butane salt may be added to the formamidinium salt solution prior to contacting the formamidinium salt solution with the lead halide precursor thin film as described above. In certain embodiments, a 1,4-diammonium butane salt may be added to the formamidinium iodide salt solution at a concentration of 0.001 mol % to 50 mol %. In some embodiments, the 1,4-diammonium butane salt may be added to the formamidinium iodide salt solution at a concentration of 0.1 mol % to 20 mol %. In particular embodiments, the 1,4-diammonium butane salt may be added to the formamidinium iodide salt solution at a concentration of 1 mol % to 10 mol %.

In other embodiments, a 1,4-diammonium butane salt precursor solution may be deposited onto a lead halide thin film formed after deposition of a lead halide precursor ink or onto a perovskite precursor thin film after deposition of the formamidinium salt solution. In certain embodiments, the 1,4-diammonium butane salt precursor solution may have a concentration of 0.001 mol % to 50 mol %. In some embodiments, the 1,4-diammonium butane salt precursor solution may have a concentration of 0.1 mol % to 20 mol %. In particular embodiments, the 1,4-diammonium butane salt precursor solution may have a concentration of 1 mol % to 10 mol %.

An example method for depositing a perovskite material including 1,4-diammonium butane includes depositing a lead salt precursor onto a substrate to form a lead salt thin film and depositing an organic cation salt precursor comprising a first organic cation salt onto the lead salt thin film to form a perovskite precursor thin film. The lead salt precursor or the organic cation salt precursor may include a 1,4-diammonium butane salt or a 1,4-diammonium butane salt precursor may be deposited onto the lead salt thin film or the perovskite precursor thin film. Finally the substrate and perovskite precursor thin film may be annealed to form a perovskite material that includes 1,4-diammonium butane. The lead salt precursor and organic cation salt precursor may include any solutions described herein used to produce a perovskite thin film.

1,4-diammonium butane has nearly the same length between its ammonium groups as occurs between formamidinium cations in the formamidinium lead iodide perovskite material crystal lattice. Accordingly, the 1,4-diammonium butane may substitute for two formamidinium ions during the formation of an FAPbI$_3$ material. In alternate embodiments, other alkyl polyammonium salts may be added to the lead halide precursor ink during formation of the perovskite material. For example, 1,8 diammonium octane, bis(4-aminobutyl)amine, and tris(4-aminobutyl)amine may be added. Additionally, the polyammonium polycations, including 1,4-diammonium butane, may provide the same benefits as the bulky organic cations described above by similar mechanisms to those described above with respect to the bulky organic cations.

Figure 13:
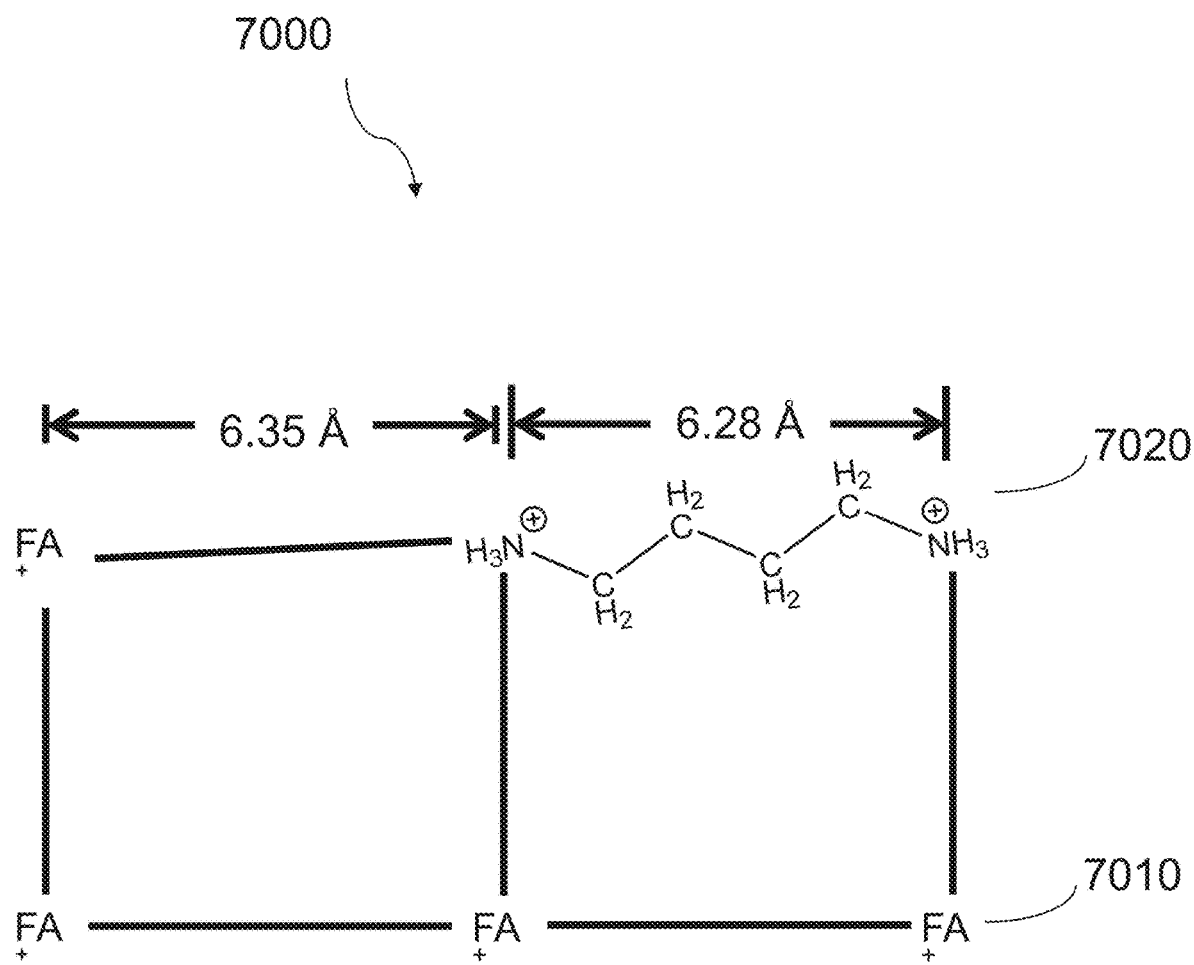
FIG. 13 is a stylized diagram showing an illustration of 1,4-diammonium butane incorporated into the crystal lattice of a formamidinium lead iodide perovskite material, according to some embodiments of the present disclosure.

FIG. 13 is a stylized illustration of an effect of addition of a 1,4-diammonium butane salt during the process of producing a perovskite material may have on the resulting perovskite 7000. As illustrated by FIG. 13, the 1,4-diammonium butane cation 7020 may substitute for two formamidinium cations 7010 in the perovskite material crystal lattice. In FAPbI$_3$ perovskite, the spacing between formamidinium cations is approximately 6.35 Å. The length of the length of the 1,4-diammonium butane cation is approximately 6.28 Å, a difference of only 0.07 Å. Accordingly, the 1,4-diammonium butane cation may substitute into the perovskite crystal lattice without significantly changing the properties or structure of the perovskite crystal lattice. In some embodiments, the addition of the 1,4-diammonium butane cation to a perovskite material may enhance the properties and stability of the perovskite material. The 1,4-diammonium butane cation may act as a rigid structure within the perovskite material, increasing its structural and chemical durability. For example, in some embodiments perovskite material with added 1,4-diammonium butane cation may demonstrate superior dry heat stability compared to a perovskite material without 1,4-diammonium butane cation. Additionally, a perovskite material with added 1,4-diammonium butane cation may demonstrate a blue shift in the emission spectra of the perovskite material. In some embodiments the 1,4-diammonium butane cation may be added at a concentration between 0 and 20 mol % to the formamidinium salt solution. In other embodiments the 1,4-diammonium butane cation may be added at a concentration between 1 and 5 mol % to the formamidinium salt solution. In a particular embodiment the 1,4-diammonium butane cation added at a concentration 5 mol % to the formamidinium salt solution.

Figure 14:
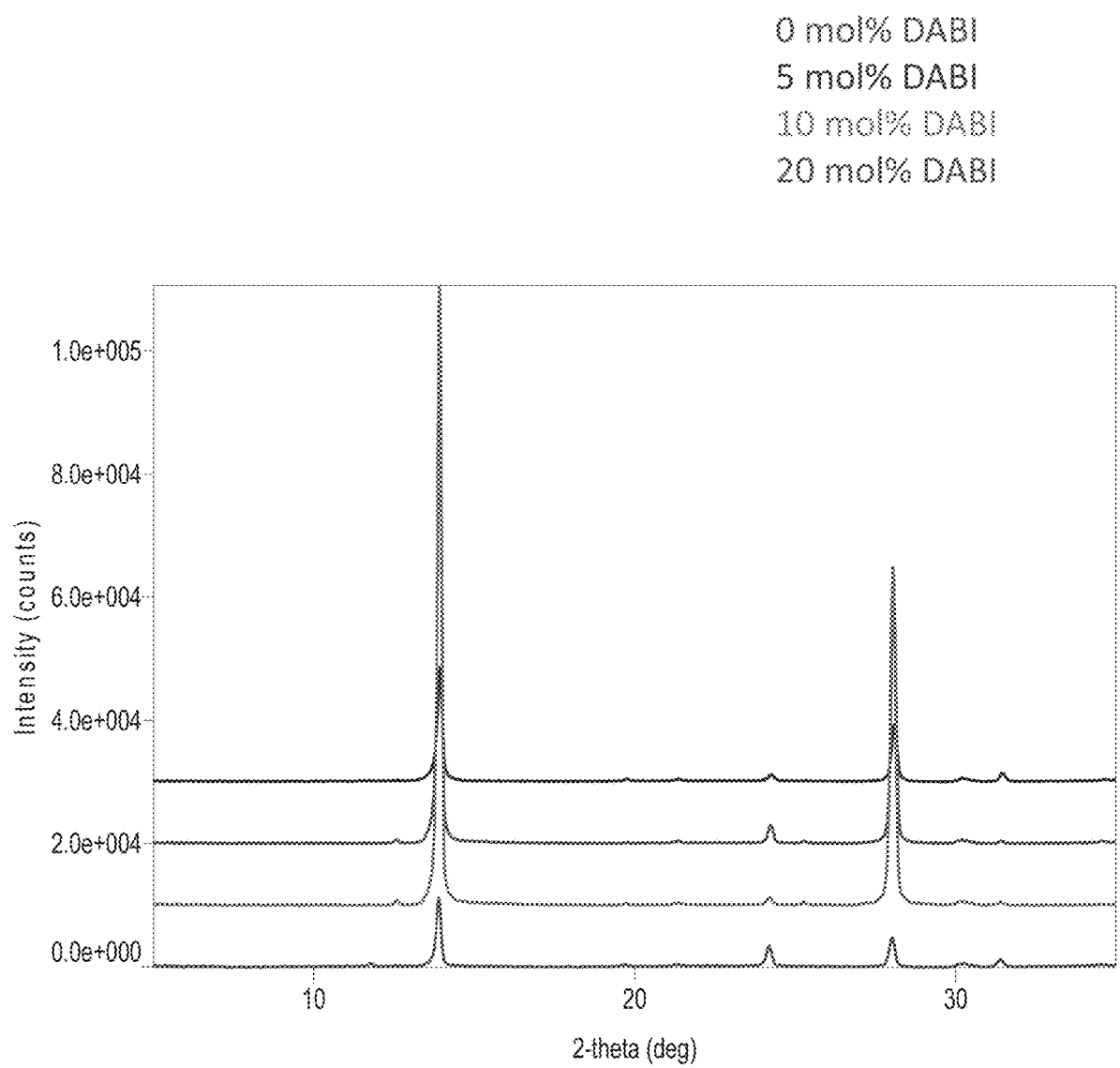
FIG. 14 is an illustration of x-ray diffraction peaks (XRD) for perovskite having various concentrations of 1,4-diammonium butane, according to some embodiments of the present disclosure.

Experimental evidence has shown that for additions of up to 20% 1,4-diammonium butane to a perovskite material, the lattice parameters do not appreciably shift. FIG. 14 provides x-ray diffraction peaks (XRD) for perovskite having 0 mol %, 5 mol %, 10 mol %, and 20 mol % 1,4-diammonium butane iodide ("DABI"). For each concentration the major peaks occur at the same points, indicating that the lattice parameters for a perovskite material do not change appreciably with addition of a concentration between 0 mol % and 20 mol % 1,4-diammonium butane. The addition of 1,4-diammonium butane may create small intensity diffractions at less than 13° 2θ with Cu-Kα radiation, which are indicative of a small amount of 2D or layered perovskite phase.

Figure 15:
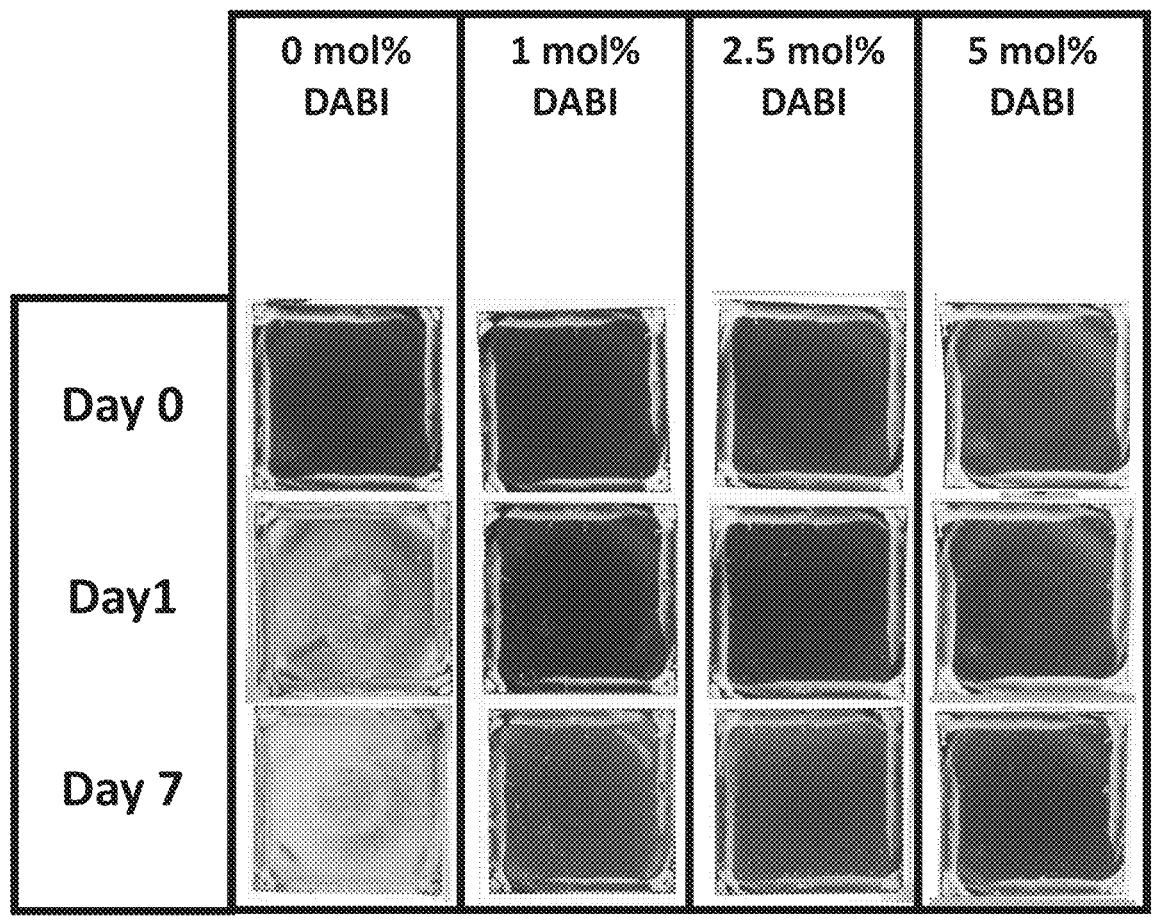
FIG. 15 provides images of perovskite material samples having various concentrations of 1,4-diammonium butane over time, according to some embodiments of the present disclosure.

FIG. 15 provides images of perovskite samples having 0 mol %, 1 mol %, 2.5 mol % and 5 mol % exposed to a temperature of 85° C. at 0% relative humidity for seven days. The perovskite material with 0 mol % DABI shows significant lightening in color after one day and even more significant yellowing after seven days. This indicates that the perovskite material with 0 mol % DABI has degraded significantly after one day exposed to the testing conditions. The perovskite material samples with 1 mol %, 2.5 mol % and 5 mol % all remain dark after seven days, indicating that addition of as little as 1 mol % DABI significantly increases so called "dry heat" stability of the perovskite material.

Additionally, addition of 1,4-diammonium butane to a perovskite material may result in a slight blue shift of photoluminescence seen from a perovskite material when compared to a perovskite material without 1,4-diammonium butane. This blue shift results from the passivation of trap states within the perovskite material resulting from the addition of 1,4-diammonium butane. This blue shift indicates that the addition of 1,4-diammonium butane to a perovskite material decreases defect density in the perovskite material crystal lattice without changing the crystal structure of the perovskite material. For example, it has been observed that the resulting blue shift seen in an FAPbI3 perovskite material with 20 mol % of added 1,4-diammonium butane compared to a FAPbI3 perovskite material without 1,4-diammonium butane is a change of 0.014 eV, from 1.538 eV with no 1,4-diammonium butane to 1.552 eV with 20 mol % 1,4-diammonium butane.

Figure 16:
FIG. 16 provides illustrations of poly-ammonium alkyl cations, according to some embodiments of the present disclosure.
Figure 16:
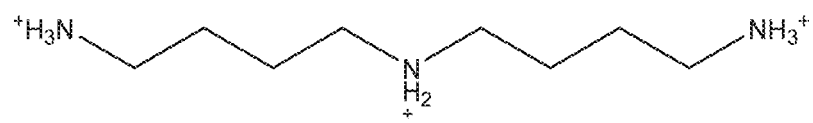
Figure 16:
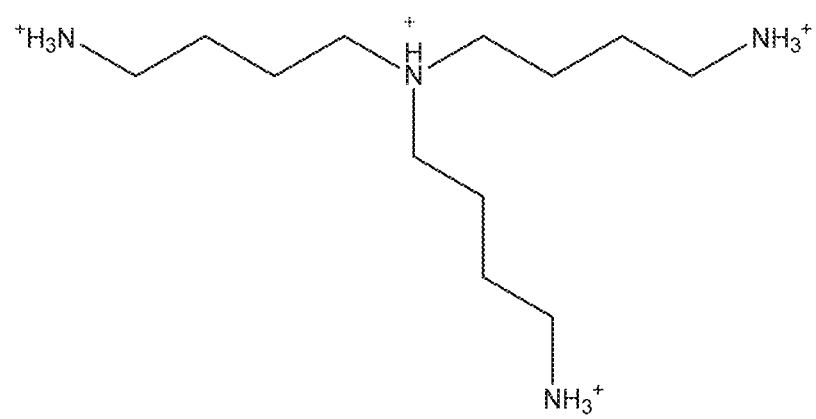
Figure 16A:
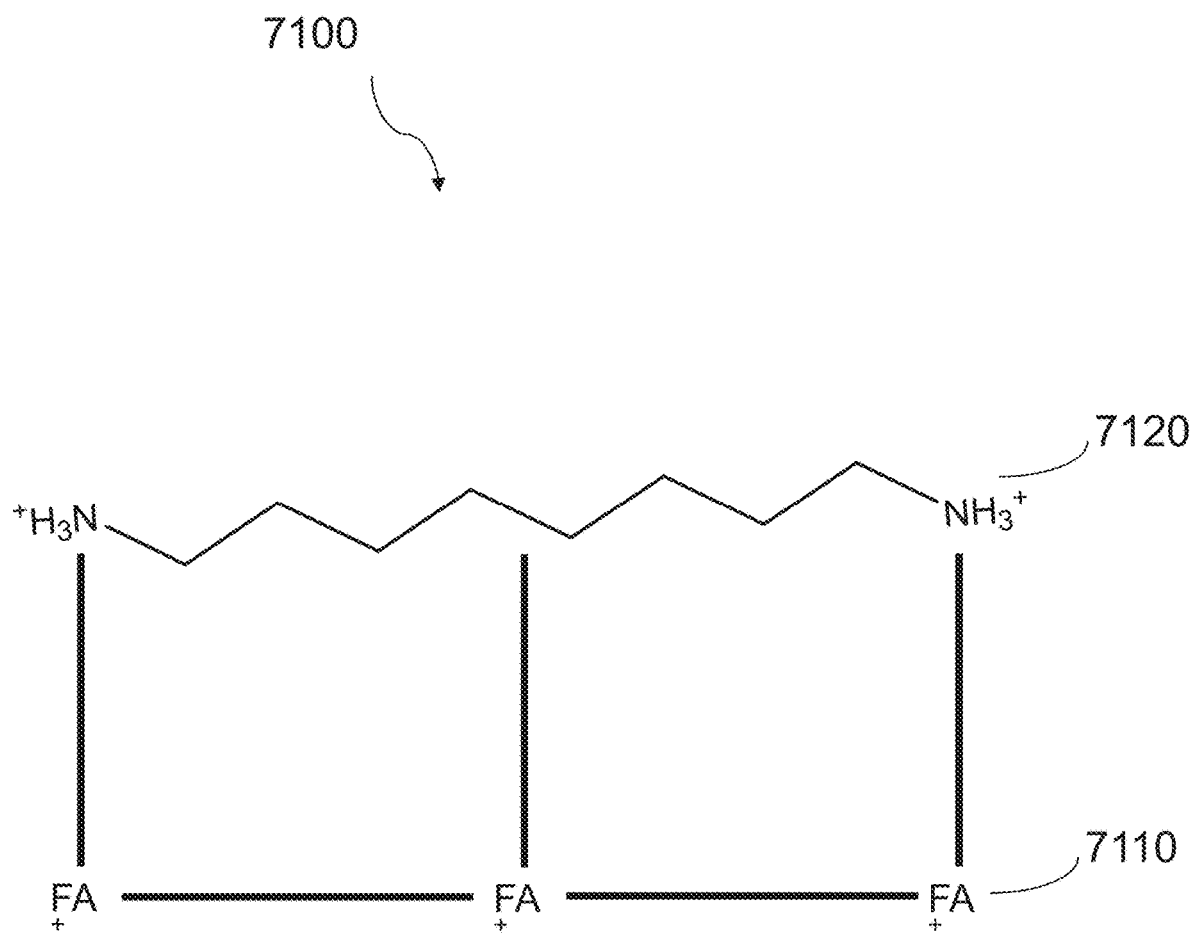
FIG. 16A is a stylized diagram showing an illustration of 1,8 diammonium octane incorporated into the crystal lattice of a formamidinium lead iodide perovskite material, according to some embodiments of the present disclosure.
Figure 16B:
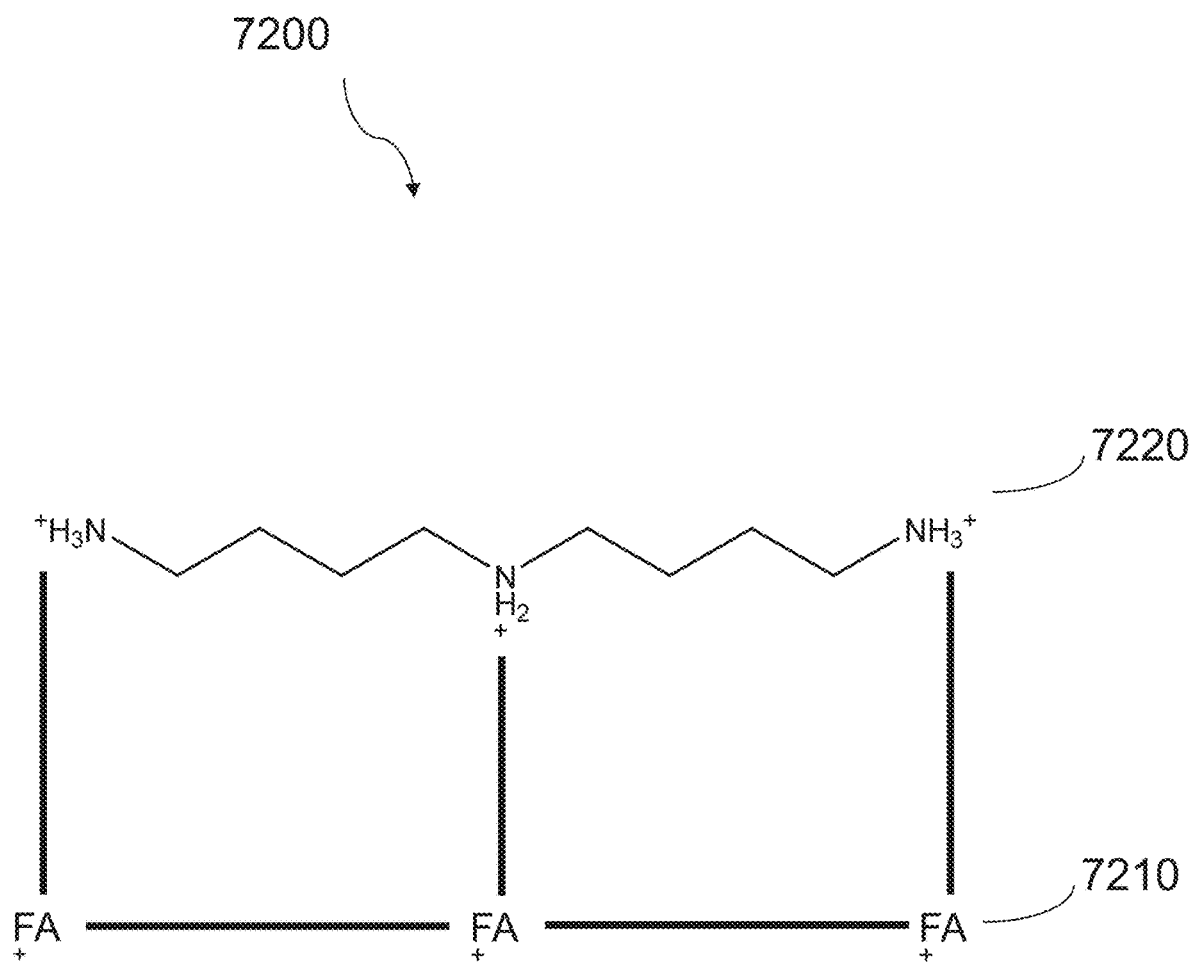
FIG. 16B is a stylized diagram showing an illustration of bis(4-aminobutyl)-ammonium incorporated into the crystal lattice of a formamidinium lead iodide perovskite material, according to some embodiments of the present disclosure.
Figure 16C:
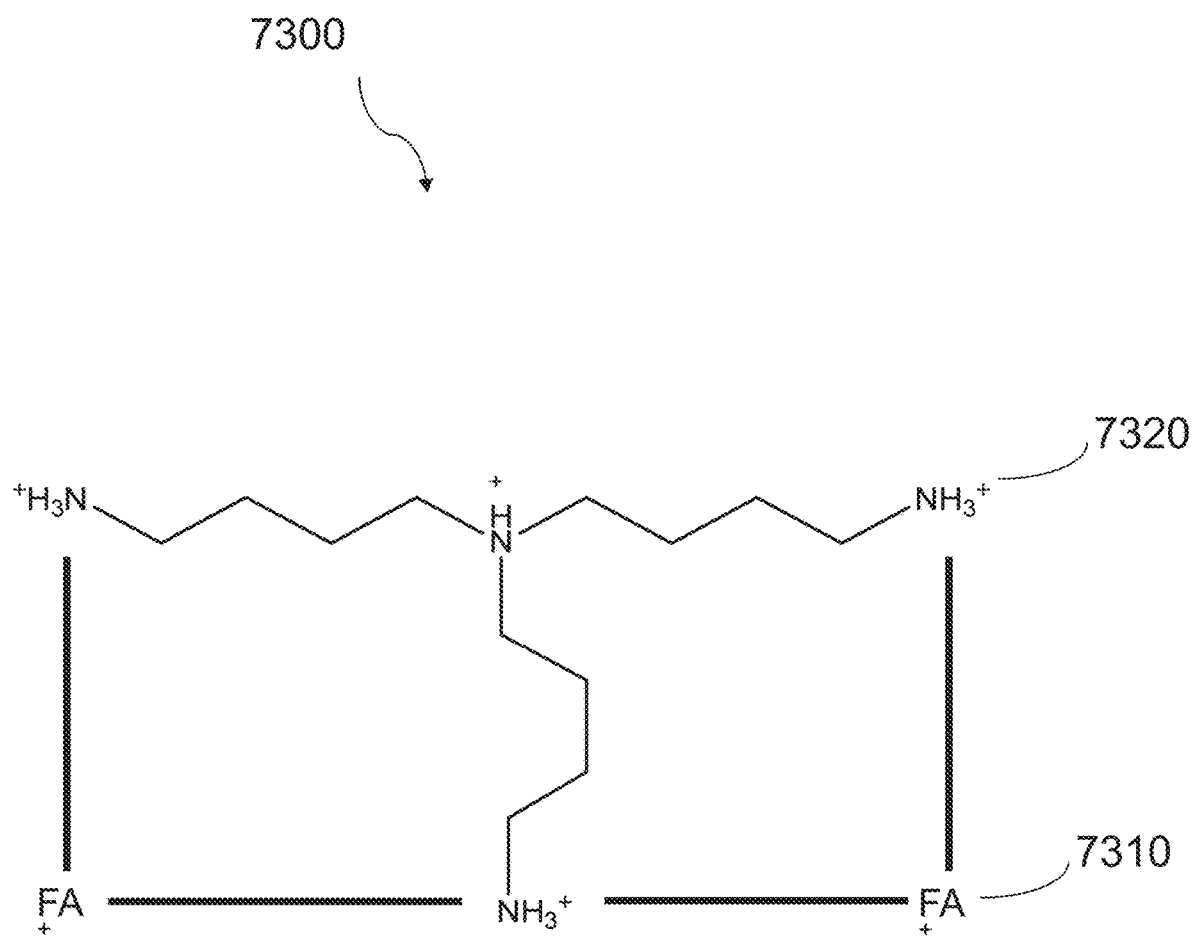
FIG. 16C is a stylized diagram showing an illustration of tris(4-aminobutyl)-ammonium incorporated into the crystal lattice of a formamidinium lead iodide perovskite material, according to some embodiments of the present disclosure.
Figure 17:
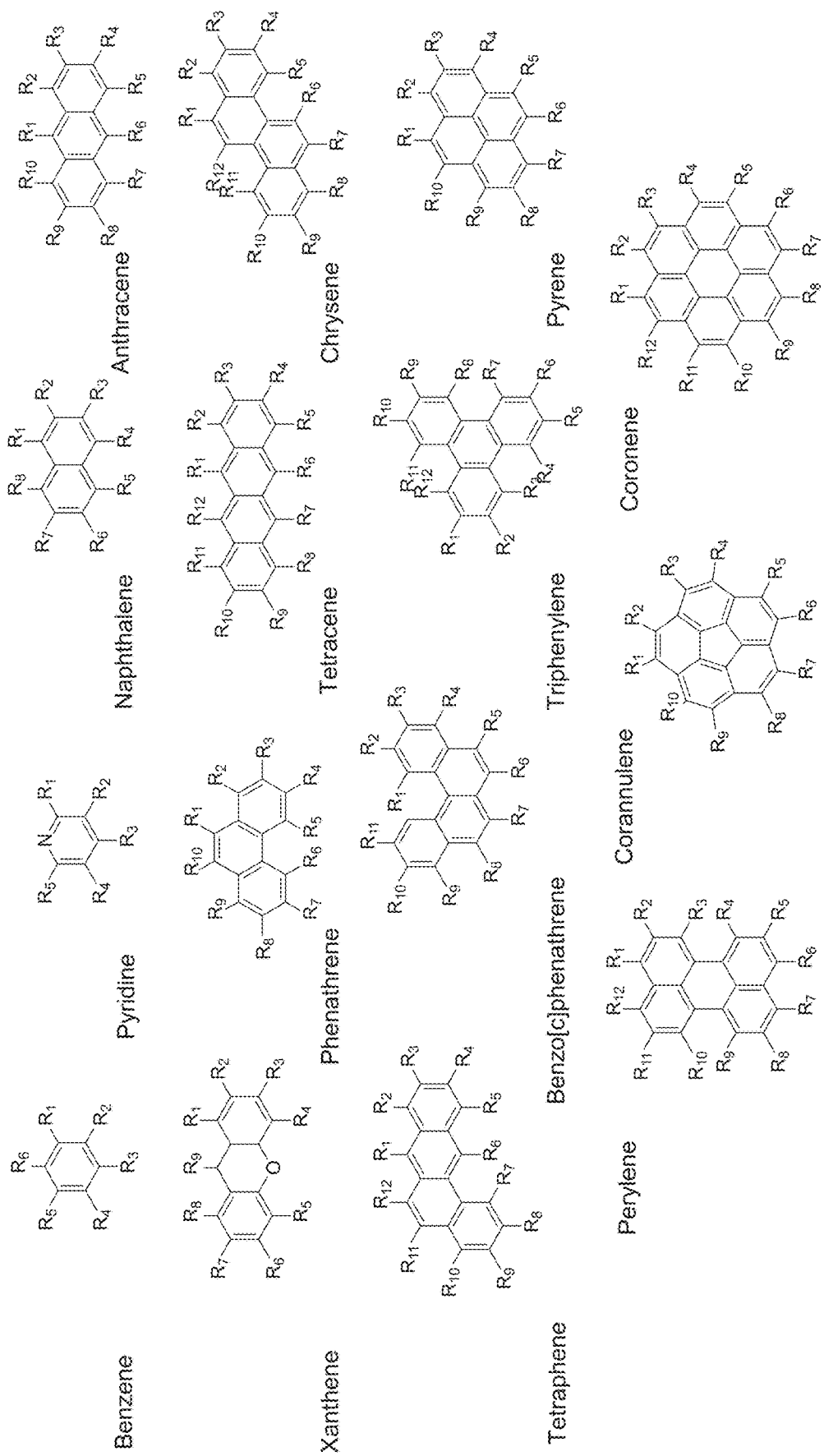
FIGS. 17-28 provide illustrations of the structures of certain organic molecules, according to some embodiments of the present disclosure.
Figure 18:
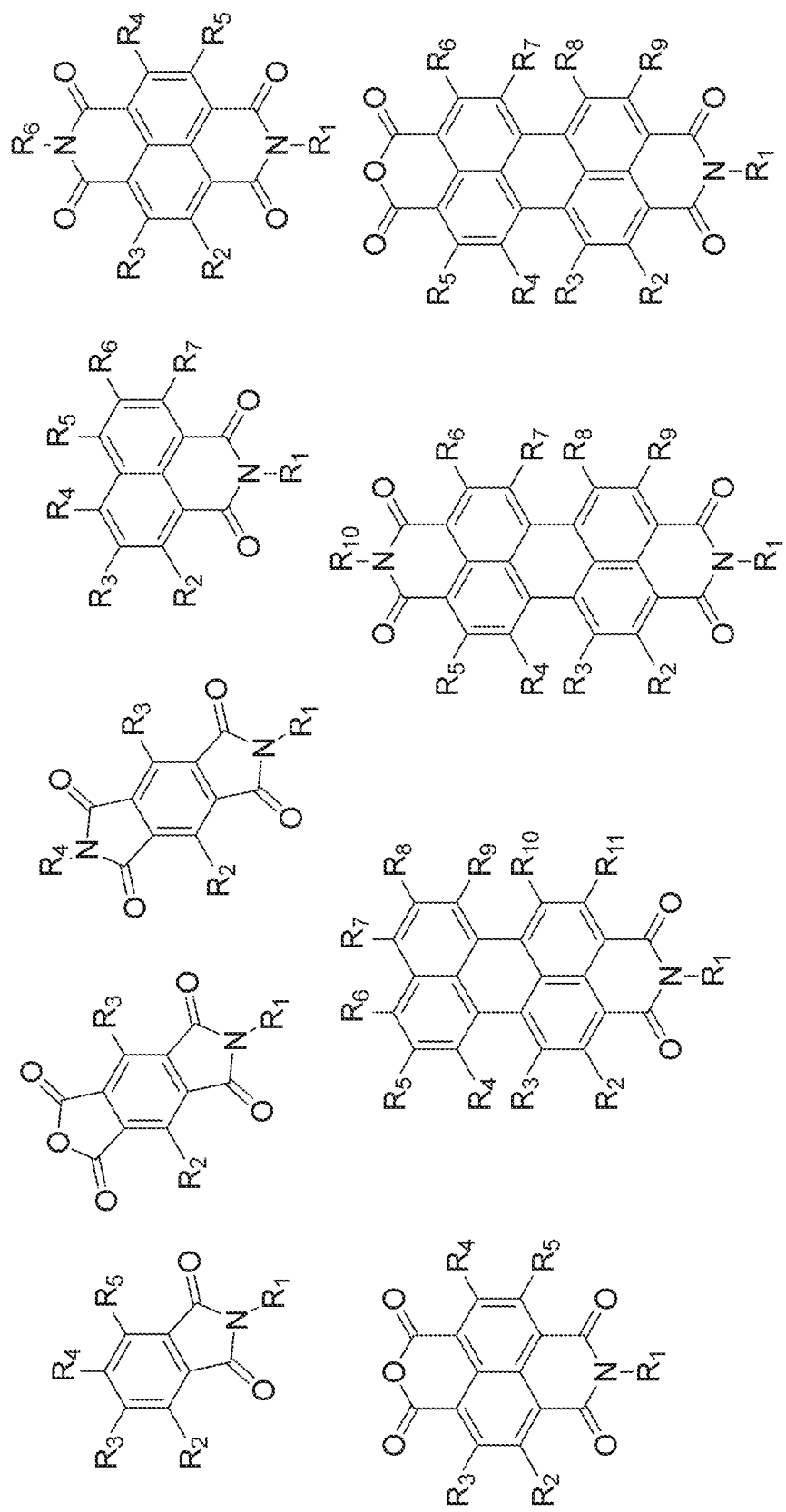
Figure 19:
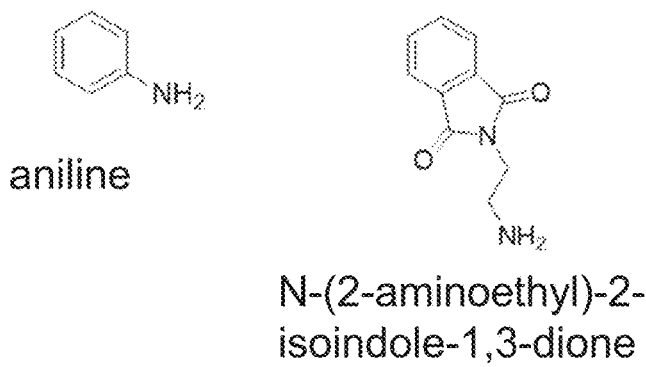
Figure 19:
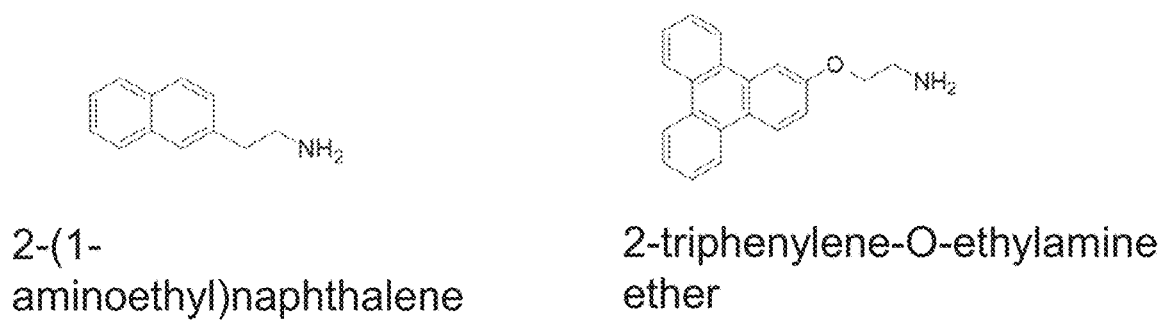
Figure 19:
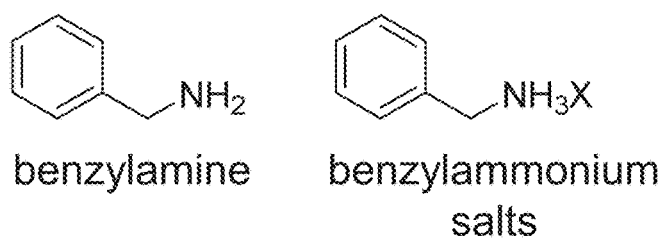
Figure 19:
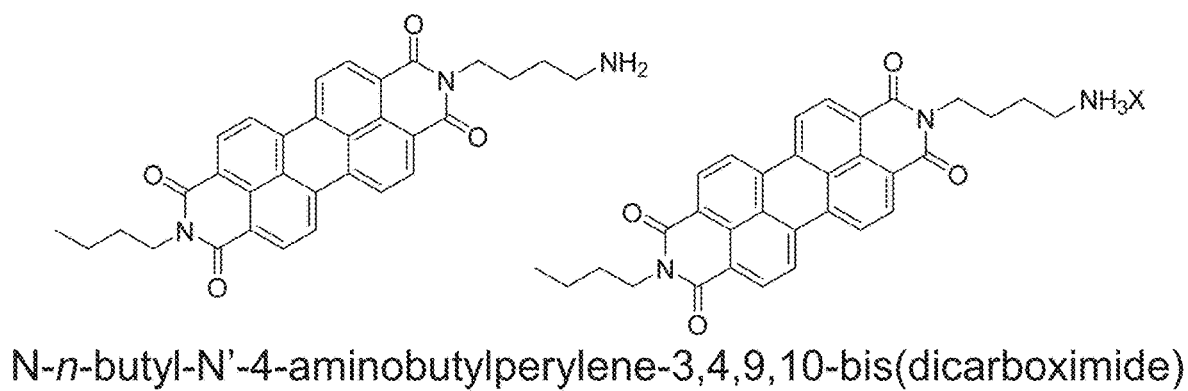
Figure 20:
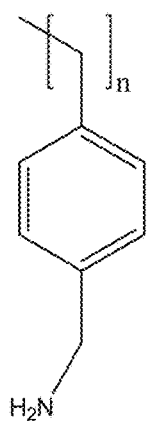
Figure 20:
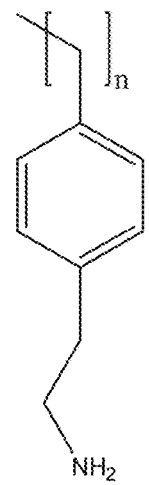
Figure 20:
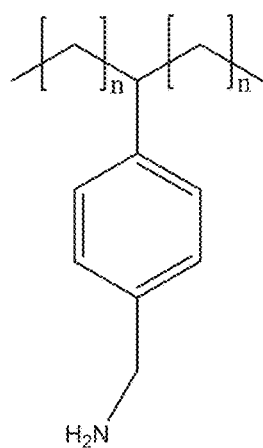
Figure 20:
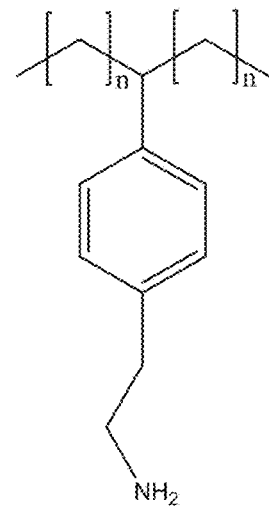
Figure 21:
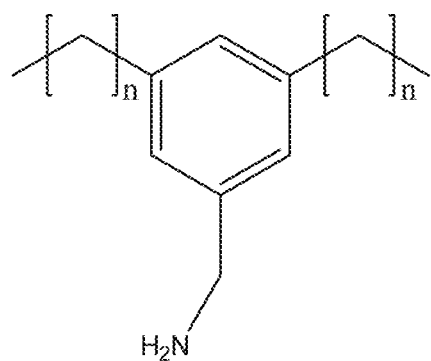
Figure 21:
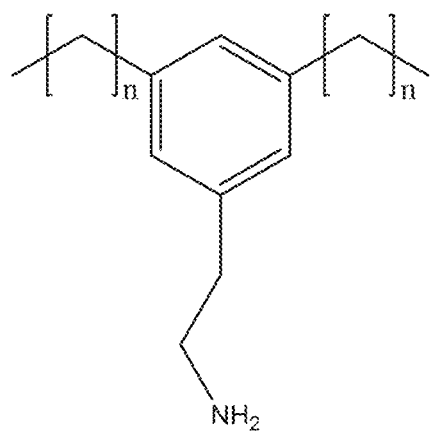
Figure 22:
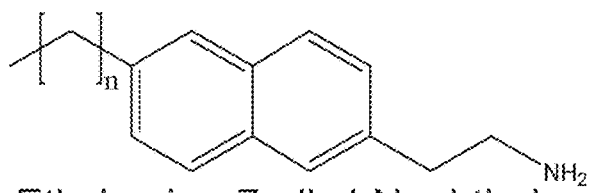
Figure 22:
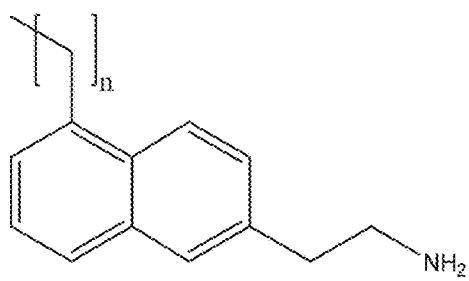
Figure 22:
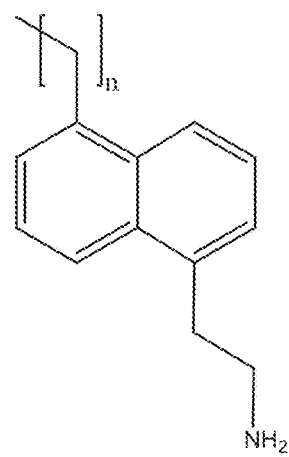
Figure 22:
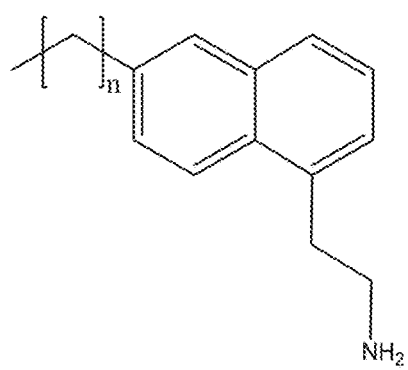
Figure 23:
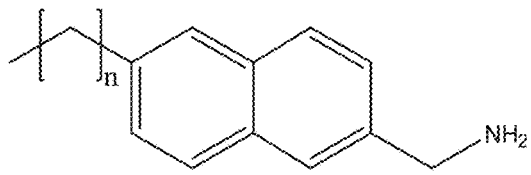
Figure 23:
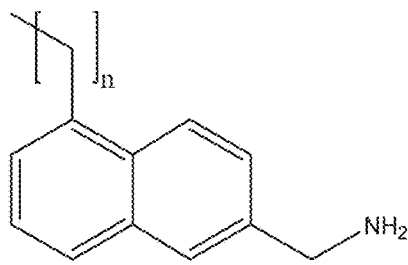
Figure 23:
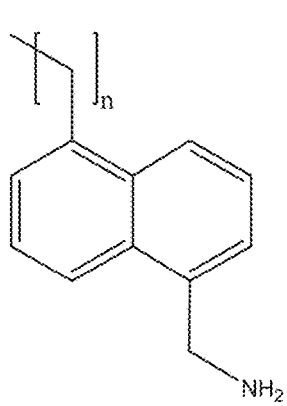
Figure 23:
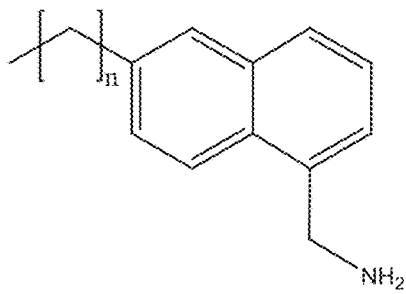
Figure 24:
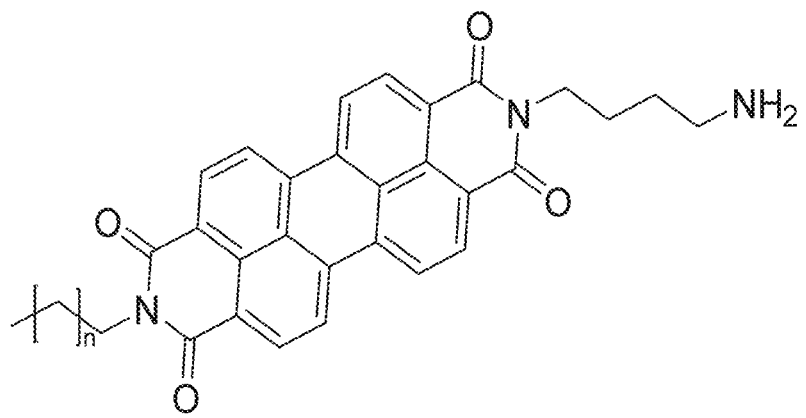
Figure 25:
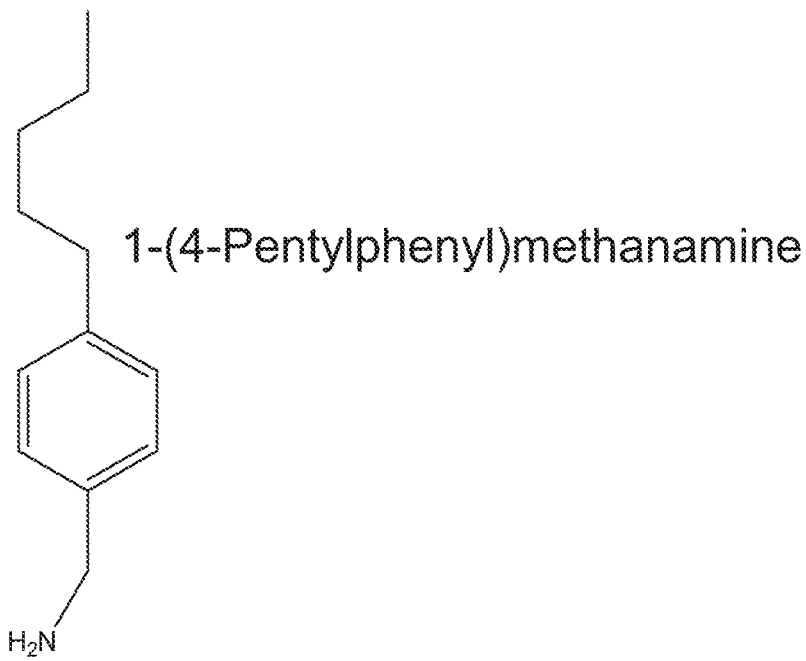
Figure 25:
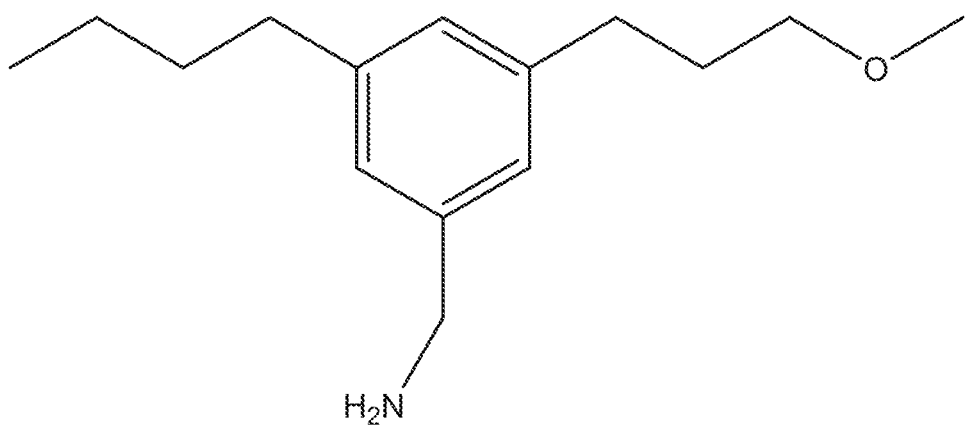
Figure 26:
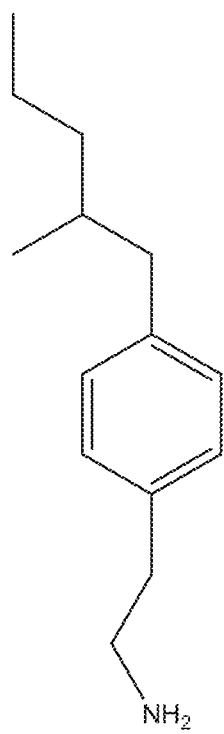
Figure 26:
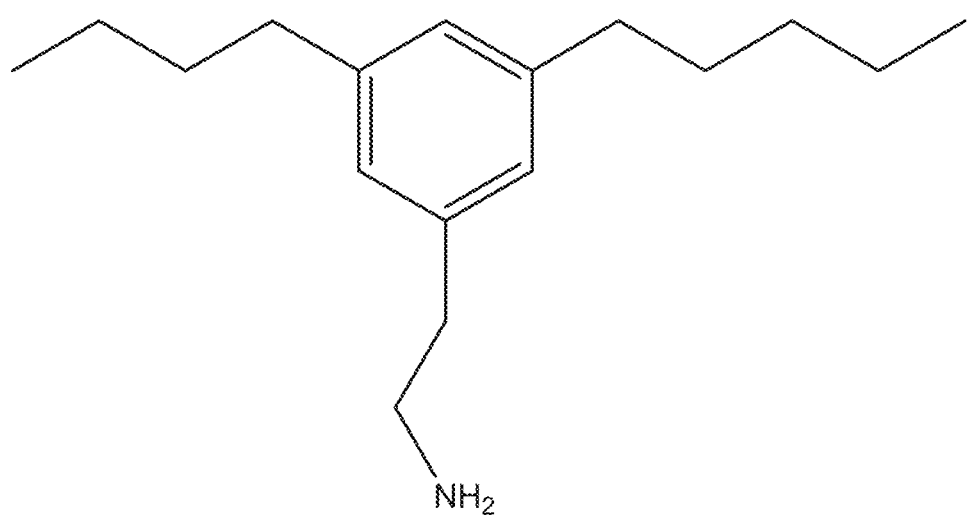
Figure 27:
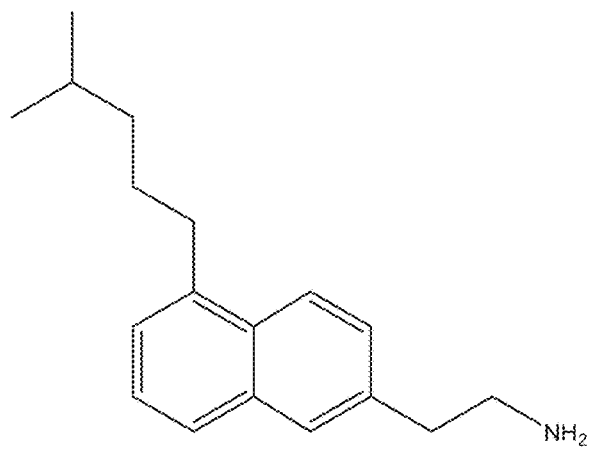
Figure 27:
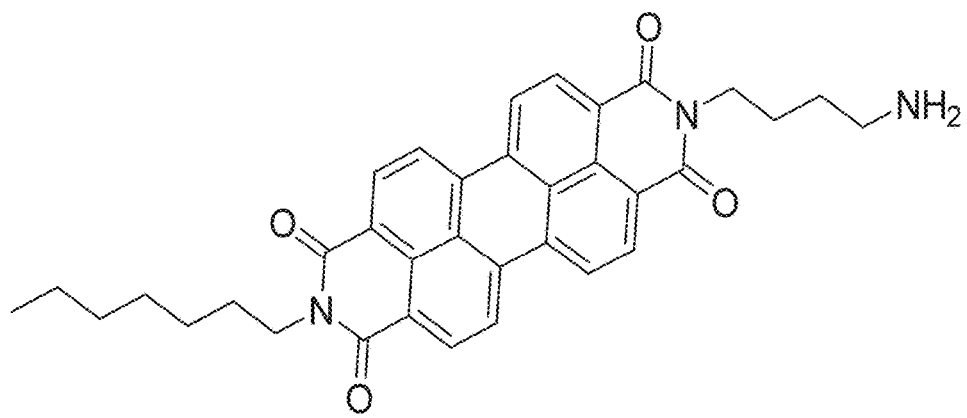
Figure 28:
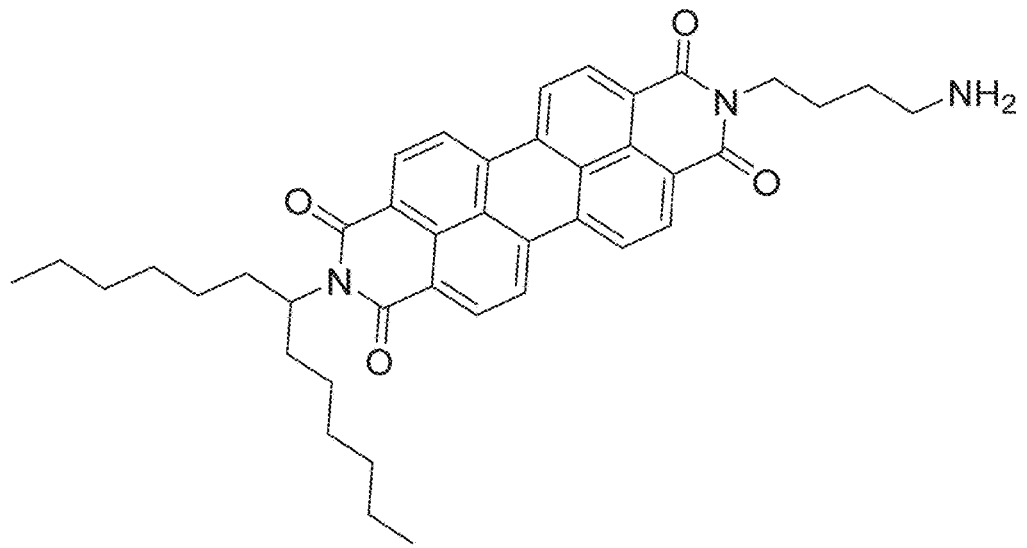
Figure 28:
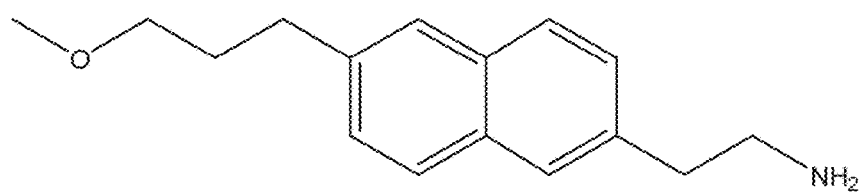

In other embodiments, other ammonium complexes may be added during formation of the perovskite material. For example, FIG. 16 illustrates three ammonium compounds, 1,8-diammonium octane, bis(4-aminobutyl)-ammonium and tris(4-aminobutyl)-ammonium, which may be added to a perovskite material in the same method as described above with respect to the 1,4-diammonium butane cation. 1,8-diammonium octane may occupy the space of two formamidinium cations ("A-sites") of a FAPbI$_3$ perovskite material crystal lattice when introduced during the formation of the perovskite material as described above. Bis(4-aminobutyl)-ammonium may occupy the space of three A-sites of a FAPbI$_3$ perovskite material crystal lattice when introduced during the formation of the perovskite material as described above. Tris(4-aminobutyl)-ammonium may occupy the space of four A-sites of a FAPbI$_3$ perovskite material crystal lattice when introduced during the formation of the perovskite material as described above. FIGS. 16A-C provides a stylized illustration of an incorporation into FAPbI$_3$ perovskite material crystal lattice of the three ammonium compounds illustrated in FIG. 16. FIG. 16A is a stylized illustration incorporation of 1,8-diammonium octane into a FAPbI$_3$ perovskite material crystal lattice 7100. As illustrated by FIG. 16A, the 1,8-diammonium octane cation 7120 may substitute for two formamidinium cations 7110 in the perovskite material crystal lattice. FIG. 16B is a stylized illustration incorporation of bis(4-aminobutyl)-ammonium into a FAPbI$_3$ perovskite material crystal lattice 7200. As illustrated by FIG. 16B, the bis(4-aminobutyl)-ammonium cation 7220 may substitute for three formamidinium cations 7210 in the perovskite material crystal lattice. FIG. 16C is a stylized illustration incorporation of tris(4-aminobutyl)-ammonium into a FAPbI$_3$ perovskite material crystal lattice 7300. As illustrated by FIG. 16c, the tris(4-aminobutyl)-ammonium cation 7320 may substitute for four formamidinium cations 7310 in the perovskite material crystal lattice. In other embodiments, alkyl diammonium complexes with carbon chains between 2 and 20 carbon atoms may be added to a perovskite material. In some embodiments, a combination of ammonium complexes may be added to a perovskite material.

Tantalum and Niobium Oxide Nanoparticles

In certain embodiments, interfacial layers (IFLs) described throughout this disclosure may be layers of metal oxide nanoparticles. The metal (V) oxide nanoparticles include metal (V) oxide cores having the formula M$_2$O$_5$. In particular, both niobium (V) and tantalum (V) oxide nanoparticles may be utilized in electron transport material layers in perovskite material PV devices.

In general, metal oxides may function as electron transport layers (ETL) in a variety of photovoltaic devices. However, metal oxides have previously had limited utility in perovskite material PVs because they often require high annealing temperatures or oxidizing conditions for deposition, which may destabilize or degrade any perovskite material deposited prior to deposition of the metal oxides. Metal oxide nanoparticles decouple oxide formation from device fabrication. Metal oxide nanoparticles may be produced prior to perovskite material device production and may be soluble in a variety of solvents. Soluble metal oxide nanoparticles may be prepared by wet synthesis and functionalized with stable ligands to create soluble metal oxide inks that are processable at low temperatures under mild conditions, which decreases or eliminates damage to a previously deposited perovskite material layer. Both tantalum (V) oxide and niobium (V) oxide are ideal metal oxides for electron transport layers in perovskite material PV cells due to their very low ionization potentials (−8 eV vs vacuum), which allows them to effectively block holes from the cathode during device operation.

Figure 37:
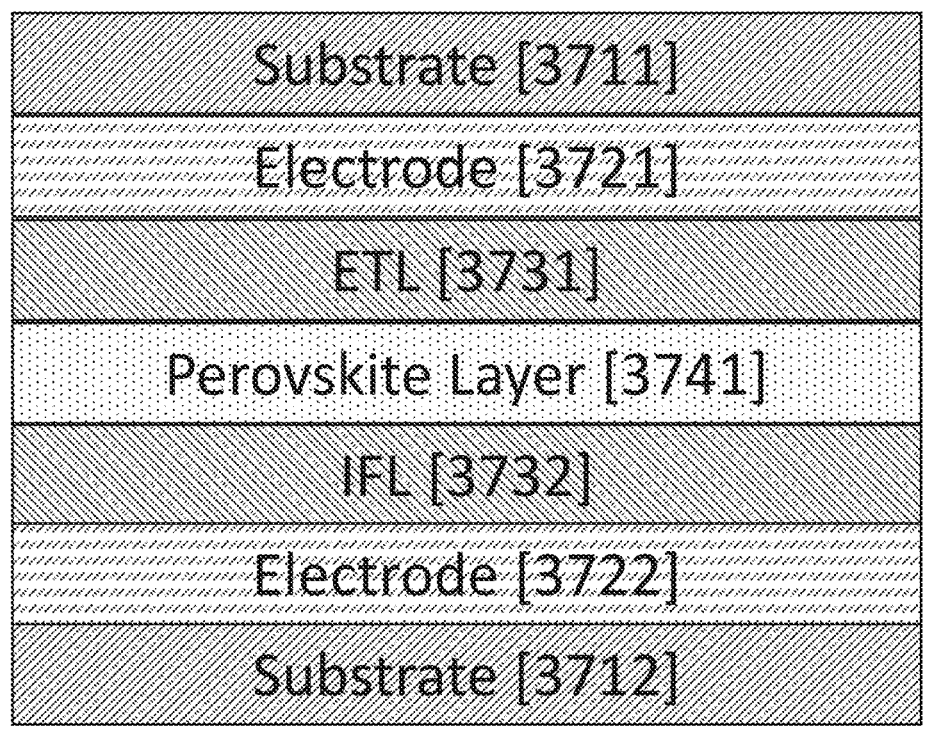
FIG. 37 is a stylized illustration of a perovskite material device, according to some embodiments of the present disclosure.

FIG. 37 is a stylized illustration of a perovskite material device 3700 incorporating a metal (V) oxide nanoparticle ETL, according to certain embodiments. Perovskite material device 3700 includes substrates 3711 and 3712, electrodes 3721 and 3722, IFL 3732, perovskite material layer 3741, and ETL layer 3731. Substrates 3711 and 3712 may include any substrate material disclosed herein, electrodes 3721 and 3722 may include any electrode material disclosed herein, and IFL 3732 may include any IFL material disclosed herein. In some embodiments, perovskite material layer 3741 may include any perovskite material disclosed herein. In particular embodiments, perovskite material 3741 may include perovskite materials disclosed herein that contain only formamidinium as an organic "C" cation. In a particular embodiment, perovskite material 3741 may be a bulky cation-containing formamidinium lead iodide perovskite as described herein. In another particular embodiment, perovskite material 3741 may be a formamidinium lead iodide perovskite that contains di-ammonium butane, as described herein. ETL layer 3731 includes metal (V) nanoparticles as described further herein and may also include any other material suitable as an IFL as described herein. ETL layer 3731, in particular embodiments, may include tantalum (V) oxide nanoparticles, niobium (V) oxide nanoparticles, or a combination thereof. In other embodiments, ETL layer 3731 may include nanoparticles that include an alloy of tantalum (V) and niobium (V), such nanoparticles may have a formula expressed as (Nb$_x$Ta$_{1-x}$)$_2$O$_5$, where x is a number between zero and 1. In some embodiments, ETL layer 3731 may include additional interfacial layers (IFLs). In some embodiments, ETL layer 3731 may be deposited by blade coating, drop casting, spin casting, slot-die printing, gravure coating, reverse gravure coating, screen printing, or ink-jet printing a metal (V) oxide nanoparticle ink produced by dissolving metal (V) oxide nanoparticles in a solvent prior to deposition.

Figure 38:
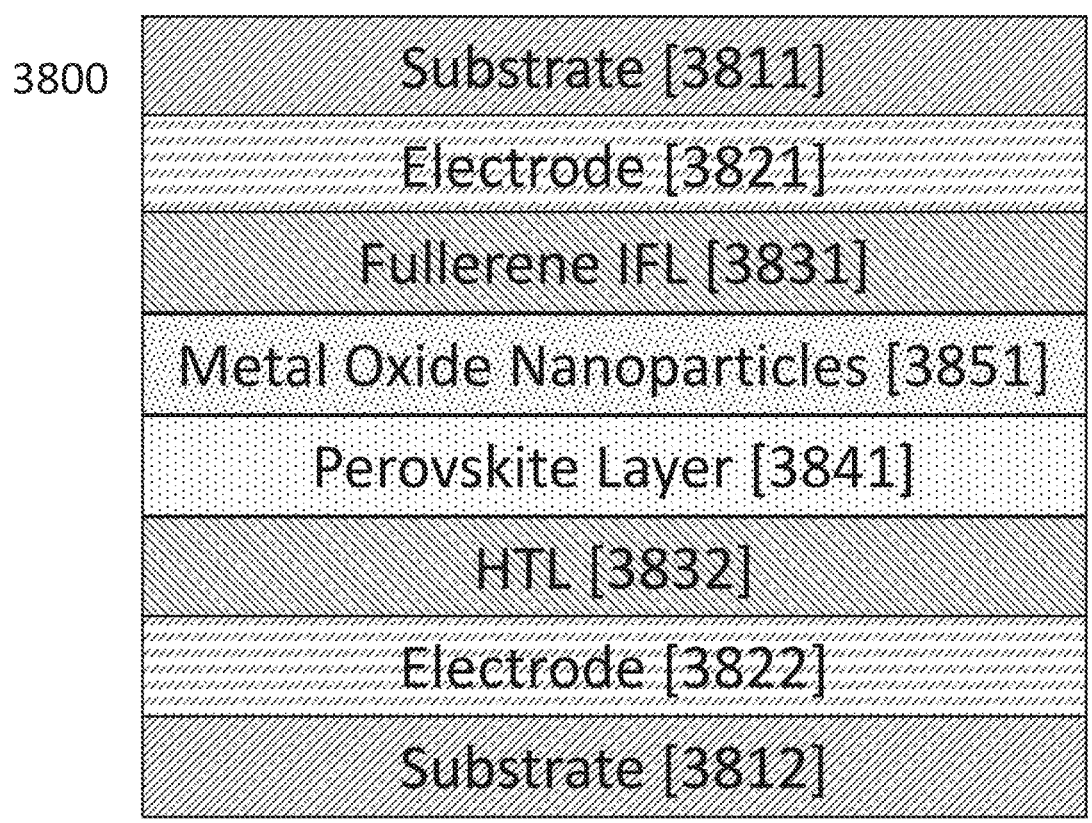
FIG. 38 is a stylized illustration of a perovskite material device, according to some embodiments of the present disclosure.

FIG. 38 is a stylized illustration of a perovskite material device 3800 incorporating a metal (V) oxide nanoparticle ETL, according to certain embodiments. Perovskite material device 3800 includes substrates 3811 and 3812, electrodes 3821 and 3822, hole transport layer (HTL) 3832, perovskite material layer 3841, and fullerene IFL 3831, and metal (V) oxide nanoparticle layer 3851. Substrates 3811 and 3812 may include any substrate material disclosed herein, electrodes 3821 and 3822 may include any electrode material disclosed herein, and HTL 3832 may include any IFL material disclosed herein that has hole transporting (p-type) properties. In some embodiments, perovskite material layer 3841 may include any perovskite material disclosed herein. In particular embodiments, perovskite material 3841 may include perovskite materials disclosed herein that contain only formamidinium as an organic "C" cation. In a particular embodiment, perovskite material 3841 may be a bulky cation-containing formamidinium lead iodide perovskite as described herein. In another particular embodiment, perovskite material 3841 may be a formamidinium lead iodide perovskite that contains di-ammonium butane, as described herein. Fullerene layer 3831 may include any fullerenes described herein, including, but not limited to, C60 and functionalized derivatives of C60. Metal (v) oxide nanoparticle layer 3851, includes metal (V) nanoparticles as described further herein, and in particular embodiments, may include tantalum (V) oxide nanoparticles, niobium (V) oxide nanoparticles, or a combination thereof. In some embodiments, metal (v) oxide nanoparticle layer 3851 may be deposited by blade coating, drop casting, spin casting, slot-die printing, gravure coating, reverse gravure coating, screen printing, or ink-jet printing a metal (V) oxide nanoparticle ink produced by dissolving metal (V) oxide nanoparticles in a solvent prior to deposition.

Figure 39:
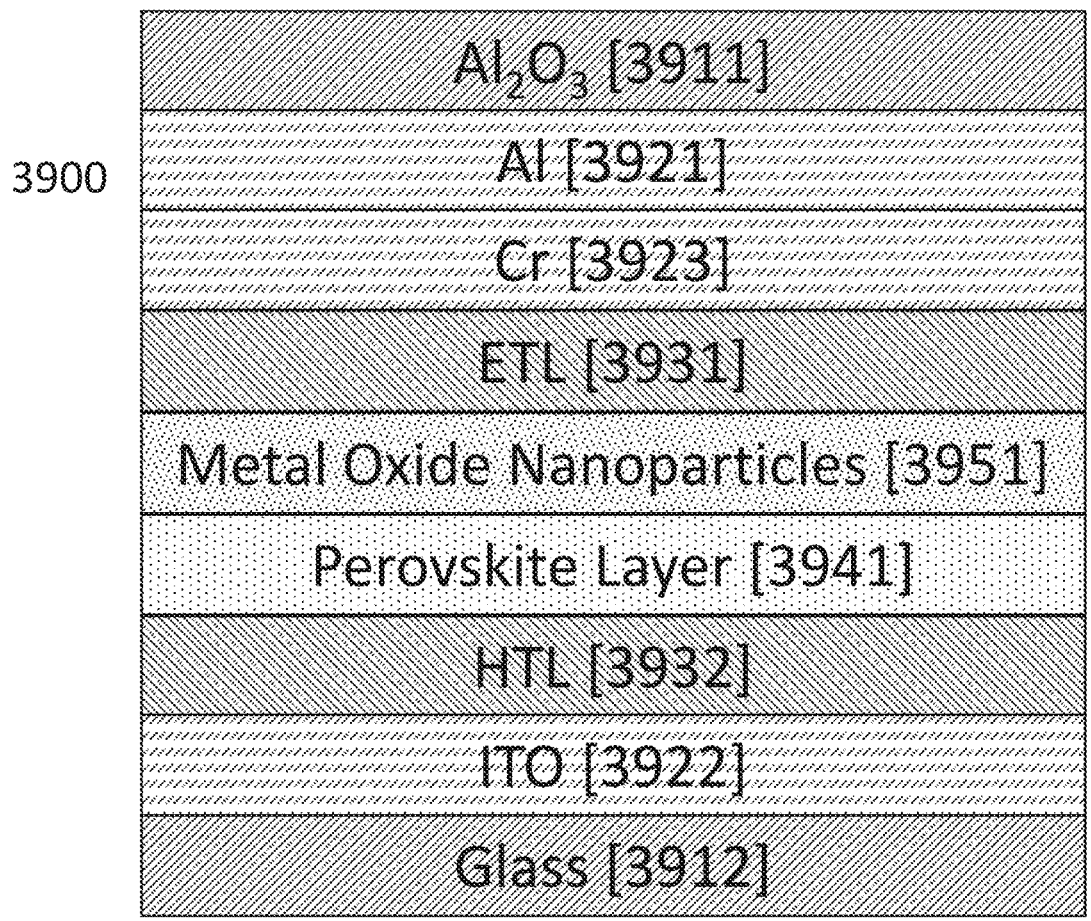
FIG. 39 is a stylized illustration of a perovskite material device, according to some embodiments of the present disclosure.

FIG. 39 is a stylized illustration of a perovskite material device 3900 incorporating a metal (V) oxide nanoparticle ETL, according to certain embodiments. Perovskite material device 3900 includes aluminum oxide (Al$_2$O$_3$) layer 3911, glass layer 3912, ITO layer 3922, chromium layer 3923, aluminum layer 3921, HTL 3932, perovskite material layer 3941, ETL 3931, and metal (V) oxide nanoparticle layer

3951. ITO layer 3922 and Cr layer 3923 and Al layer 3921 function as electrodes in a manner similar to any electrode layer illustrate with respect to other figures herein. HTL 3932 may include any IFL material disclosed herein that has hole transporting (p-type) properties. In some embodiments, perovskite material layer 3941 may include any perovskite material disclosed herein. In particular embodiments, perovskite material 3941 may include perovskite materials disclosed herein that contain only formamidinium as an organic "C" cation. In a particular embodiment, perovskite material 3941 may be a bulky cation-containing formamidinium lead iodide perovskite as described herein. In another particular embodiment, perovskite material 3941 may be a formamidinium lead iodide perovskite that contains di-ammonium butane, as described herein. ETL 3931 may include any IFL material disclosed herein that has electron transporting (n-type) properties. Metal (v) oxide nanoparticle layer 3951, includes metal (V) nanoparticles as described further herein, and in particular embodiments, may include tantalum (V) oxide nanoparticles, niobium (V) oxide nanoparticles, or a combination thereof. In some embodiments, metal (v) oxide nanoparticle layer 3951 may be deposited by blade coating, drop casting, spin casting, slot-die printing, gravure coating, reverse gravure coating, screen printing, or ink-jet printing a metal (V) oxide nanoparticle ink produced by dissolving metal (V) oxide nanoparticles in a solvent prior to deposition.

Figure 40:
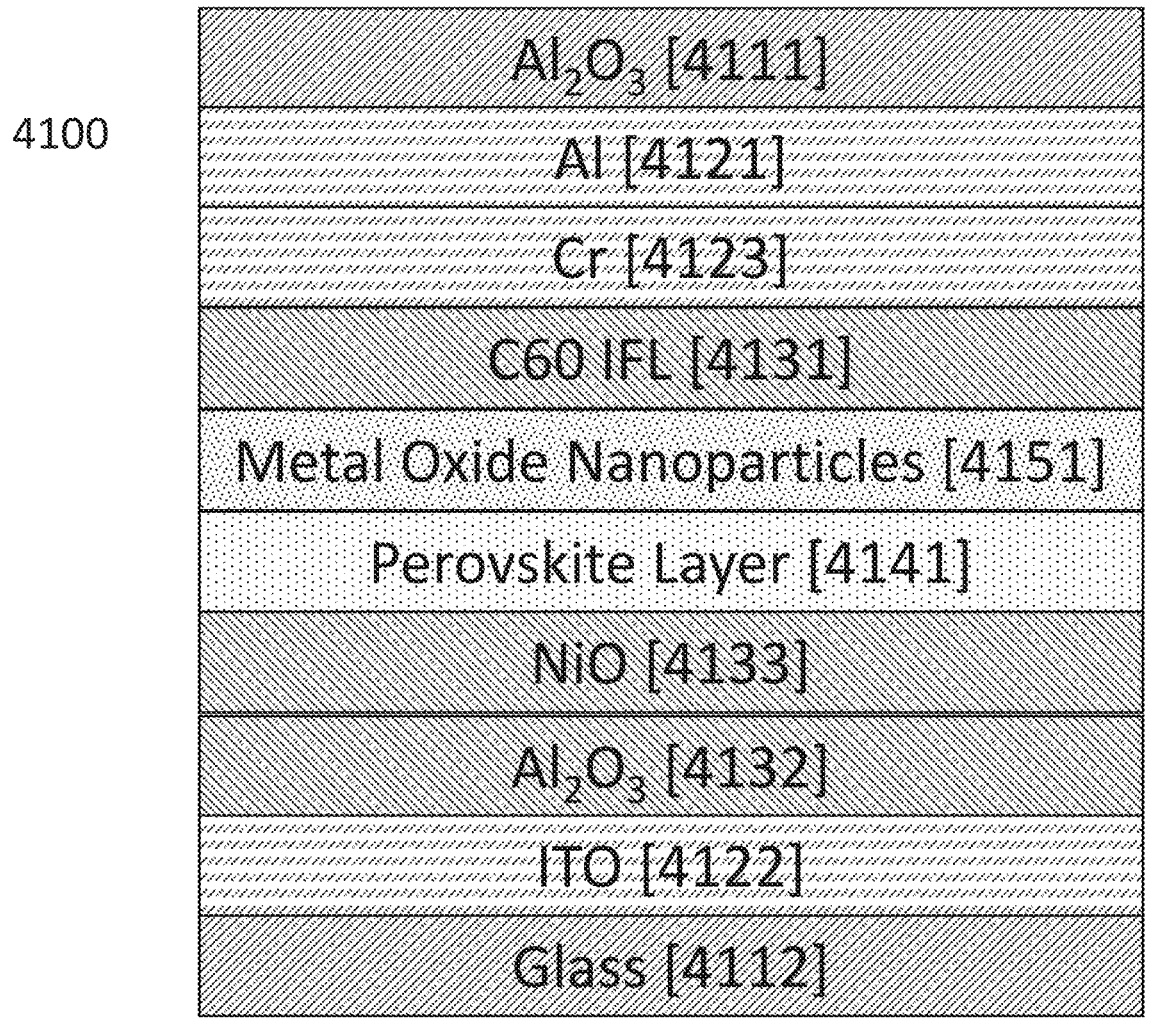
FIG. 40 is a stylized illustration of a perovskite material device, according to some embodiments of the present disclosure.

FIG. 40 is a stylized illustration of a perovskite material device 4100 incorporating a metal (V) oxide nanoparticle ETL, according to certain embodiments. Perovskite material device 4100 includes aluminum oxide ($Al_2O_3$) layer 4111, glass layer 4112, ITO layer 4122, chromium layer 4123, aluminum layer 4121, $Al_2O_3$ layer 4132, NiO layer 4133, perovskite material layer 4141, C60 IFL 4131, and metal (V) oxide nanoparticle layer 4151. ITO layer 4122 and Cr layer 4123 and Al layer 4121 function as electrodes in a manner similar to any electrode layer illustrate with respect to other figures herein. NiO layer 4133 and $Al_2O_3$ layer 4132 may function together as an HTL similar to HTL 3832 of FIG. 38. In some embodiments, perovskite material layer 4141 may include any perovskite material disclosed herein. In particular embodiments, perovskite material 4141 may include perovskite materials disclosed herein that contain only formamidinium as an organic "C" cation. In a particular embodiment, perovskite material 4141 may be a bulky cation-containing formamidinium lead iodide perovskite as described herein. In another particular embodiment, perovskite material 4141 may be a formamidinium lead iodide perovskite that contains di-ammonium butane, as described herein. C60 IFL 4131 may include C60 molecules and functionalized derivatives of C60. Metal (v) oxide nanoparticle layer 4151, includes metal (V) nanoparticles as described further herein, and in particular embodiments, may include tantalum (V) oxide nanoparticles, niobium (V) oxide nanoparticles, or a combination thereof. In some embodiments, metal (v) oxide nanoparticle layer 4151 may be deposited by drop casting, spin casting, slot-die printing, screen printing, or ink-jet printing a metal (V) oxide nanoparticle ink produced by dissolving metal (V) oxide nanoparticles in a solvent prior to deposition.

Figure 41:
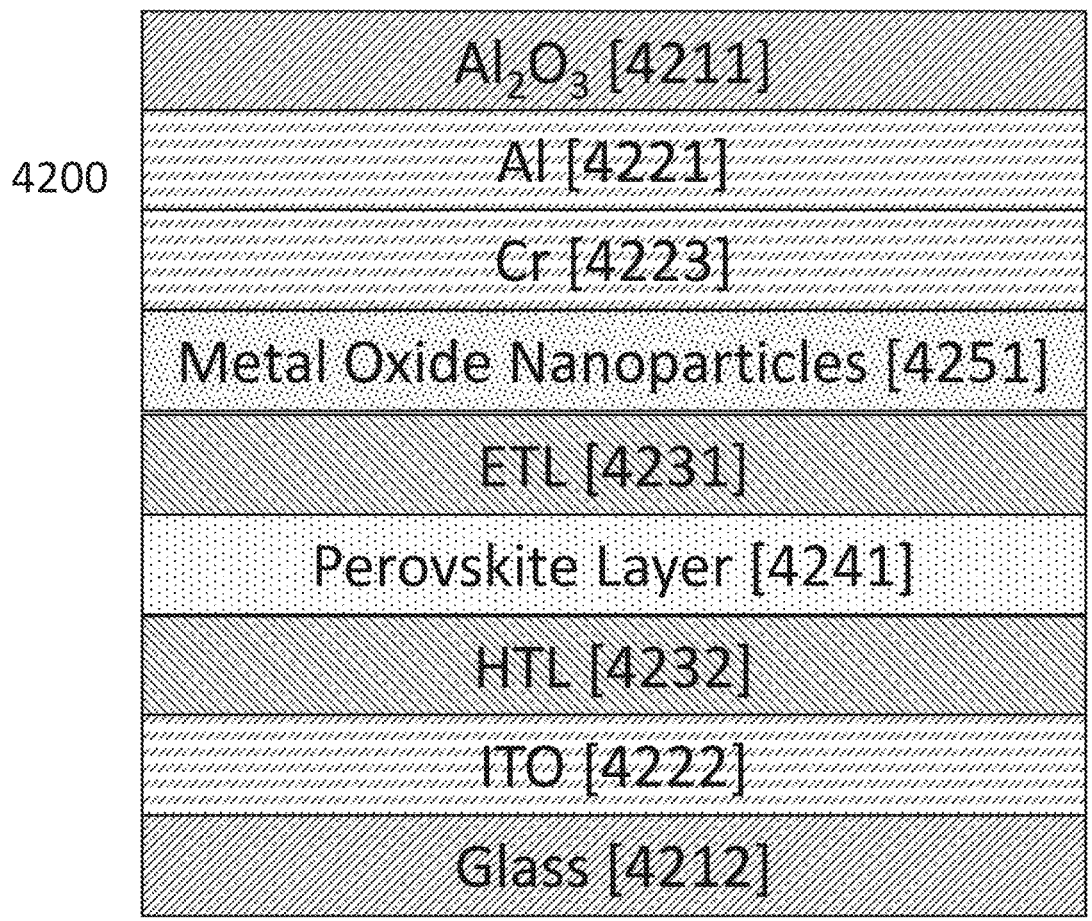
FIG. 41 is a stylized illustration of a perovskite material device, according to some embodiments of the present disclosure.

FIG. 41 is a stylized illustration of a perovskite material device 4200 incorporating a metal (V) oxide nanoparticle ETL, according to certain embodiments. Perovskite material device 4200 includes $Al_2O_3$ layer 4211, glass layer 4212, ITO layer 4222, chromium layer 4223, aluminum layer 4221, HTL 4232, perovskite material layer 4241, ETL 4231, and metal (V) oxide nanoparticle layer 4251. ITO layer 4222 and Cr layer 4223 and Al layer 4221 function as electrodes in a manner similar to any electrode layer illustrated with respect to other figures herein. HTL 4232 may include any IFL material disclosed herein that has hole transporting (p-type) properties. In some embodiments, perovskite material layer 4241 may include any perovskite material disclosed herein. In particular embodiments, perovskite material 4241 may include perovskite materials disclosed herein that contain only formamidinium as an organic "C" cation. In a particular embodiment, perovskite material 4241 may be a bulky cation-containing formamidinium lead iodide perovskite as described herein. In another particular embodiment, perovskite material 4241 may be a formamidinium lead iodide perovskite that contains di-ammonium butane, as described herein. ETL 4231 may include any IFL material disclosed herein that has electron transporting (n-type) properties. Metal (v) oxide nanoparticle layer 4251, includes metal (V) oxide nanoparticles as described further herein, and in particular embodiments, may include tantalum (V) oxide nanoparticles, niobium (V) oxide nanoparticles, or a combination thereof. In some embodiments, metal (v) oxide nanoparticle layer 4251 may be deposited by blade coating, drop casting, spin casting, gravure coating, reverse gravure coating, slot-die printing, screen printing, or ink-jet printing a metal (V) oxide nanoparticle ink produced by dissolving metal (V) oxide nanoparticles in a solvent prior to deposition. In a particular embodiment, ETL 4231 may be an electron transport material that extracts electrons from the perovskite material layer 4241 quickly but does not effectively block holes, in such an arrangement the metal (V) oxide nanoparticle layer 4251 may block holes that ETL 4231 does not.

In certain embodiments, a metal (v) oxide nanoparticle layer may be utilized as any IFL layer described within this disclosure. For example, metal (v) oxide nanoparticles may be utilized as a whole or part of any IFLs illustrated in FIG. 1, 2, 3, or 4. In some embodiments, metal (v) oxide nanoparticles may be included in a single layer of a multi-layer IFL as described herein. The metal (v) oxide nanoparticle s of the present disclosure, may be disposed adjoining a perovskite material layer in perovskite material PV devices. For example, the metal (v) oxide nanoparticles of the present disclosure may be utilized as IFL 1050 of FIG. 1, IFL 3909 or CTL 3910 (or a combination of both) of FIG. 2, IFL 3909*a* or CTL 3910*a* (or a combination of both) of FIG. 3, or IFL 3909*b* or CTL 3910*b* (or a combination of both) of FIG. 4. Methods for synthesizing and depositing metal (v) oxide particles, and in particular tantalum (V) oxide nanoparticles and niobium (V) oxide nanoparticles, are described below.

Figure 42:
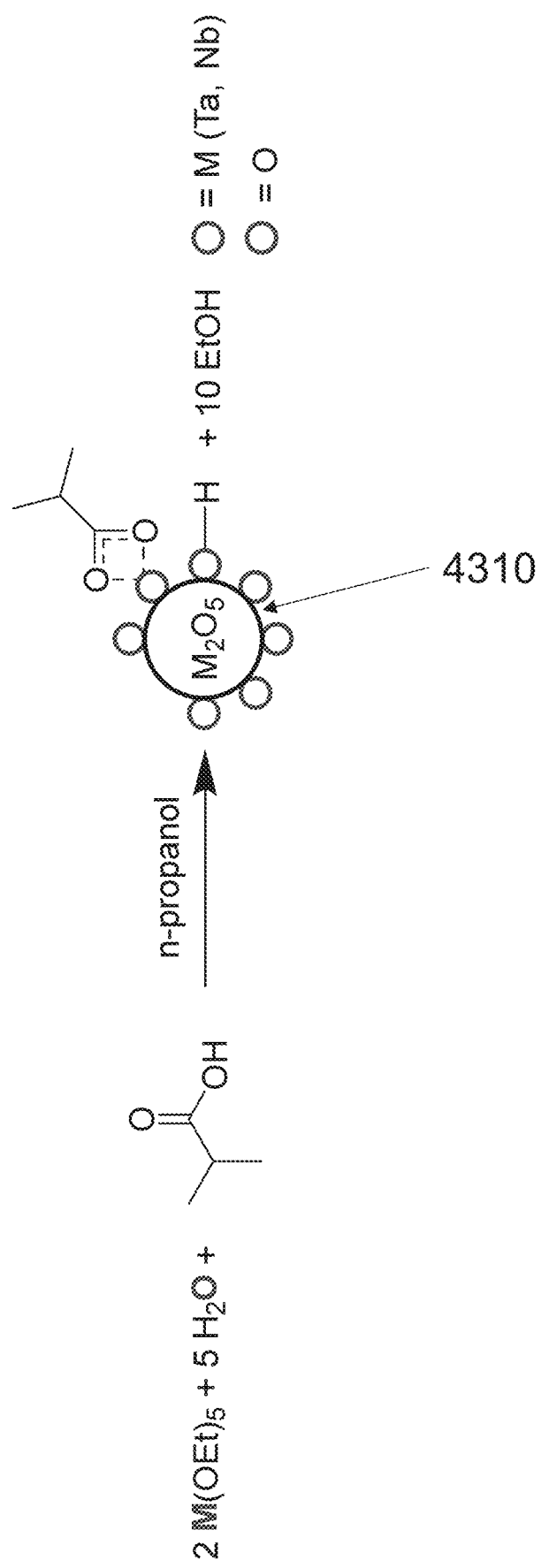
FIG. 42 is a stylized illustration of a reaction to form metal oxide nanoparticle cores, according to some embodiments of the present disclosure.

An example reaction for preparing metal (V) oxides nanoparticle cores is illustrated in FIG. 42. The metal (V) oxides nanoparticle cores are synthesized from metal (V) alkoxide precursors ($M(OR)_5$) and water in the presence of an organic acid. In some embodiments the organic acid may be an alkylcarboxylic acid. In particular embodiments, the metal may be tantalum (V) or niobium (V). In some embodiments, the metal (V) alkoxide precursors may be selected from the group consisting of methoxides, ethoxides, n-propoxides, isopropoxides, and (n, iso, sec, or tert)-butoxides, and combinations thereof. In a particular embodiment, the metal (V) alkoxide precursor may be a metal (V) ethoxide ($M(OEt)_5$). In the embodiment illustrated in FIG. 42, the organic acid is isobutyric acid, and the reaction is carried out in an n-propanol solution. However, in other embodiments any alcohol may be used, including but not limited to n-butanol, 2-butanol, 2-methylbutan-2-ol. Additionally, the alcohol solution may or may not include water. As illustrated in FIG. 42, the resulting metal (V) oxide nanoparticle cores 4310 have a ratio of five oxygen atoms to two metal atoms. However, it should be noted that the ratio of five oxygen atoms to two metal atoms illustrated at the surface of the nanoparticle of FIG. 42 is done for illustrative purposes only. It should be understood that the surface of nanoparticles may be irregular or deviate from "perfect" stoichiometry due to internal and external impurities, variances in surface structure compared to bulk structure, or surface doping. Hydrogen atoms may bond to the oxygen atoms at the surface of the metal (V) oxide nanoparticle cores 4310, and organic ligands may bond to the metal atoms at the surface. In the embodiment illustrated in FIG. 42, the isobutyric acid ligand bonds to the metal atoms on the surface of the nanoparticle core 4310. In some embodiments, the nanoparticle cores may be left in solution prior to the ligand exchange process described below. In other embodiments, after completion of the reaction to form the nanoparticle cores, the nanoparticle cores may be isolated by any method known in the art. For example, one method of isolating the nanoparticle cores may include centrifuging the suspension of nanoparticles in the n-propanol solution to separate the nanoparticle cores from the solution, dissolving the separate nanoparticle cores in a solvent, adding a precipitating compound to the solution to precipitate the nanoparticle cores, and centrifuging the precipitate nanoparticle cores to separate them from the solution. In some embodiments the separated nanoparticles cores may be dissolved in a further solvent, precipitated and centrifuged again to further wash the nanoparticle cores. In particular embodiments, the nanoparticle cores may be centrifuged at 5000-15000 rpm for 1 to 15 minutes, dissolved in a hexane solution after separation, and precipitated with methyl acetate added to the hexane solution. In particular embodiments, the nanoparticle cores may be centrifuged at 10000 rpm for 10 minutes, dissolved in a hexane solution after separation, and precipitated with methyl acetate added to the hexane solution.

Figure 43:
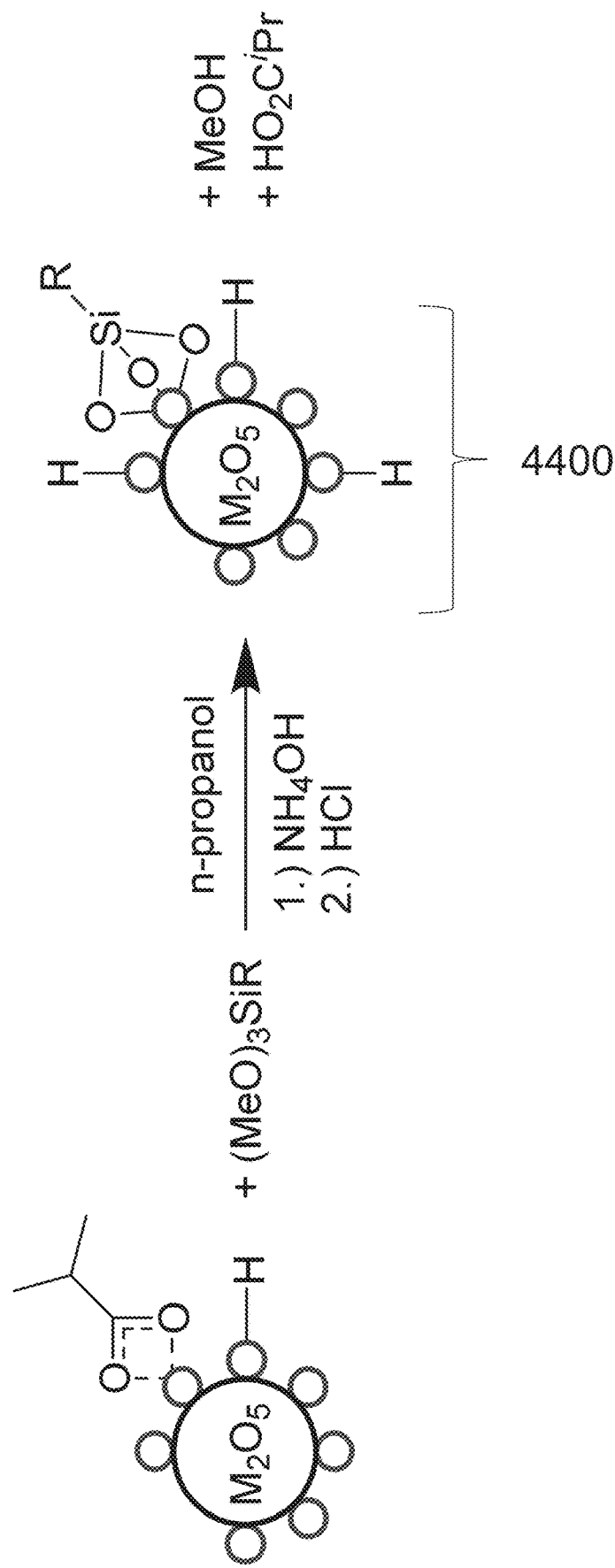
FIG. 43 is a stylized illustration of a ligand exchange reaction, according to some embodiments of the present disclosure.

After synthesis of nanoparticle cores 4310 as illustrated in FIG. 42, next the isobutyric acid ligands may be exchanged with alkylsiloxane ligands, as illustrated in FIG. 43. In particular embodiments, the alkylsiloxane ligands may be isobutylsiloxane. First the nanoparticle cores are mixed in an alcohol solution with one or more trialkoxyalkylsilanes. In particular embodiments, the trialkoxyalkylsilane is trimethoxy(isobutyl)silane. In other embodiments the trialkoxyalkylsilane may be selected from the group consisting of tri(alkoxy)isobutylsilane, tri(alkoxy)allylsilane, tri(alkoxy)vinylsilane, tri(alkoxy)-n-propylsilane, tri(alkoxy)-n-butylsilane, tri(alkoxy)-sec-butylsilane, tri(alkoxy)-tert-butylsilane, tri(alkoxy)phenylsilane, tri(alkoxy)-n-octylsilane, tri(alkoxy)isooctylsilane tri(alkoxy)-n-dodecylsilane, tri(alkoxy)-4-(trimethylsilyl)phenylsilane, tri(alkoxy)-p-tolylsilane, tri(alkoxy)-4-fluorophenylsilane, tri(alkoxy)-4-chlorophenylsilane, tri(alkoxy)-4-bromophenylsilane, tri(alkoxy)-4-iodophenylsilane, tri(alkoxy)-4-cyanophenylsilane, tri(alkoxy)benzylsilane, tri(alkoxy)methylsilane, tri(alkoxy)ethylsilane, tri(alkoxy)-4-(trifluoromethyl)phenylsilane, tri(alkoxy)-4-ammoniumbutylsilane, and combinations thereof, where "alkoxy" is a methoxy, ethoxy, isopropoxy, tert-butoxy, or phenoxy group. Additionally, any isomers including orthro and meta isomers of the forgoing compounds may be selected as the trialkoxyalkylsilane. In the embodiment illustrated in FIG. 43, the alcohol solution is an n-propanol solution. In other embodiments, the alcohol solution may include any alcohol including, but not limited to, n-butanol, 2-butanol, and 2-methylbutan-2-ol. Additionally, the alcohol solution may or may not include water in addition to the alcohol.

Next ammonium hydroxide ($NH_4OH$) is added to the solution followed by addition of aqueous HCl to complete the ligand exchange. In some embodiments, HCl gas may be sparged through the solution. After the ligand exchange reaction has completed, metal (V) nanoparticles 4400 are formed and precipitate out of the solution. In particular embodiments, the alkylsiloxane ligand may be isobutylsiloxane. Depending on the trialkoxyalkylsilane chosen (such as those described above), the resulting alkylsiloxane ligands may be selected from the group consisting of isobutylsiloxane, allylsiloxane, vinyl siloxane, n-propylsiloxane, n-butylsiloxane, sec-butylsiloxane, tert-butylsiloxane, phenyl siloxane, n-octylsiloxane, isooctylsiloxane n-dodecylsiloxane, 4-(trimethylsilyl)phenylsiloxane, para-tolylsiloxane, 4-fluorophenylsiloxane, 4-chlorophenylsiloxane, 4-bromophenylsiloxane, 4-iodophenylsiloxane, 4-cyanophenylsiloxane, benzylsiloxane, methylsiloxane, ethylsiloxane, 4-(trifluoromethyl)phenylsiloxane, 4-ammoniumbutylsiloxane, and combinations thereof. The alkylsiloxane ligand may include any ortho and meta isomers of the forgoing compounds if an ortho or meta isomer of the corresponding trialkoxyalkylsilane was selected. Alkylsiloxane ligands have been observed provide adequate solubility in organic solvents used in PV solution-based processing and deposition methods and have been observed to provide the metal (V) nanoparticles with electronic properties highly compatible with perovskite materials used in PV devices. For example, the alkylsiloxane ligand composition was determined to maximized solubility for precursor inks and to minimize series resistance in devices. After formation, the nanoparticles may be isolated via centrifugation and washed one or more times with antisolvents. After washing, the nanoparticles may be dried and then stored or dissolved in organic solvents. In particular embodiments, the dried metal (V) oxide nanoparticles may be dissolved in chlorobenzene to form a nanoparticle ink.

Figure 44:
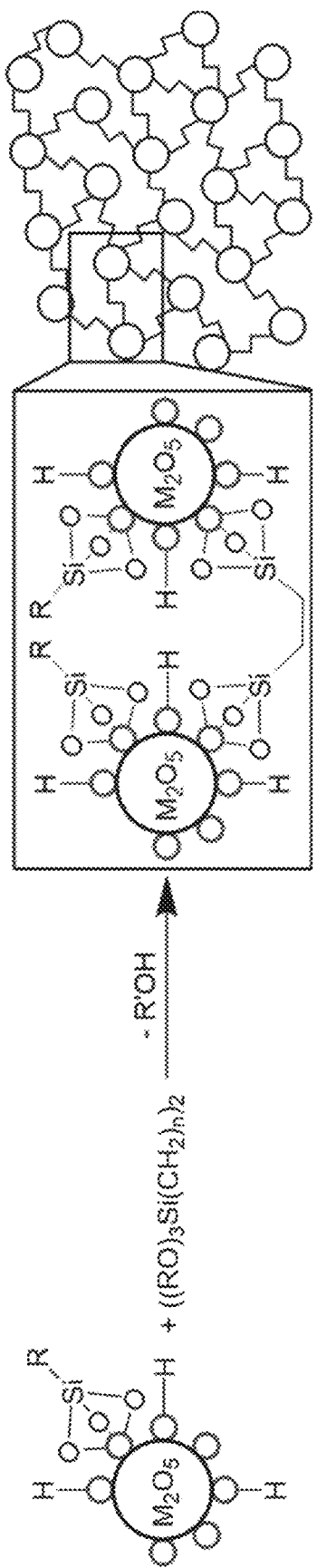
FIG. 44 is a stylized illustration of metal nanoparticle crosslinking reaction, according to some embodiments of the present disclosure.

In some embodiments, the metal (V) oxide nanoparticles may be crosslinked by a reaction illustrated in FIG. 44. As illustrated in FIG. 44, the alkylsiloxane-substituted nanoparticles may be reacted with one or more alkoxylalkylsilanes to crosslink the alkylsiloxane ligands. Crosslinking metal (v) oxide nanoparticles is possible by using molecules with two (or more) binding groups, such as bis-alkoxylalkylsilanes, or via radical initiated polymerization of alkene groups (e.g., vinyl or allyl). Crosslinking may link the nanoparticles in a robust matrix. Advantages of crosslinked nanoparticles may include increased thermal stability and resistance to penetration my moisture and other compounds that can degrade the perovskite material photoactive layer, leading to slower device performance degradation and longer device life. In some embodiments, crosslinking of the metal (V) oxide nanoparticles may be carried out in solution. In these embodiments, dimer or trimer crosslinked nanoparticles may be formed, as higher levels of crosslinking may inhibit the solubility of the crosslinked nanoparticles. In other embodiments, crosslinking of the metal (V) oxide nanoparticles may be carried out after deposition of the nanoparticles (for example, after deposition onto a perovskite material layer). In such an embodiment, any degree of crosslinking may be achieved because the nanoparticles have already been deposited and solubility is not a concern at this stage.

Figure 45:
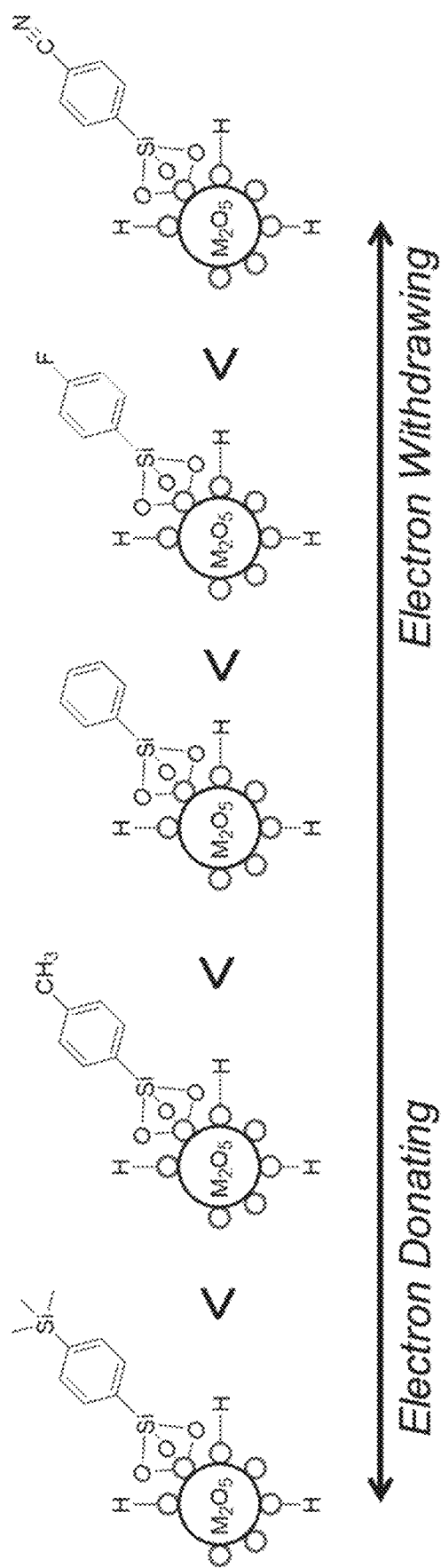
FIG. 45 is a stylized illustration of several metal oxide nanoparticles, according to some embodiments of the present disclosure.

Selection of various alkoxylalkylsilanes during ligand exchange may vary the electronic properties of the metal (V)

oxide nanoparticles. FIG. 45 illustrates several metal (V) nanoparticles with different alkylsiloxane ligands. As can be seen in FIG. 45 some alkylsiloxane ligands are more electron withdrawing, some are more electron donating, and some are neither electron withdrawing or electron donating, where electron donating and electron withdrawing refer to whether the ligand donates or withdraws electron from the metal (V) oxide nanoparticle core. A ligand that is more electron donating results in a more n-type metal (V) oxide nanoparticle and a ligand that is more electron withdrawing results in a more p-type metal (V) oxide nanoparticle. Selection of ligands allows the electronic properties of the metal (V) oxide nanoparticles to be fine-tuned, allowing the metal (V) oxide nanoparticle layer to be fine-tuned for particular perovskite material compositions and band gaps. Additionally, the metal (V) oxide nanoparticles may be further tuned by inclusion of other metals in the metal ethoxide precursors. The metal ethoxide precursors may include other metals with properties similar to tantalum and niobium or may be doped with other metals. For example, the metal ethoxide precursors may be doped with Ti, Zr, or Hf to produce a more p-type oxide nanoparticle or may be doped with Cr, Mo, or W to produce a more n-type oxide nanoparticle. In some embodiments, the metal oxide core may be doped with a metal. For example, in some embodiments the metal oxide core may be doped with Ti, Zr, Hf, Cr, Mo, W, V, or any combination thereof.

Figure 47:
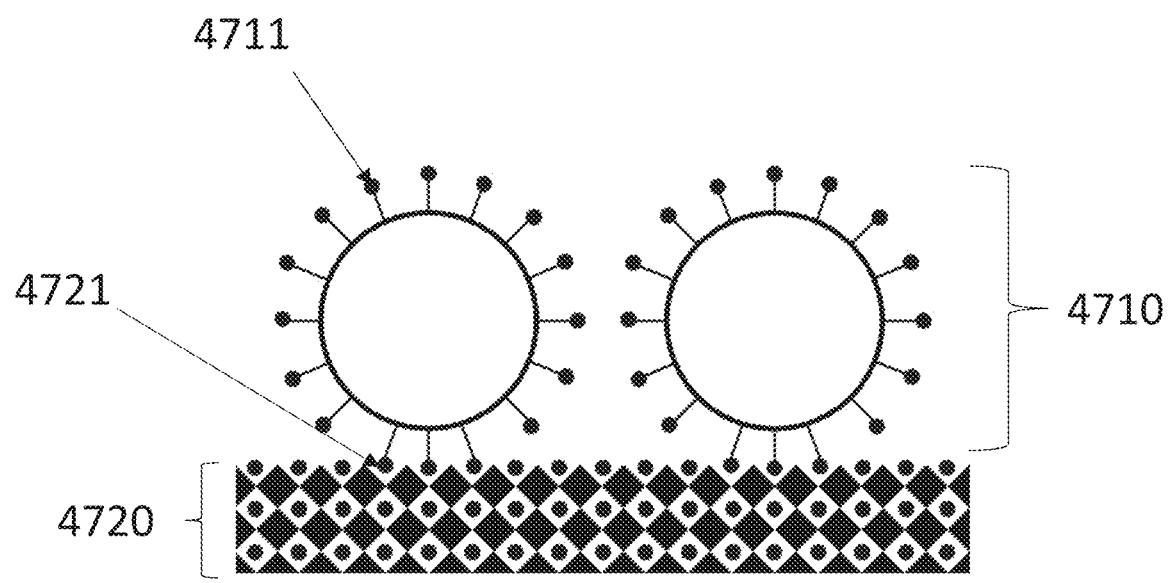
FIG. 47 is a stylized illustration of ammonium-functionalized metal oxide nanoparticles on the surface of a perovskite material, according to some embodiments of the present disclosure.

Shorter alkyl groups (e.g., vinyl) may provide greater conductivity between nanoparticles while longer alkyl groups (e.g., octyl) may provide greater hydrophobicity, acting to repel water from the photoactive layer. In some embodiments, the alkyl groups of the alkoxylalkylsilanes may be functionalized. For example, the alkyl group could be terminated with an ammonium group, which may provide passivation of an "C"-site (e.g. ammonium, formamidinium or other cation incorporated into the perovskite material as the "C" in the formula $CMX_3$, or other perovskite material formulas, as described here) vacancy at the surface of the perovskite material lattice, as illustrated in FIG. 47.

Figure 46:
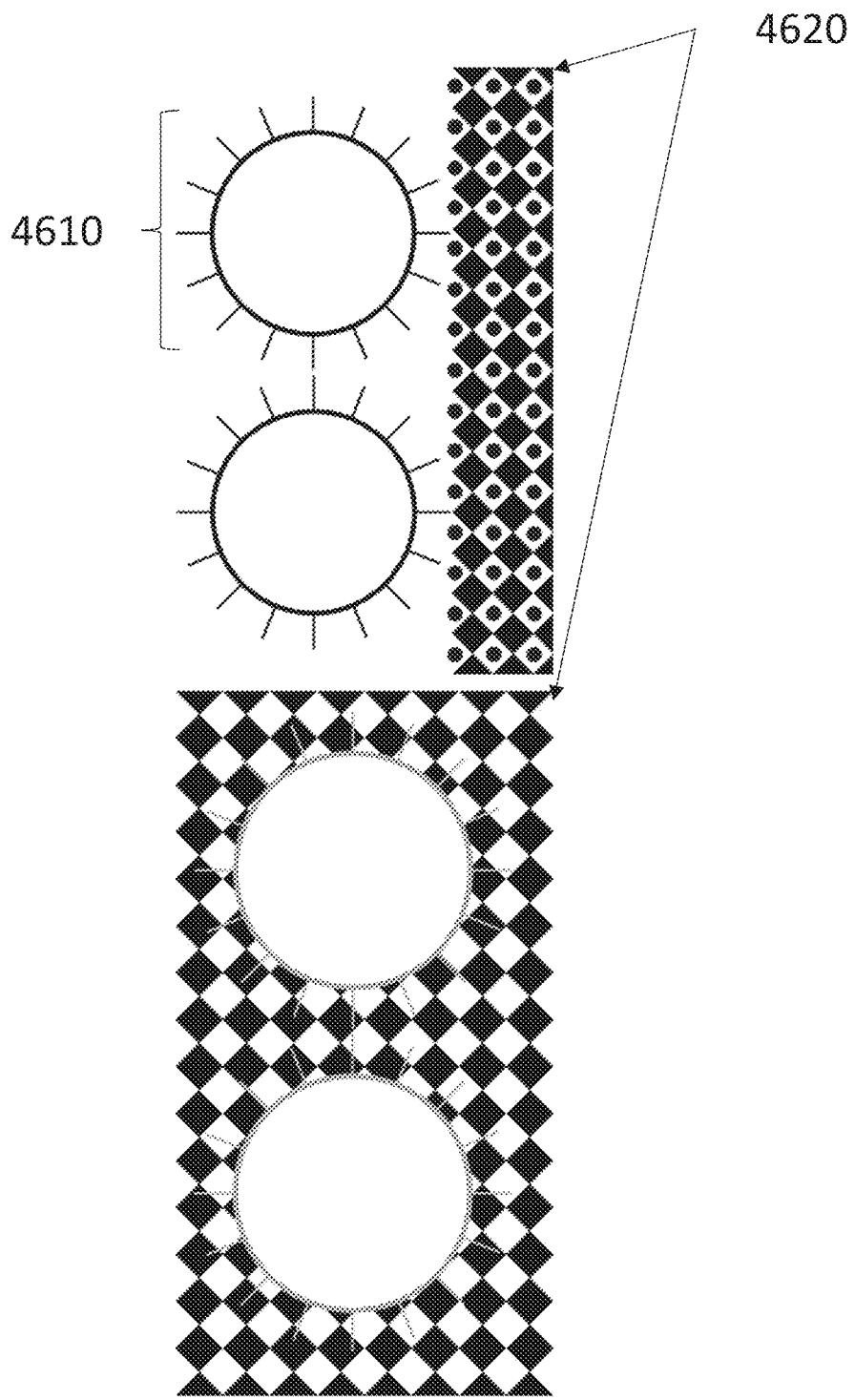
FIG. 46 is a stylized illustration of a metal oxide nanoparticles on the surface of a perovskite material, according to some embodiments of the present disclosure.

FIG. 46 provides a stylized illustration of metal (V) nanoparticles 4610 disposed on the surface of a perovskite material 4620. FIG. 47 provides a stylized illustration of metal (V) nanoparticles 4710 with ammonium-functionalized ligands disposed on the surface of a perovskite material 4720. The ammonium groups 4711 of the metal (V) nanoparticles may passivate the surface of a perovskite material by filing uncoordinated sites 4721 on the surface of the perovskite material 4720, leading to better electronic performance and stability.

Perovskite material devices incorporating metal (V) oxide nanoparticles may be constructed according to the methods disclosed herein. Individual layers of PIN architecture perovskite material devices, such as electrodes, IFLs, and perovskite material layers, may be deposited according to the methods disclosed herein or as are known in the art. Metal (V) oxide nanoparticles may be deposited onto the perovskite material layer, or other layer in the device, by blade coating, drop casting, spin casting, slot-die printing, screen printing, or ink-jet printing a metal (V) oxide nanoparticle ink.

A particular embodiment of a method for incorporating tantalum (V) oxide nanoparticles into a perovskite material PV device is described below. First, a glass substrate may be patterned with a transparent conductive oxide (e.g. ITO, FTO, or any other transparent electrode material disclosed herein). Next, hole transport layers, $Al_2O_3$ and NiO, are deposited sequentially by drop casting, spin casting, gravure coating, blade coating, reverse gravure coating, slot-die printing, screen printing, or ink-jet printing. After the layer of $Al_2O_3$ and NiO are deposited, they may be annealed. Next a perovskite material is deposited onto the previously deposited hole transport layers. In some embodiments, a two-step perovskite method as described herein may be used. In particular embodiments, a two-step perovskite method incorporating chloride into the perovskite precursors, as described herein, may be used to deposit a $Cs_xFA_{1-x}PbI_{3-y}Cl_y$ perovskite material layer on top of the hole transport layers. Bulky organic cations, including benzylammonium, in some embodiments, may also be incorporated in the perovskite material by the methods described herein. After deposition, the perovskite material may be annealed as described with respect to the methods of perovskite deposition disclosed herein.

Next, metal (V) oxide nanoparticle ink are deposited onto the layer stack. In some embodiments, the metal (V) oxide nanoparticle ink may be deposited in a controlled atmosphere environment, such as an inert environment. In particular embodiments, a tantalum (V) oxide nanoparticle ink or niobium (V) oxide nanoparticle ink may be deposited onto the perovskite material layer. The metal (V) nanoparticles may be formed by the methods described above. The metal (V) nanoparticle ink may be deposited by blade coating, drop casting, blade coating, spin casting, gravure coating, reverse gravure coating, slot-die printing, screen printing, or ink-jet printing. The metal (V) oxide nanoparticle solution may be deposited so as to form a metal (V) oxide nanoparticle layer between 1 nm and 100 nm thick. In some embodiments, the metal (V) oxide nanoparticle solution may be deposited so as to form a metal (V) oxide nanoparticle layer between 20 nm and 60 nm thick. In a particular embodiment, metal (V) oxide nanoparticle solution may be deposited so as to form a metal (V) oxide nanoparticle layer about 40 nm thick. Between 0.1 L and 0.2 L of metal (V) oxide nanoparticle ink may be deposited per square meter of substrate, and in a particular embodiment 0.16 L of metal (V) oxide nanoparticle ink may be deposited per square meter of substrate.

In some embodiments, a tantalum (V) oxide nanoparticle ink comprising tantalum (V) oxide nanoparticles in chlorobenzene at a concentration between about 1 mg tantalum (V) oxide nanoparticles per mL of chlorobenzene and 10 mg tantalum (V) oxide nanoparticles per mL of chlorobenzene may be deposited onto the perovskite material layer by spin coating. In a particular embodiment, a tantalum (V) oxide nanoparticle ink comprising tantalum (V) oxide nanoparticles in chlorobenzene at a concentration of about 4 mg tantalum (V) oxide nanoparticles per mL of chlorobenzene is deposited onto the perovskite material layer by spin coating. In other embodiments, a tantalum (V) oxide nanoparticle ink comprising tantalum (V) oxide nanoparticles in chlorobenzene at a concentration between about 1 mg tantalum (V) oxide nanoparticles per mL of chlorobenzene and 10 mg tantalum (V) oxide nanoparticles per mL of chlorobenzene may be deposited onto the perovskite material layer by blade coating. In a particular embodiment, a tantalum (V) oxide nanoparticle ink comprising tantalum (V) oxide nanoparticles in chlorobenzene at a concentration of about 4 mg tantalum (V) oxide nanoparticles per mL of chlorobenzene is deposited onto the perovskite material layer by blade coating. When the metal (V) oxide nanoparticle ink is deposited by blade coating, the blade height may be set between 1100 um and 1400 μm. In some embodiments the metal (V) oxide nanoparticle solution may be filtered before deposition onto the perovskite material layer.

After deposition, the metal (V) oxide nanoparticle layer may be annealed. Annealing, in some embodiments, may occur for between 3 and 20 minutes at a temperature between 50° C. and 140° C. In particular embodiments, annealing may occur for between 4 and 10 minutes at a temperature between 50° C. and 80° C. In a particular embodiment, annealing occurs for about 5 minutes at a temperature of about 55° C.

Next, a C60 layer may be deposited onto the metal (V) oxide nanoparticle layer. After deposition of the C60 layer, one or metal electrode layers such as Cr, Al, or Cu or one or more organic electrode layers such as bathocuproine (BCP) may be deposited onto the C60 layer. After deposition of the electrode layers, a top "sealing" or encapsulant layer may be deposited to protect the device from moisture and damage resulting from intrusion of other environmental contaminants into the PV device.

Figure 48:
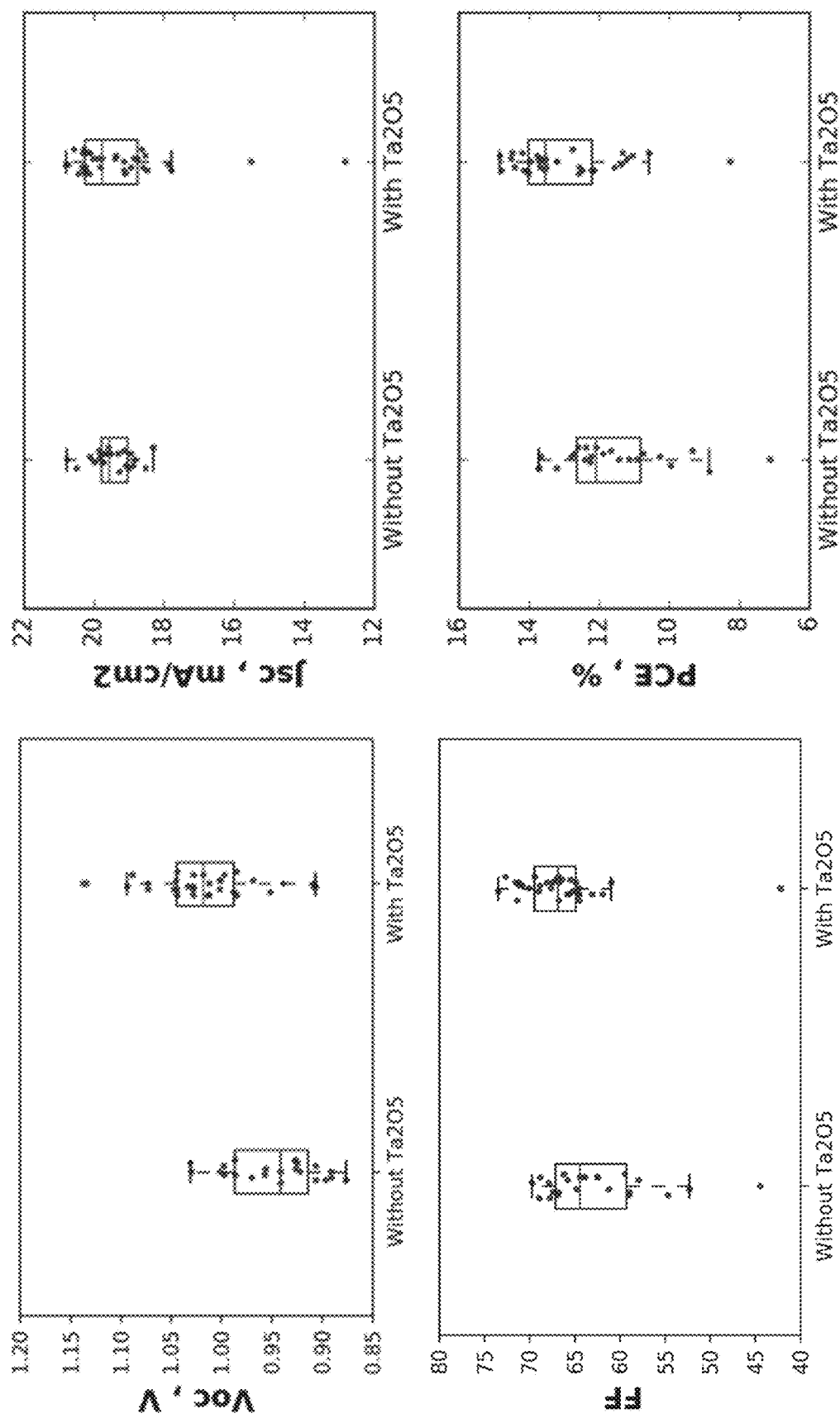
FIG. 48 illustrates box plots for open-circuit voltage (Voc), short-circuit current density (Jsc), Fill Factor (FF) and power conversion efficiency (PCE) for perovskite material photovoltaic devices, according to some embodiments of the present disclosure.

FIG. 48 shows box plots for open-circuit voltage (Voc), short-circuit current density (Jsc), Fill Factor (FF) and power conversion efficiency (PCE) for several perovskite material photovoltaic devices produced without a $Ta_2O_5$ nanoparticle electron transport layer and several perovskite material photovoltaic devices produced with a $Ta_2O_5$ nanoparticle electron transport layer, wherein the devices with the $Ta_2O_5$ nanoparticle electron transport layer had the structure of the device illustrated in FIG. 40 and the $Ta_2O_5$ nanoparticles had isobutylsiloxane ligands. In each perovskite material device without the $Ta_2O_5$ nanoparticle electron transport layer, every other layer of the device, beside the electron transport layer, was the same as the layers of the perovskite material photovoltaic devices with a $Ta_2O_5$ nanoparticle electron transport layer. As can be seen from FIG. 48, the devices with the $Ta_2O_5$ nanoparticle electron transport layer demonstrated improved open-circuit voltage (Voc), short-circuit current density (Jsc), Fill Factor (FF) and power conversion efficiency (PCE) compared to devices without a $Ta_2O_5$ nanoparticle electron transport layer. In particular, the average Voc was observed to increase from 0.95 V to 1.03 V and the highest Voc increased from 1.02 V to 1.14 V with addition of a $Ta_2O_5$ nanoparticle electron transport layer. Additionally, the average FF was observed to increase from 64 to 68 in devices incorporating a $Ta_2O_5$ nanoparticle electron transport layer and the highest FFs increased from 69 to 73. Because the current was not observed to change appreciably, these changes in Voc and FF resulted in an increase in average PCE from 12% to 13.5%.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. In particular, every range of values (of the form, "from about a to about b," or, equivalently, "from approximately a to b," or, equivalently, "from approximately a-b") disclosed herein is to be understood as referring to the power set (the set of all subsets) of the respective range of values, and set forth every range encompassed within the broader range of values. Also, the terms in the claims have their plain, ordinary meaning unless otherwise explicitly and clearly defined by the patentee

The invention claimed is:

1. A metal oxide nanoparticle comprising:
a metal oxide core of formula $M_2O_5$, wherein M is tantalum (V) or niobium (V); and
alkylsiloxane ligands bonded to the metal oxide core,
wherein the alkylsiloxane ligands are selected from the group consisting of: isobutylsiloxane, allylsiloxane, vinylsiloxane, n-propylsiloxane, n-butylsiloxane, sec-butylsiloxane, tert-butylsiloxane, phenylsiloxane, n-octylsiloxane, isooctylsiloxane n-dodecylsiloxane, 4-(trimethylsilyl)phenylsiloxane, para-tolylsiloxane, 4-fluorophenylsiloxane, 4-chlorophenylsiloxane, 4-bromophenylsiloxane, 4-iodophenylsiloxane, 4-cyanophenylsiloxane, benzylsiloxane, methylsiloxane, ethylsiloxane, 4-(trifluoromethyl)phenylsiloxane, 4-ammoniumbutylsiloxane, and any combination thereof.

2. The metal oxide nanoparticle of claim 1, wherein the alkylsiloxane ligands are crosslinked to alkylsiloxane ligands of at least one other nanoparticle.

3. The metal oxide nanoparticle of claim 1, wherein the metal oxide core is doped with a metal selected from the group consisting of: Ti, Zr, Hf, Cr, Mo, W, V, and any combination thereof.

4. The metal oxide nanoparticle of claim 1, wherein the metal oxide core comprises $Ta_2O_5$.

5. The metal oxide nanoparticle of claim 1, wherein the metal oxide core comprises $Nb_2O_5$.

* * * * *